(12) United States Patent
Yokoi et al.

(10) Patent No.: US 7,326,565 B2
(45) Date of Patent: Feb. 5, 2008

(54) STORAGE APPARATUS

(75) Inventors: Yasuhiko Yokoi, Hirakata (JP); Mikio Houjou, Higashiosaka (JP); Hiroshi Yamamoto, Neyagawa (JP); Daisuke Etou, Hirakata (JP)

(73) Assignee: Sanyo Electric Co., Ltd., Moriguchi-shi (JP)

( * ) Notice: Subject to any disclaimer, the term of this patent is extended or adjusted under 35 U.S.C. 154(b) by 274 days.

(21) Appl. No.: 10/715,127

(22) Filed: Nov. 18, 2003

(65) Prior Publication Data

US 2004/0147012 A1    Jul. 29, 2004

(30) Foreign Application Priority Data

| Nov. 19, 2002 | (JP) | ............................... 2002-334589 |
| Nov. 19, 2002 | (JP) | ............................... 2002-334590 |
| Nov. 19, 2002 | (JP) | ............................... 2002-334591 |
| Nov. 19, 2002 | (JP) | ............................... 2002-334594 |

(51) Int. Cl.
*C12M 1/00*   (2006.01)
*C12M 3/00*   (2006.01)
*C12M 1/34*   (2006.01)
*B65G 1/00*   (2006.01)
*B65G 65/00*  (2006.01)

(52) U.S. Cl. ............................... 435/303.1; 435/287.3; 435/809; 414/273; 414/787; 414/281; 312/236

(58) Field of Classification Search ............. 435/303.1, 435/287.3, 809; 414/273, 787, 281, 236
See application file for complete search history.

(56) References Cited

U.S. PATENT DOCUMENTS

| 3,445,743 | A | * | 5/1969 | Blair ........................... 318/436 |
| 3,618,734 | A | * | 11/1971 | Khan ........................... 34/219 |
| 4,883,401 | A | * | 11/1989 | Kavieff ........................ 414/273 |
| 5,456,562 | A | * | 10/1995 | Schlecker et al. ........... 414/254 |
| 5,635,398 | A | * | 6/1997 | Kapka et al. ............. 435/286.7 |
| 5,657,720 | A | * | 8/1997 | Walters ....................... 119/317 |
| 5,882,918 | A | * | 3/1999 | Goffe ....................... 435/286.6 |

(Continued)

FOREIGN PATENT DOCUMENTS

JP        11-89559        4/1999

OTHER PUBLICATIONS

English translation of Yoshinaga et al, JP 05-276711, Oct. 22, 1993.*

*Primary Examiner*—Gladys J P Corcoran
*Assistant Examiner*—Nathan A. Bowers
(74) *Attorney, Agent, or Firm*—Kratz, Quintos & Hanson, LLP

(57) ABSTRACT

The invention provides an incubator 1 wherein a microplate transport device 5 is disposed inside a chamber 11 centrally thereof. The transport device 5 comprises a transport table 50 for placing a microplate thereon and is capable of driving the table 50 along the directions of three axes, i.e., X-axis, Y-axis and Z-axis. A plurality of stackers 3 are arranged in the direction of Y-axis at each of opposite sides of the transport device 5 along the direction of X-axis. Each of the stackers 3 has a plurality of microplate accommodating portions arranged in the direction of Z-axis. The microplate is movable into or out of the desired accommodating portion by the transport device 5.

3 Claims, 44 Drawing Sheets

U.S. PATENT DOCUMENTS

| | | | |
|---|---|---|---|
| 6,129,428 A * | 10/2000 | Helwig et al. | 312/114 |
| 6,228,636 B1 * | 5/2001 | Yahiro et al. | 435/303.1 |
| 6,377,867 B1 * | 4/2002 | Bradley et al. | 700/216 |
| 6,568,770 B2 * | 5/2003 | Gonska et al. | 312/9.12 |
| 6,673,595 B2 * | 1/2004 | Barbera-Guillem | 435/286.2 |
| 6,690,994 B1 * | 2/2004 | Smith et al. | 700/218 |
| 2003/0031602 A1 * | 2/2003 | Weselak et al. | 422/104 |
| 2004/0001750 A1 * | 1/2004 | Kremerman | 414/744.1 |

* cited by examiner

FIG. 29

| STACKER TYPE NO. | TYPE | SIZE (mm) | RACK NO. |
|---|---|---|---|
| S1 − NS − 554396 | Normal small 15 | 92 × 135 × 650 | 15 |
| S1 − NL − 554396 | Normal Large 8 | 92 × 135 × 650 | 8 |
| S1 − OP − 275800 | Op 20 | 90 × 132 × 650 | 20 |

FIG. 30

| | |
|---|---|
| STACKER NO. | S0001 |
| STACKER TYPE NO. | S1 − NS − 554396 |
| TYPE | Normal small 15 |
| SIZE (mm) | 92 × 135 × 650 |
| RACK NO. | 15 |

FIG. 31

| | |
|---|---|
| STACKER NO. | S0001 |
| INSTALLATION DATE, TIME | 2002.11.04 14 : 15 |
| INSTALLATION POSITION | A |

FIG. 37

| PLATE TYPE NO. | TYPE | SIZE (mm) | CAVITY NO. |
|---|---|---|---|
| NS – 554396 | Normal small | 86 × 128 × 12 | 96 |
| NL – 554396 | Normal Large | 86 × 128 × 41 | 96 |
| OP – 275800 | Op | 84 × 128 × 6 | NONE |

FIG. 38

| | |
|---|---|
| PLATE NO. | P0001 |
| PLATE TYPE NO. | NS – 554396 |
| TYPE | Normal small |
| SIZE (mm) | 86 × 128 × 12 |
| CAVITY NO. | 96 |

FIG. 39

| | |
|---|---|
| PLATE NO. | P0001 |
| PLACING-IN DATE, TIME | 2002.11.04 15 : 05 |
| ACCOMODATING POSITION | A05 |

FIG. 41

|    | A      | B      | C      | D      | E      | F      | G      | H      |
|----|--------|--------|--------|--------|--------|--------|--------|--------|
| 15 | 015 VC | 030 VC | 045 VC | 060 VC | 075 VC | 090 VC | 105 VC | 120 VC |
| 14 | 014 VC | 029 VC | 044 VC | 059 VC | 074 VC | 089 VC | 104 VC | 119 VC |
| 13 | 013 VC | 028 VC | 043 VC | 058 VC | 073 VC | 088 VC | 103 VC | 118 VC |
| 12 | 012 VC | 027 VC | 042 VC | 057 VC | 072 VC | 087 VC | 102 VC | 117 VC |
| 11 | 011 VC | 026 VC | 041 VC | 056 VC | 071 VC | 086 VC | 101 VC | 116 VC |
| 10 | 010 VC | 025 VC | 040 VC | 055 VC | 070 VC | 085 VC | 100 VC | 115 VC |
| 09 | 009 VC | 024 VC | 039 VC | 054 VC | 069 VC | 084 VC | 099 VC | 114 VC |
| 08 | 008 VC | 023 VC | 038 VC | 053 VC | 068 VC | 083 VC | 098 VC | 113 VC |
| 07 | 007 VC | 022 VC | 037 VC | 052 VC | 067 VC | 082 VC | 097 VC | 112 VC |
| 06 | 006 VC | 021 VC | 036 VC | 051 VC | 066 VC | 081 VC | 096 VC | 111 VC |
| 05 | 005 VC | 020 VC | 035 VC | 050 VC | 065 VC | 080 VC | 095 VC | 110 VC |
| 04 | 004 VC | 019 VC | 034 VC | 049 VC | 064 VC | 079 VC | 094 VC | 109 VC |
| 03 | 003 VC | 018 VC | 033 VC | 048 VC | 063 VC | 078 VC | 093 VC | 108 VC |
| 02 | 002 VC | 017 VC | 032 VC | 047 VC | 062 VC | 077 VC | 092 VC | 107 VC |
| 01 | 001 VC | 016 VC | 031 VC | 046 VC | 061 VC | 076 VC | 091 VC | 106 VC |

FIG. 42

|    | A      | B      | C      | D      | E      | F      | G      | H      |
|----|--------|--------|--------|--------|--------|--------|--------|--------|
| 15 | 015 VC | 030 VC | 045 VC | 060 VC | 075 VC | 090 VC | 105 VC | 120 VC |
| 14 | 014 VC | 029 VC | 044 VC | 059 VC | 074 VC | 089 VC | 104 VC | 119 VC |
| 13 | 013 OP | 028 VC | 043 VC | 058 VC | 073 OP | 088 VC | 103 VC | 118 VC |
| 12 | 012 VC | 027 VC | 042 VC | 057 VC | 072 VC | 087 VC | 102 VC | 117 VC |
| 11 | 011 VC | 026 VC | 041 VC | 056 VC | 071 VC | 086 VC | 101 VC | 116 VC |
| 10 | 010 VC | 025 VC | 040 VC | 055 VC | 070 VC | 085 VC | 100 VC | 115 VC |
| 09 | 009 OP | 024 VC | 039 VC | 054 VC | 069 OP | 084 VC | 099 VC | 114 VC |
| 08 | 008 VC | 023 VC | 038 VC | 053 VC | 068 VC | 083 VC | 098 VC | 113 VC |
| 07 | 007 VC | 022 VC | 037 VC | 052 VC | 067 VC | 082 VC | 097 VC | 112 VC |
| 06 | 006 VC | 021 VC | 036 VC | 051 VC | 066 VC | 081 VC | 096 VC | 111 VC |
| 05 | 005 OP | 020 VC | 035 VC | 050 VC | 065 OP | 080 VC | 095 VC | 110 VC |
| 04 | 004 VC | 019 VC | 034 VC | 049 VC | 064 VC | 079 VC | 094 VC | 109 VC |
| 03 | 003 VC | 018 VC | 033 VC | 048 VC | 063 VC | 078 VC | 093 VC | 108 VC |
| 02 | 002 VC | 017 VC | 032 VC | 047 VC | 062 VC | 077 VC | 092 VC | 107 VC |
| 01 | 001 OP | 016 VC | 031 VC | 046 VC | 061 OP | 076 VC | 091 VC | 106 VC |

FIG. 43

|    | A | B | C | D | E | F | G | H |
|----|---|---|---|---|---|---|---|---|
| 15 | 015 VC | 030 VC | 045 OP | 060 VC | 075 VC | 090 VC | 105 OP | 120 VC |
| 14 | 014 VC | 029 OP | 044 VC | 059 VC | 074 VC | 089 OP | 104 VC | 119 VC |
| 13 | 013 OP | 028 VC | 043 VC | 058 VC | 073 OP | 088 VC | 103 VC | 118 VC |
| 12 | 012 VC | 027 VC | 042 VC | 057 OP | 072 VC | 087 VC | 102 VC | 117 OP |
| 11 | 011 VC | 026 VC | 041 OP | 056 VC | 071 VC | 086 VC | 101 OP | 116 VC |
| 10 | 010 VC | 025 OP | 040 VC | 055 VC | 070 VC | 085 OP | 100 VC | 115 VC |
| 09 | 009 OP | 024 VC | 039 VC | 054 VC | 069 OP | 084 VC | 099 VC | 114 VC |
| 08 | 008 VC | 023 VC | 038 VC | 053 OP | 068 VC | 083 VC | 098 VC | 113 OP |
| 07 | 007 VC | 022 VC | 037 OP | 052 VC | 067 VC | 082 VC | 097 OP | 112 VC |
| 06 | 006 VC | 021 OP | 036 VC | 051 VC | 066 VC | 081 OP | 096 VC | 111 VC |
| 05 | 005 OP | 020 VC | 035 VC | 050 VC | 065 OP | 080 VC | 095 VC | 110 VC |
| 04 | 004 VC | 019 VC | 034 VC | 049 OP | 064 VC | 079 VC | 094 VC | 109 OP |
| 03 | 003 VC | 018 VC | 033 OP | 048 VC | 063 VC | 078 VC | 093 OP | 108 VC |
| 02 | 002 VC | 017 OP | 032 VC | 047 VC | 062 VC | 077 OP | 092 VC | 107 VC |
| 01 | 001 OP | 016 VC | 031 VC | 046 VC | 061 OP | 076 VC | 091 VC | 106 VC |

FIG. 44

|    | A | B | C | D | E | F | G | H |
|----|---|---|---|---|---|---|---|---|
| 15 | 015 OP | 030 VC | 045 OP | 060 VC | 075 OP | 090 VC | 105 OP | 120 VC |
| 14 | 014 VC | 029 OP | 044 VC | 059 VC | 074 VC | 089 OP | 104 VC | 119 VC |
| 13 | 013 OP | 028 VC | 043 VC | 058 VC | 073 OP | 088 VC | 103 VC | 118 VC |
| 12 | 012 VC | 027 VC | 042 VC | 057 OP | 072 VC | 087 VC | 102 VC | 117 OP |
| 11 | 011 OP | 026 VC | 041 OP | 056 VC | 071 OP | 086 VC | 101 OP | 116 VC |
| 10 | 010 VC | 025 OP | 040 VC | 055 VC | 070 VC | 085 OP | 100 VC | 115 VC |
| 09 | 009 OP | 024 VC | 039 VC | 054 VC | 069 OP | 084 VC | 099 VC | 114 VC |
| 08 | 008 VC | 023 VC | 038 VC | 053 OP | 068 VC | 083 VC | 098 VC | 113 OP |
| 07 | 007 OP | 022 VC | 037 OP | 052 VC | 067 OP | 082 VC | 097 OP | 112 VC |
| 06 | 006 VC | 021 OP | 036 VC | 051 VC | 066 VC | 081 OP | 096 VC | 111 VC |
| 05 | 005 OP | 020 VC | 035 VC | 050 VC | 065 OP | 080 VC | 095 VC | 110 VC |
| 04 | 004 VC | 019 VC | 034 VC | 049 OP | 064 VC | 079 VC | 094 VC | 109 OP |
| 03 | 003 OP | 018 VC | 033 OP | 048 VC | 063 OP | 078 VC | 093 OP | 108 VC |
| 02 | 002 VC | 017 OP | 032 VC | 047 VC | 062 VC | 077 OP | 092 VC | 107 VC |
| 01 | 001 OP | 016 VC | 031 VC | 046 VC | 061 OP | 076 VC | 091 VC | 106 VC |

FIG. 45

|    | A      | B      | C      | D      | E      | F      | G      | H      |
|----|--------|--------|--------|--------|--------|--------|--------|--------|
| 15 | 015 OP | 030 VC | 045 OP | 060 VC | 075 OP | 090 VC | 105 OP | 120 VC |
| 14 | 014 VC | 029 OP | 044 VC | 059 OP | 074 VC | 089 OP | 104 VC | 119 OP |
| 13 | 013 OP | 028 VC | 043 OP | 058 VC | 073 OP | 088 VC | 103 OP | 118 VC |
| 12 | 012 VC | 027 OP | 042 VC | 057 OP | 072 VC | 087 OP | 102 VC | 117 OP |
| 11 | 011 OP | 026 VC | 041 OP | 056 VC | 071 OP | 086 VC | 101 OP | 116 VC |
| 10 | 010 VC | 025 OP | 040 VC | 055 OP | 070 VC | 085 OP | 100 VC | 115 OP |
| 09 | 009 OP | 024 VC | 039 OP | 054 VC | 069 OP | 084 VC | 099 OP | 114 VC |
| 08 | 008 VC | 023 OP | 038 VC | 053 OP | 068 VC | 083 OP | 098 VC | 113 OP |
| 07 | 007 OP | 022 VC | 037 OP | 052 VC | 067 OP | 082 VC | 097 OP | 112 VC |
| 06 | 006 VC | 021 OP | 036 VC | 051 OP | 066 VC | 081 OP | 096 VC | 111 OP |
| 05 | 005 OP | 020 VC | 035 OP | 050 VC | 065 OP | 080 VC | 095 OP | 110 VC |
| 04 | 004 VC | 019 OP | 034 VC | 049 OP | 064 VC | 079 OP | 094 VC | 109 OP |
| 03 | 003 OP | 018 VC | 033 OP | 048 VC | 063 OP | 078 VC | 093 OP | 108 VC |
| 02 | 002 VC | 017 OP | 032 VC | 047 OP | 062 VC | 077 OP | 092 VC | 107 OP |
| 01 | 001 OP | 016 VC | 031 OP | 046 VC | 061 OP | 076 VC | 091 OP | 106 VC |

FIG. 46

|    | A      | B      | C      | D      | E      | F      | G      | H      |
|----|--------|--------|--------|--------|--------|--------|--------|--------|
| 15 | 015 OP | 030 VC | 045 OP | 060 VC | 075 OP | 090 VC | 105 OP | 120 VC |
| 14 | 014 OP | 029 OP | 044 VC | 059 OP | 074 OP | 089 OP | 104 VC | 119 OP |
| 13 | 013 OP | 028 VC | 043 OP | 058 VC | 073 OP | 088 VC | 103 OP | 118 VC |
| 12 | 012 VC | 027 OP | 042 VC | 057 OP | 072 VC | 087 OP | 102 VC | 117 OP |
| 11 | 011 OP | 026 VC | 041 OP | 056 VC | 071 OP | 086 VC | 101 OP | 116 VC |
| 10 | 010 OP | 025 OP | 040 VC | 055 OP | 070 OP | 085 OP | 100 VC | 115 OP |
| 09 | 009 OP | 024 VC | 039 OP | 054 VC | 069 OP | 084 VC | 099 OP | 114 VC |
| 08 | 008 VC | 023 OP | 038 VC | 053 OP | 068 VC | 083 OP | 098 VC | 113 OP |
| 07 | 007 OP | 022 VC | 037 OP | 052 VC | 067 OP | 082 VC | 097 OP | 112 VC |
| 06 | 006 OP | 021 OP | 036 VC | 051 OP | 066 OP | 081 OP | 096 VC | 111 OP |
| 05 | 005 OP | 020 VC | 035 OP | 050 VC | 065 OP | 080 VC | 095 OP | 110 VC |
| 04 | 004 VC | 019 OP | 034 VC | 049 OP | 064 VC | 079 OP | 094 VC | 109 OP |
| 03 | 003 OP | 018 VC | 033 OP | 048 VC | 063 OP | 078 VC | 093 OP | 108 VC |
| 02 | 002 OP | 017 OP | 032 VC | 047 OP | 062 OP | 077 OP | 092 VC | 107 OP |
| 01 | 001 OP | 016 VC | 031 OP | 046 VC | 061 OP | 076 VC | 091 OP | 106 VC |

FIG. 47

|    | A      | B      | C      | D      | E      | F      | G      | H      |
|----|--------|--------|--------|--------|--------|--------|--------|--------|
| 15 | 015 OP | 030 OP | 045 OP | 060 VC | 075 OP | 090 OP | 105 OP | 120 VC |
| 14 | 014 OP | 029 OP | 044 VC | 059 OP | 074 OP | 089 OP | 104 VC | 119 OP |
| 13 | 013 OP | 028 VC | 043 OP | 058 OP | 073 OP | 088 VC | 103 OP | 118 OP |
| 12 | 012 VC | 027 OP | 042 OP | 057 OP | 072 VC | 087 OP | 102 OP | 117 OP |
| 11 | 011 OP | 026 OP | 041 OP | 056 VC | 071 OP | 086 OP | 101 OP | 116 VC |
| 10 | 010 OP | 025 OP | 040 VC | 055 OP | 070 OP | 085 OP | 100 VC | 115 OP |
| 09 | 009 OP | 024 VC | 039 OP | 054 OP | 069 OP | 084 VC | 099 OP | 114 OP |
| 08 | 008 VC | 023 OP | 038 OP | 053 OP | 068 VC | 083 OP | 098 OP | 113 OP |
| 07 | 007 OP | 022 OP | 037 OP | 052 VC | 067 OP | 082 OP | 097 OP | 112 VC |
| 06 | 006 OP | 021 OP | 036 VC | 051 OP | 066 OP | 081 OP | 096 VC | 111 OP |
| 05 | 005 OP | 020 VC | 035 OP | 050 OP | 065 OP | 080 VC | 095 OP | 110 OP |
| 04 | 004 VC | 019 OP | 034 OP | 049 OP | 064 VC | 079 OP | 094 OP | 109 OP |
| 03 | 003 OP | 018 OP | 033 OP | 048 VC | 063 OP | 078 OP | 093 OP | 108 VC |
| 02 | 002 OP | 017 OP | 032 VC | 047 OP | 062 OP | 077 OP | 092 VC | 107 OP |
| 01 | 001 OP | 016 VC | 031 OP | 046 OP | 061 OP | 076 VC | 091 OP | 106 OP |

FIG. 48

|    | A      | B      | C      | D      | E      | F      | G      | H      |
|----|--------|--------|--------|--------|--------|--------|--------|--------|
| 15 | 015 OP | 030 VC | 045 OP | 060 VC | 075 OP | 090 VC | 105 OP | 120 VC |
| 14 | 014 OP | 029 OP | 044 VC | 059 OP | 074 OP | 089 OP | 104 VC | 119 OP |
| 13 | 013 OP | 028 VC | 043 OP | 058 VC | 073 OP | 088 VC | 103 OP | 118 VC |
| 12 | 012 OP | 027 OP | 042 VC | 057 OP | 072 OP | 087 OP | 102 VC | 117 OP |
| 11 | 011 OP | 026 VC | 041 OP | 056 VC | 071 OP | 086 VC | 101 OP | 116 VC |
| 10 | 010 OP | 025 OP | 040 VC | 055 OP | 070 OP | 085 OP | 100 VC | 115 OP |
| 09 | 009 OP | 024 VC | 039 OP | 054 VC | 069 OP | 084 VC | 099 OP | 114 VC |
| 08 | 008 OP | 023 OP | 038 VC | 053 OP | 068 OP | 083 OP | 098 VC | 113 OP |
| 07 | 007 OP | 022 VC | 037 OP | 052 VC | 067 OP | 082 VC | 097 OP | 112 VC |
| 06 | 006 OP | 021 OP | 036 VC | 051 OP | 066 OP | 081 OP | 096 VC | 111 OP |
| 05 | 005 OP | 020 VC | 035 OP | 050 VC | 065 OP | 080 VC | 095 OP | 110 VC |
| 04 | 004 OP | 019 OP | 034 VC | 049 OP | 064 OP | 079 OP | 094 VC | 109 OP |
| 03 | 003 OP | 018 VC | 033 OP | 048 VC | 063 OP | 078 VC | 093 OP | 108 VC |
| 02 | 002 OP | 017 OP | 032 VC | 047 OP | 062 OP | 077 OP | 092 VC | 107 OP |
| 01 | 001 OP | 016 VC | 031 OP | 046 VC | 061 OP | 076 VC | 091 OP | 106 VC |

FIG. 54

| PLATE NO. | P0001 |
|---|---|
| PLACING-IN DATE, TIME | 2002.11.04 15 : 05 |
| ACCOMODATING POSITION | A05 |
| MOVING DATE, TIME | 2002.11.04 18 : 25 |
| NEW POSITION | B15 |

STORAGE APPARATUS

FIELD OF THE INVENTION

The present invention relates to storage apparatuses for storing samples on microplates within a chamber which is adjusted to predetermined ambient conditions.

BACKGROUND OF THE INVENTION

FIG. 57 shows an incubator 9 conventionally used for cultivating various microorganisms or cells. The incubator 9 comprises a chamber 91 having an opening 90 closable with a door 92 and a plurality of racks 93 arranged in the interior of the chamber, and is adapted to place a plurality of microplates 31 on the respective racks 93. The chamber 91 is provided with an environment adjusting device (not shown) for adjusting the ambient conditions inside the chamber 91, such as temperature, humidity, carbon dioxide concentration, etc. Samples on the microplates 31 are cultivated under suitable ambient conditions set by the device.

To check the state of samples being cultivated in the incubator 9, the microplate 31 is withdrawn from the chamber 91, and the samples are observed or analyzed using, for example, a microscope. Since the door 92 of the chamber 91 must be opened at such a time, there is the problem that the interior ambient conditions of the chamber 91 are greatly altered by opening the chamber.

Accordingly, an incubator has been proposed in which the microplate is made transportable between a microplate inlet formed in the chamber and a microplate accommodating portion within the chamber so that the microplate can be moved into or out of the accommodating portion automatically (see, for example, the publication of JP-A No. 1999-89559). Because the proposed incubator can be thus adapted by forming a small microplate inlet in the chamber, the internal ambient conditions of the chamber will not be altered greatly by moving the microplate into or out of the chamber.

With the incubator described above, however, the chamber is provided inside thereof with a microplate transport mechanism and also the microplate racks, and nearly half of the interior space of the chamber is occupied by the transport mechanism. This entails the problem of reducing the number of microplates that can be accommodated in the chamber.

The incubator is provided with an environment adjusting device for supplying a gas for adjusting the environment. In order to diffuse the gas into all the microplate accommodating portions having the microplate racks, a gas discharge outlet is provided as directed toward the outside of the space wherein the racks are installed, i.e., toward a space wherein the microplate transport mechanism is disposed. Thus, the gas discharge outlet is positioned at one side of the interior of the chamber, consequently producing a markedly uneven flow of gas inside the chamber and giving rise to the problem that the ambient conditions differ from position to position within the chamber.

Further with the incubator described, the device for transporting the microplate inside the chamber has a motor disposed outside the chamber and provided with an output shaft which extends through the wall of the chamber and is coupled to the mechanism inside the chamber. Accordingly, for the maintenance of the transport device, it is necessary to remove the motor from the chamber and to disassemble the main body of the transport device within the chamber to some extent, hence the problem of necessitating a cumbersome procedure. The motor output shaft extending through the chamber wall further requires provision of a sliding bearing which is highly airtight. This results in the problem of making the chamber complex in construction.

The microplate racks inside the chamber are arranged with a predetermined pitch, so that the incubator described is provided with a microplate transport control program which is specific to the construction of the racks. Accordingly, if it is attempted to install microplate racks of different structure in order to accommodate microplates having a thickness larger than the predetermined pitch, there arises the problem the control program must be rewritten.

Further when a microplate is to be placed into the chamber anew, the operator must specify the position where the microplate is to be placed and needs to input microplate identifying information for the management of the microplate within the chamber. The incubator described therefore has the problem that the operator must perform a very cumbersome manipulation procedure.

SUMMARY OF THE INVENTION

An object of the present invention is to provide a storage apparatus which is adapted to accommodate a large number of containers inside a chamber and wherein the ambient conditions inside the chamber are not different greatly from position to position.

The present invention provides a storage apparatus which comprises a container transport device disposed inside a chamber centrally thereof, and a pair of container racks arranged symmetrically about the device on opposite sides thereof. The container transport device comprises a transport table for placing a container thereon, and a drive mechanism for driving the transport table in the direction of X-axis and the direction of Y-axis which are orthogonal on a horizontal plane, and in the direction of Z-axis orthogonal to these directions. The pair of container racks are arranged on opposite sides of the container transport device in the direction of X-axis.

Each of the accommodating racks has container accommodating portions arranged in the direction of Y-axis and in the direction of Z-axis for accommodating therein respective containers. The container is movable into or out of the desired container accommodating portion of the desired rack by the transport device.

When the container is to be placed into a specified accommodating portion of a specified rack, the transport table of the transport device is driven by the drive mechanism with the container placed thereon first along the directions of Y-axis and X-axis to a position opposed to the specified accommodating portion, and is then driven in one direction along X-axis into the accommodating portion. Thus, the container is accommodated in the specified portion.

A pair of left and right accommodating racks are arranged at opposite sides of the transport device within the chamber. A larger number of containers can therefore be accommodated in the chamber than in the conventional incubator wherein the container accommodating rack is provided at only one side of the transport device.

The storage apparatus of the present invention is adapted to transport containers automatically and to accommodate a large number of containers within the chamber, with the interior of the chamber held under uniform ambient conditions.

Another object of the present invention is to provide a storage apparatus comprising a container transport device which can be removed from the chamber without being disassembled, the chamber being simple in construction.

The present invention provides a storage apparatus for storing samples on containers inside a chamber having ambient conditions adjusted by an environment adjusting device. The chamber has arranged therein a container accommodating rack having a plurality of container accommodating portions, and a container transport device for transporting the container inside the chamber, a motor serving as a power source for the container transport device and being disposed inside the chamber together with a main body portion of the container transport device.

With the storage apparatus of the present invention, the motor of the transport device is disposed inside the chamber along with the main body portion of the device, without causing the output shaft of the motor to extend through the wall of the chamber. Accordingly, the device can be removed from the chamber almost without disassembling the device. The chamber need not be provided with a bearing for supporting the output shaft of the motor. This makes the chamber simpler than in the prior art.

Another object of the present invention is to provide a storage apparatus wherein the operation of the main body thereof, such as the operation of a container transport device, is controllable in accordance with the inherent characteristics of container accommodating stackers, such as the construction of the stackers.

The present invention provides a storage apparatus for storing samples on containers inside a chamber adjusted to predetermined ambient conditions, wherein one or a plurality of stackers can be arranged inside the chamber for accommodating containers therein, each of the stackers being provided with identification information for identifying the stacker. The storage apparatus comprises an apparatus body, storage means for storing the identification information therein, means for reading the identification information provided on the stacker, information processing means for storing the read identification information in the storage means, and control means for controlling the operation of the apparatus body with reference to the identification information stored in the storage means.

Stated mores specifically, the stacker has arranged therein a plurality of container accommodating portions each for placing the container thereinto, and the apparatus body comprises a container transport device installed inside the chamber, the container being movable into or out of the desired accommodating portion in the desired stacker by the container transport device, the operation of the container transport device being controllable by the control means based on the identification information.

When a new stacker is to be installed in the storage apparatus of the invention, the identification information reading means is caused to read the identification information of the stacker, such as identification number or type information. The read identification information is stored in the storage means. When a new container is to be thereafter placed into a specified stacker within the storage apparatus, the construction of the stacker is recognized with reference to the stacker identification information stored in the storage means, and the operation of the transport device is controlled according to the construction of the stacker.

With the storage apparatus of the invention, the operation of the main body of the apparatus can be controlled in accordance with the inherent characteristics of the stacker, such as the construction and maintenance time of the stacker.

Another object of the present invention is to provide a storage apparatus which is easy to manipulate by the operator.

The present invention provides a storage apparatus for storing samples on containers inside a chamber adjusted to predetermined ambient conditions, wherein one or a plurality of container accommodating racks are arranged inside the chamber, each of the containers being provided with identification information for identifying the container. The storage apparatus comprises an apparatus body, storage means for storing the identification information therein, means for reading the identification information provided on the container, information processing means for storing the read identification information in the storage means, and control means for controlling the operation of the apparatus body with reference to the identification information stored in the storage means.

Stated more specifically, the container accommodating rack has arranged therein a plurality of container accommodating portions each for placing the container thereinto, and the apparatus body comprises a container transport device installed inside the chamber, the container being movable into or out of the desired accommodating portion in the desired accommodating rack by the container transport device, the operation of the container transport device being controllable by the control means based on the identification information.

When a new container is to be installed inside the storage apparatus of the invention, the identification information of the container, such as the identification number and type information, is read by the information reading means, and the read information is stored in the storage means. Further the thickness of the container is recognized with reference to the read information, a suitable accommodating rack is selected according to the result of recognition, and the container is transported to a vacant accommodating portion of the selected rack.

With the storage apparatus of the present invention, the container can be automatically transported merely by depressing a start button without necessitating the manipulation by the operator to specify the accommodating portion wherein the container is to be accommodated or to input container identification information. The storage apparatus is therefore easy to manipulate by the operator.

BRIEF DESCRIPTION OF THE DRAWINGS

FIG. 29 shows a stacker information table;

FIG. 30 shows a stacker information form;

FIG. 31 shows a stacker position form;

FIG. 37 shows a microplate information table;

FIG. 38 shows a microplate information form;

FIG. 39 is a diagram showing a form of history of microplate movements to be prepared when a microplate is placed in;

FIG. 40 is a flow chart showing a procedure to be executed when a microplate is placed in;

FIG. 41 shows an example of microplate accommodating portion management table to be prepared when stackers are installed anew;

FIG. 42 shows the table after eight microplates have been accommodated.

FIG. 43 shows the table after thirty microplates have been accommodated.

FIG. 44 shows the table after thirty-eight microplates have been accommodated.

FIG. 45 shows the table after sixty microplates have been accommodated.

FIG. 46 shows the table after sixty-eight microplates have been accommodated.

FIG. 47 shows the table after ninety microplates have been accommodated.

FIG. 48 shows the table after ninety-six microplates have been accommodated.

FIG. 54 is a diagram showing the form of history of microplate movements after the position of the microplate has been shifted within the incubator;

DETAILED DESCRIPTION OF EMBODIMENT

Overall Construction

Figure 1:
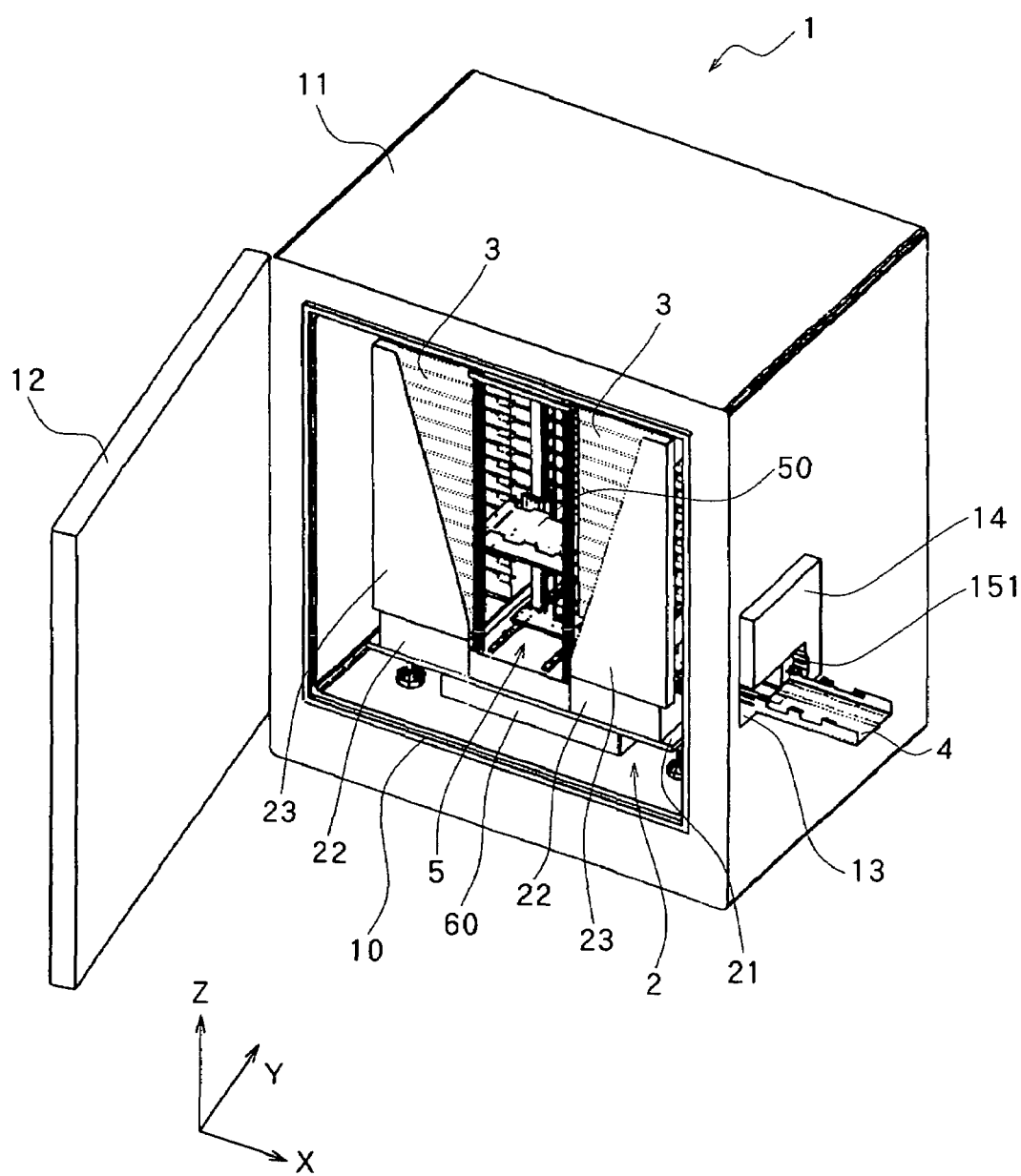
FIG. 1 is a perspective view showing the appearance of an incubator embodying the invention.
Figure 2:
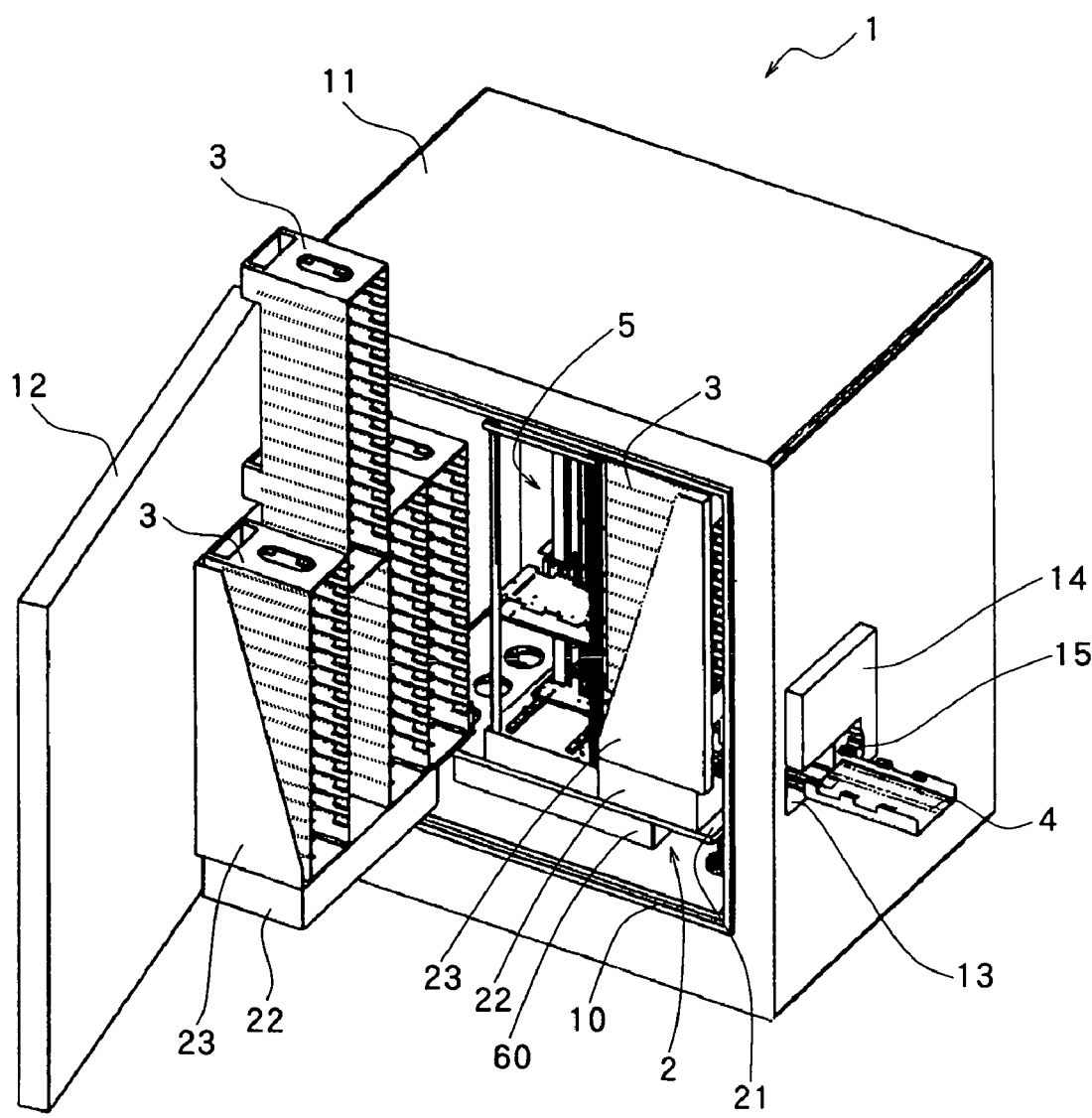
FIG. 2 is a perspective view showing stackers as withdrawn from a chamber.

With reference to FIGS. 1 and 2, an incubator 1 embodying the present invention comprises a chamber 11 having a front opening 10 and a door 12 for closing the opening 10. An incubator unit 2 is accommodated in the interior of the chamber 11. A microplate inlet 13 is formed in a side wall of the chamber 11 and has a microplate carriage mechanism 4 attached thereto.

Figure 3:
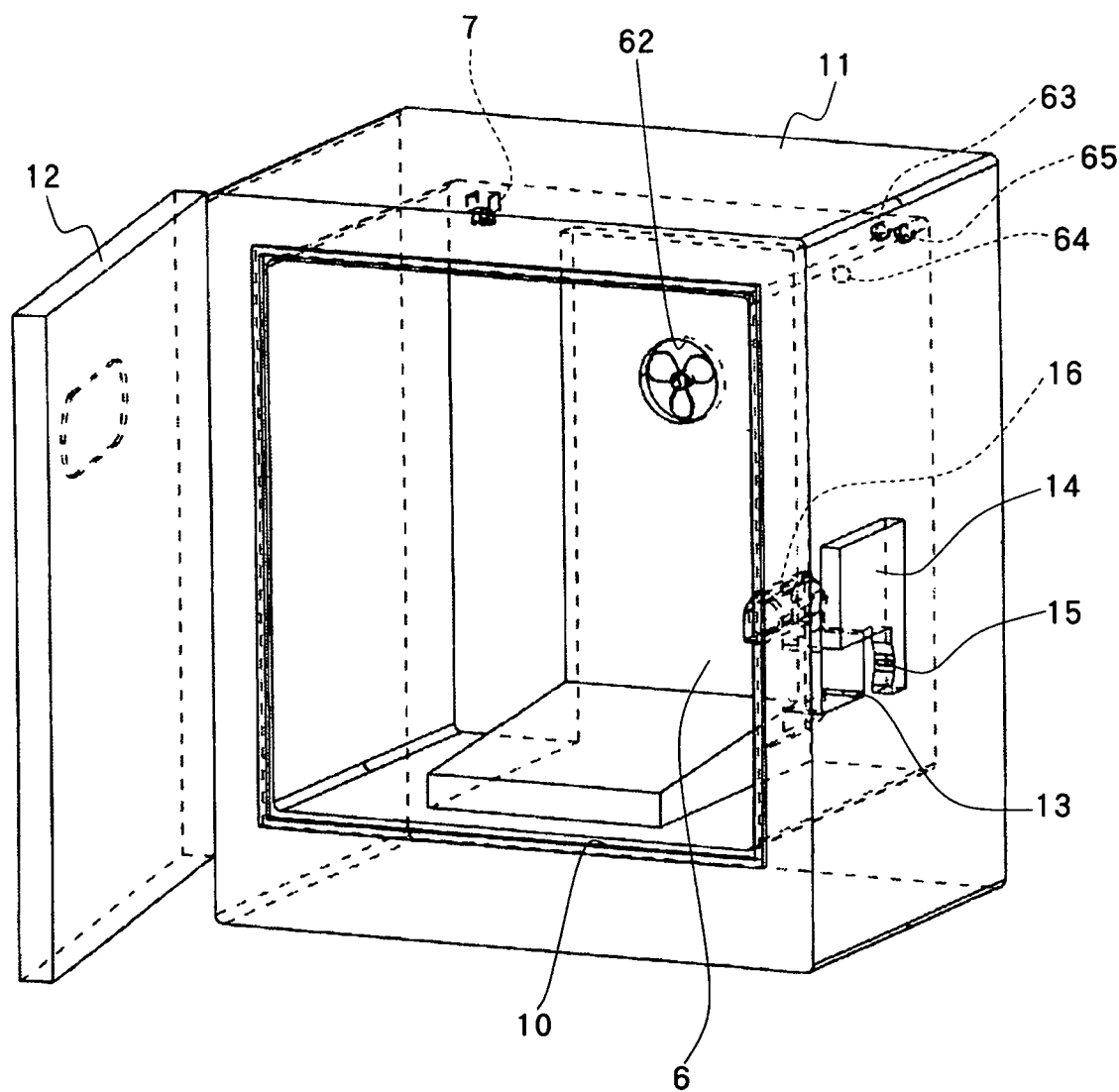
FIG. 3 is a perspective view of the chamber.

As shown in FIG. 3, the chamber 11 has in an inner portion thereof an environment adjusting device 6 for adjusting the temperature, humidity and the concentration of $CO_2$ inside the chamber. The innermost wall of the chamber 11 has a discharge outlet 62 provided with a fan for forcing out a gas for adjusting the environment as specified by the device 6 toward the space in the center of the chamber. Attached to the inside wall of the chamber 11 are a thermometer 63, $CO_2$ densitometer 64 and hygrometer 65 which constitute a sensor unit of the environment adjusting device 6. A camera 7 is installed on the ceiling wall of the chamber 11.

A side wall of the chamber 11 is provided with a shutter mechanism 14 for closing the inlet 13 and an air curtain mechanism 16 for producing an air flow curtain for the inlet 13. The chamber 11 is further provided with a bar code sensor 151 facing the inlet 13 for reading a bar code provided on a microplate during passage through the inlet 13.

Figure 4:
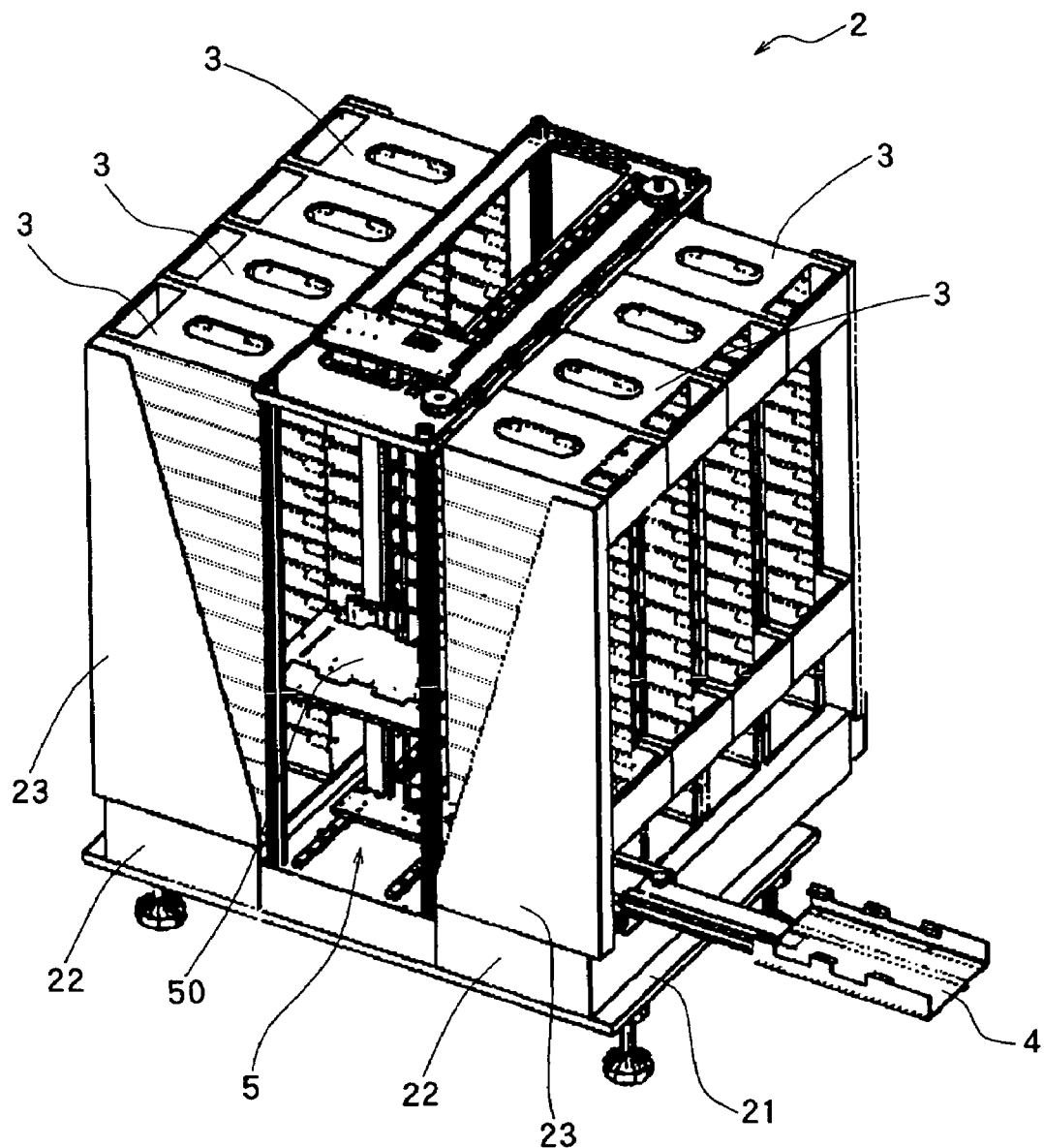
FIG. 4 is a perspective view of an incubator unit.

With reference to FIG. 4, the incubator unit 2 comprises, as mounted on a base 21, a microplate transport device 5 having a microplate transport table 50, and a pair of left and right stacker holders 23, 23 arranged on opposite sides of the transport device 5. The stacker holder 23 retains thereon a plurality of stackers 3 arranged forward or rearward for accommodating microplates.

The stackers 3 on a drawer 22 can be brought out of the opening 10 by withdrawing the drawer 22 through the opening 10 with the door 12 opened as seen in FIG. 2, and the stackers 3 can be withdrawn from the holder 23. The stacker 3 can then be readily replaced by another one and the stacker 3 can be cleaned after use.

Figure 5A:
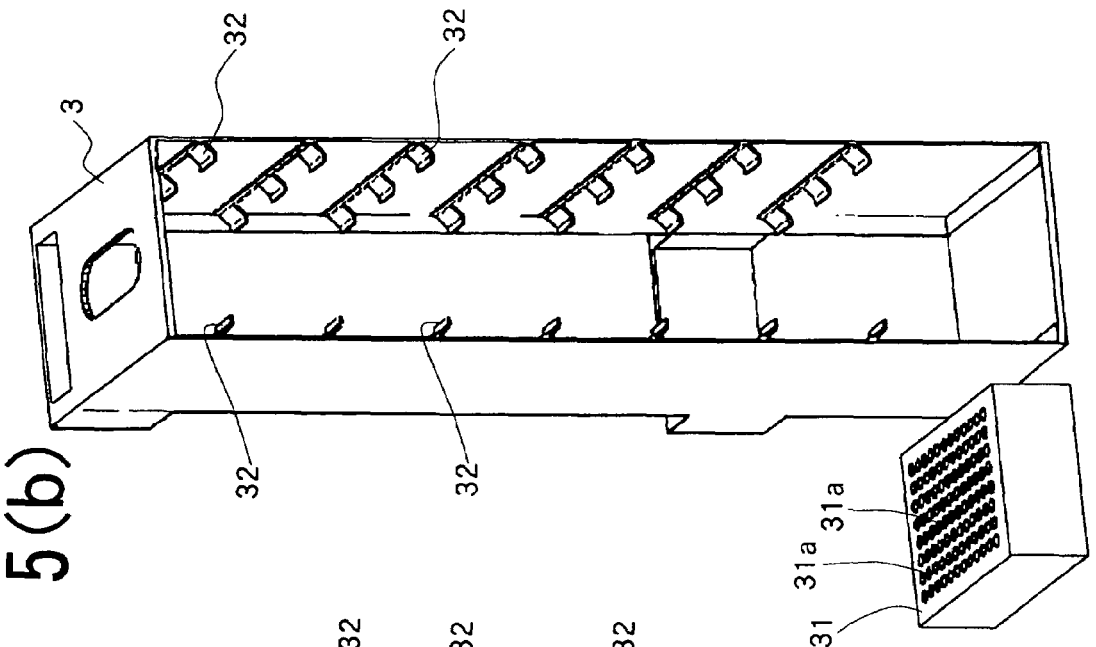
FIG. 5(a) and FIG. 5(b) are perspective views showing two kinds of microplates which are different in height and two kinds of stackers which are different in the number of stages.
Figure 5B:
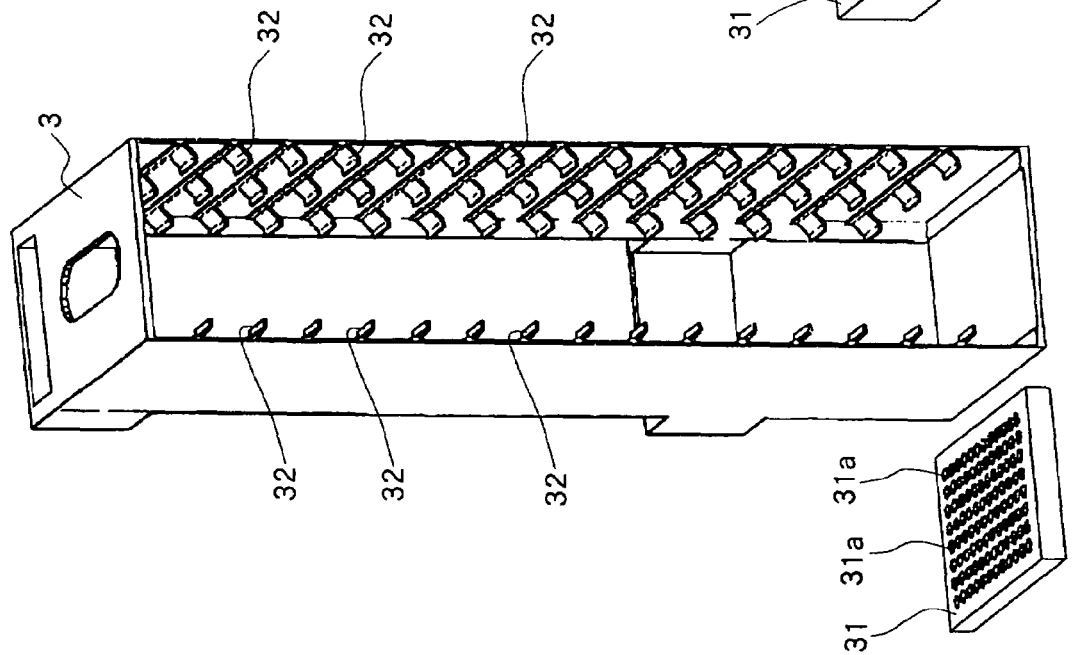

With reference to FIG. 5(a) and FIG. 5(b), a plurality of microplates 31 each having a plurality of cavities 31a for injecting a sample thereinto are accommodated in the stacker 3 in stages. Each of the stages is provided with a pair of support pieces 32, 32 for retaining the microplate 31 in a horizontal posture. Since different kinds of microplates 31 are available which are different in height as illustrated, different kinds of stackers 3 are prepared which are different in the pitch of support pieces 32.

As shown in FIG. 1, the microplate transport device 5 is positioned in the center of the space inside the chamber 11, with the incubator unit 2 accommodated in the chamber 11. Stackers 3 are arranged in the space at each of opposite sides of the device 5. A reservoir pan 60 is disposed below the incubator unit 2 for giving moisture to the air inside the chamber 11.

In the incubator 1 of the present invention, the stackers 3 are arranged within the chamber 1 symmetrically about the transport device 5 on opposite sides thereof as seen in FIG. 1, so that a larger number of stackers 3 can be installed inside the chamber 11 than in the conventional incubator wherein the microplate accommodating racks are provided at only one side of the microplate transport device. An increased number of microplates 31 can therefore be accommodated in the chamber.

Microplate Transport Device 5

Figure 6:
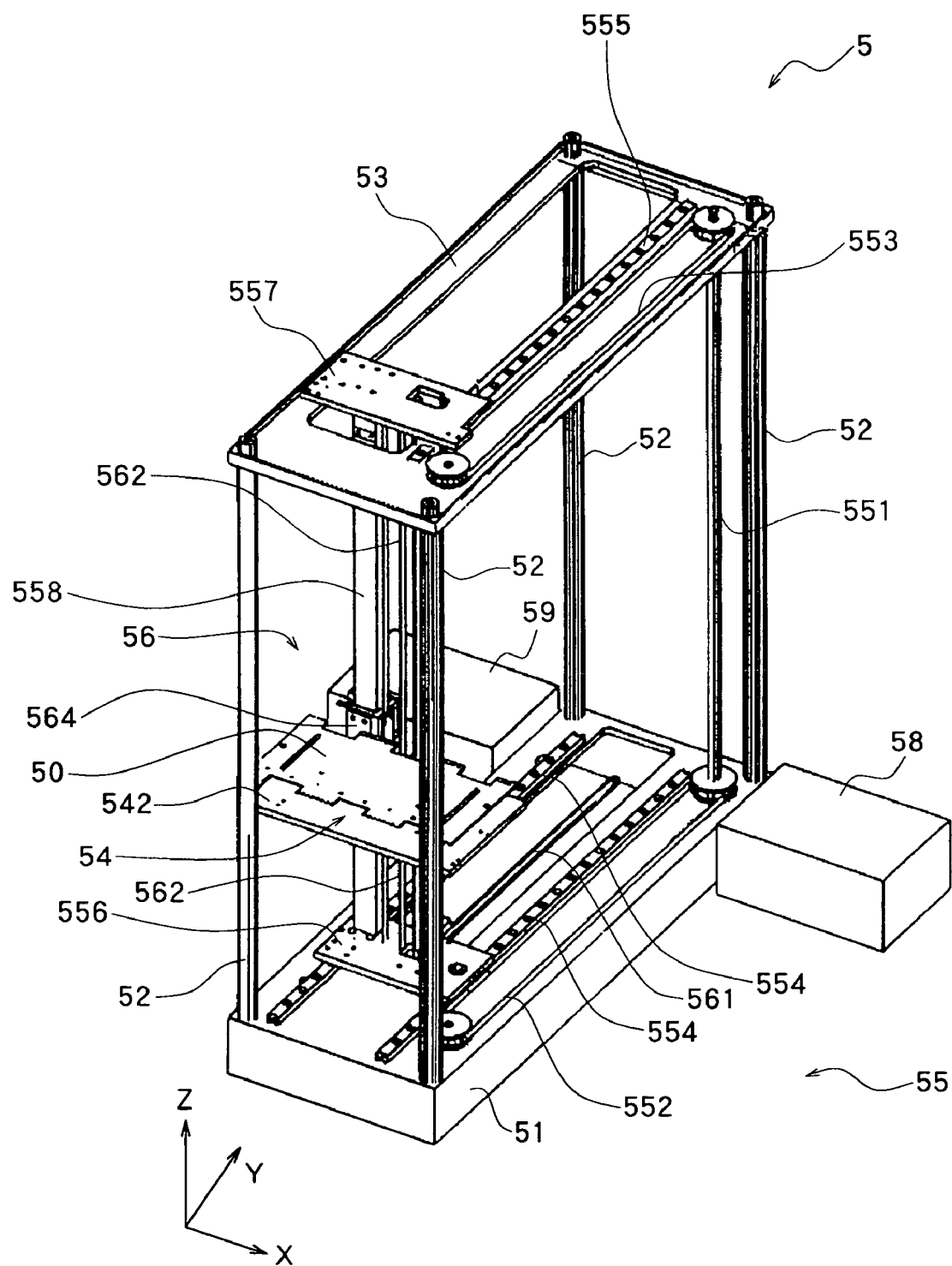
FIG. 6 is a perspective view of a microplate transport device.
Figure 7:
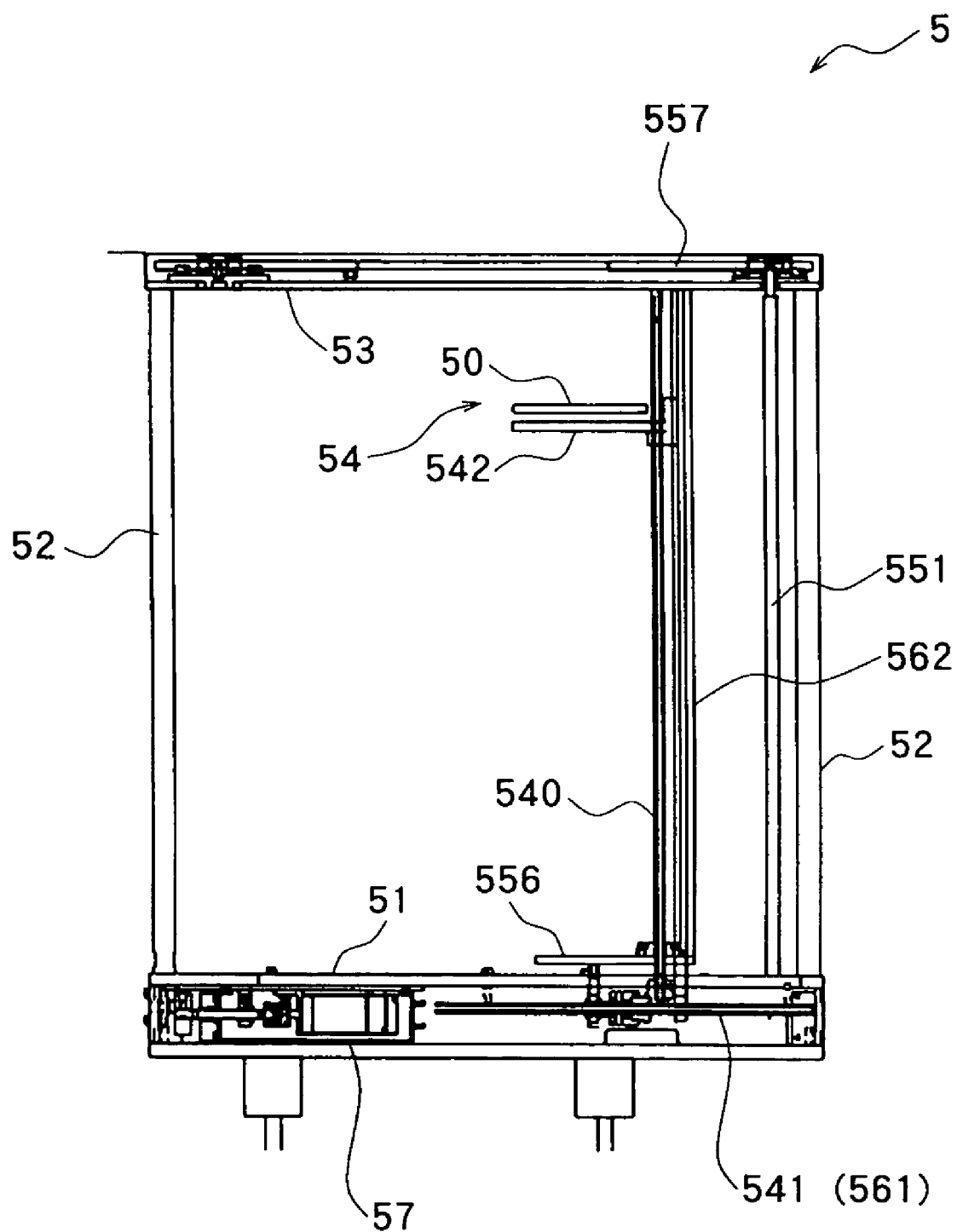
FIG. 7 is a side elevation of the microplate transport device.

The microplate transport device 5 has a frame comprising four posts 52 on a base 51, and an upper plate 53 supported by the posts as shown in FIGS. 6 and 7. The frame is provided with an X-axis transport assembly 54 for driving the transport table 50 in a lateral direction, i.e., in the direction of X-axis, a Y-axis transport assembly 55 for driving the transport table 50 forward or rearward, i.e., in the direction of Y-axis, and a Z-axis transport assembly 56 for driving the transport table 50 upward or downward, i.e., in the direction of Z-axis.

Figure 8:
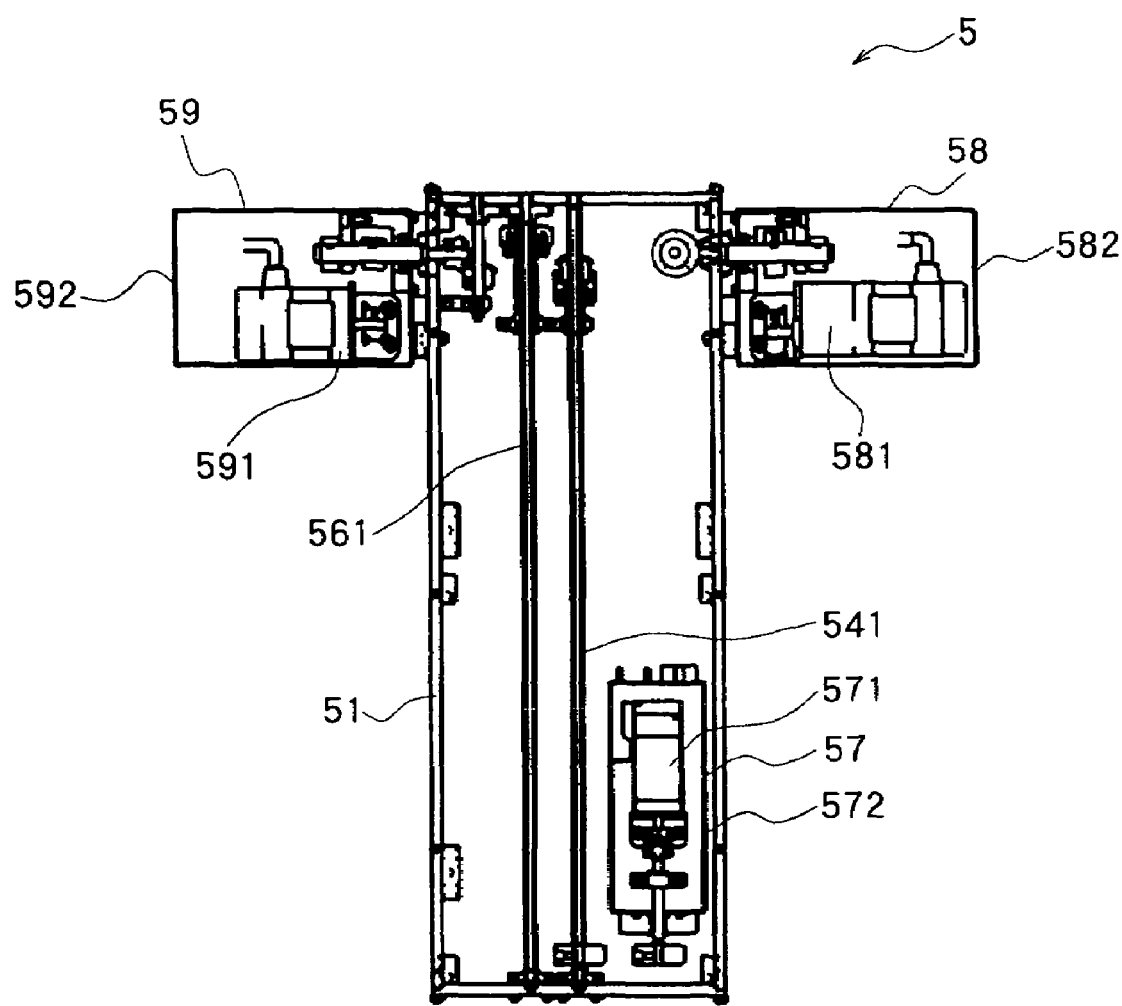
FIG. 8 is a plan view showing the locations of three motors provided for the transport device.

With reference to FIG. 8, mounted on the base 51 are an X-axis motor unit 57 for driving the X-axis transport assembly 54, a Y-axis motor unit 58 for driving the Y-axis transport assembly 55 and a Z-axis motor unit 59 for driving the Z-axis transport assembly 56. The X-axis motor unit 57 comprises an X-axis motor 571 housed in a motor case 572. The Y-axis motor unit 58 comprises a Y-axis motor 581 housed in a motor case 582. The Z-axis motor unit 59 comprises a Z-axis motor 591 housed in a motor case 592. These motors 571, 581, 591 are each a stepping motor.

Y-axis Transport Assembly 55

With reference to FIG. 6, two lower guide rails 554, 554 extending in the direction of Y-axis are installed on the base 51. A lower slide plate 556 is slidably in engagement with the lower guide rails 554, 554. A single upper guide rail 555 extending in the direction of Y-axis is installed on the upper plate 53, and an upper slide plate 557 is slidably in engagement with the rail 555. The lower slide plate 556 and the upper slide plate 557 are interconnected by a vertical bar 558 to provide a reciprocating movable body which is reciprocatingly movable along the direction of Y-axis.

Positioned on the base 51 is a Y-axis drive ladder chain 552 made of stainless steel and extending along the lower guide rail 554. Disposed on the upper plate 53 is a Y-axis drive ladder chain 553 made of stainless steel and extending along the upper guide rail 555. The lower slide plate 556 is connected to one end of the lower ladder chain 552. The upper slide plate 557 is connected to one end of the upper ladder chain 553. Supported by the base 51 and the upper plate 53 is a Y-axis drive shaft 551 extending vertically and to be driven by the Y-axis motor unit 58. The Y-axis drive ladder chains 552, 553 are driven by the rotation of the shaft 551.

Consequently, the lower and upper slide plates 556, 557 are reciprocatingly moved in the directions of Y-axis along the lower guide rails 554, 554 and the upper guide rail 555, and the vertical bar 558 reciprocatingly moves along the direction of Y-axis with this movement.

Figure 9:
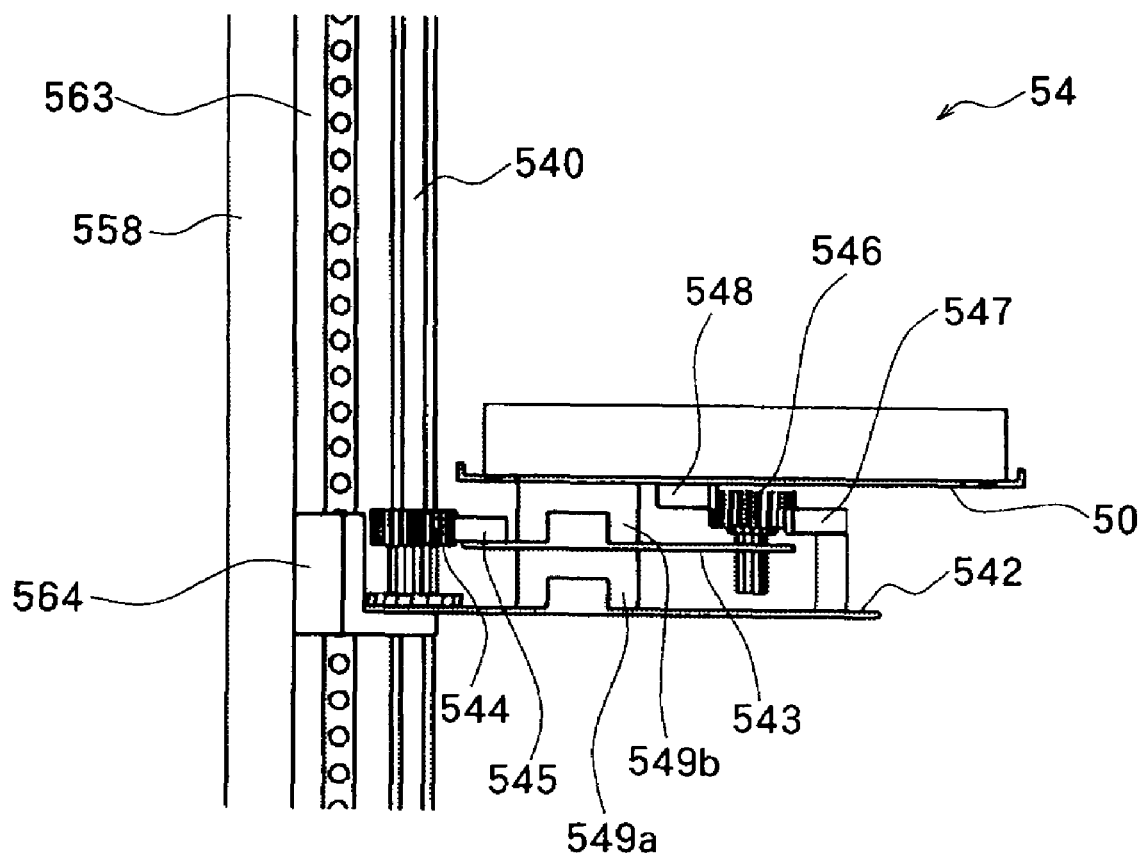
FIG. 9 is a side elevation of an X-axis transport assembly.

As shown in FIG. 9, the vertical bar 558 is provided with a guide rail 563 extending in the direction of Z-axis and having a Z-axis slider 564 slidably engaged therewith. A lift plate 542 is supported by the slider 564 and has placed thereon the transport table 50.

Figure 11A:
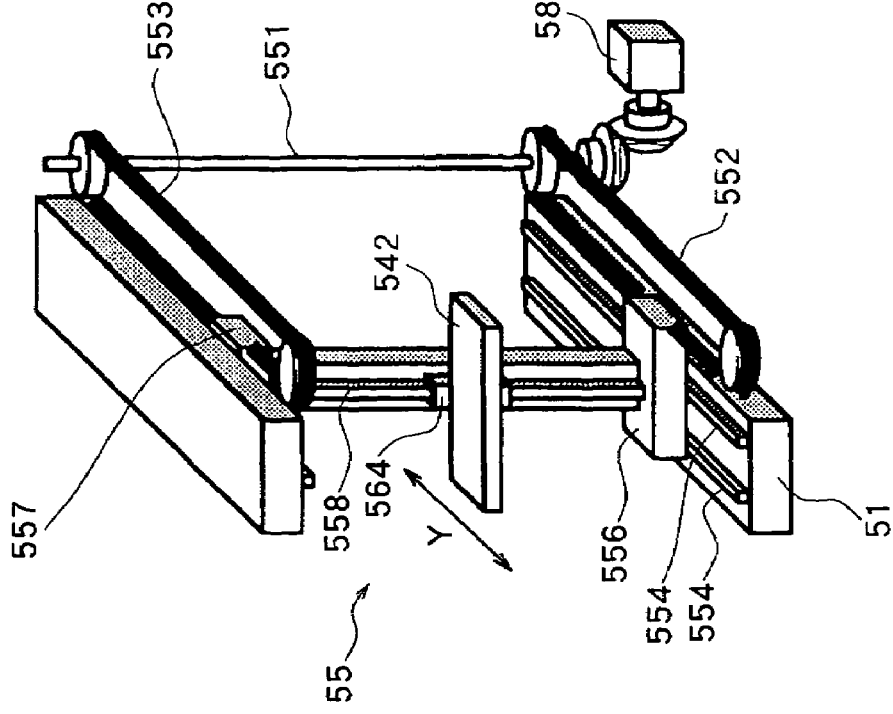
FIG. 11(a), FIG. 11(b) and FIG. 11(c) are perspective views showing power transmission paths of a Y-axis transport assembly, Z-axis transport assembly and the X-axis transport assembly.

The Y-axis transport assembly 55 is thus constructed for driving the transport table 50 in the direction of Y-axis. FIG. 11(a) shows the power transmission path of the Y-axis transport assembly 55. The rotation of the Y-axis motor 581 is delivered to the ladder chains 552, 553 for reciprocatingly moving the lower slide plate 556 and the upper slide plate 557 along the direction of Y-axis. This movement reciprocatingly moves the lift plate 542 along the direction of Y-axis. As a result, the transport table 50 is reciprocatingly moved along the direction of Y-axis.

The Y-axis transport assembly 55 comprises the reciprocating movable body having the lower and upper slide plates 556, 557 and the vertical bar 558, and these slide plates 556, 557 are guided by the lower guide rails 554, 554 and the upper guide rail 555, so that the transport table 50 can be moved along the Y-axis in a stabilized posture.

Z-Axis Transport Assembly 56

With reference to FIG. 8, the base 51 has mounted thereon a Z-axis drive shaft 561 extending along the direction of Y-axis and to be driven by the Z-axis motor unit 59. Further as shown in FIG. 6, extending between the lower slide plate 556 and the upper slide plate 557 is a Z-axis drive ladder chain 562 made of stainless steel. The lift plate 542 is connected to one end of the chain 562. The rotation of the Z-axis drive shaft 561 is delivered to the ladder chain 562.

Figure 11B:
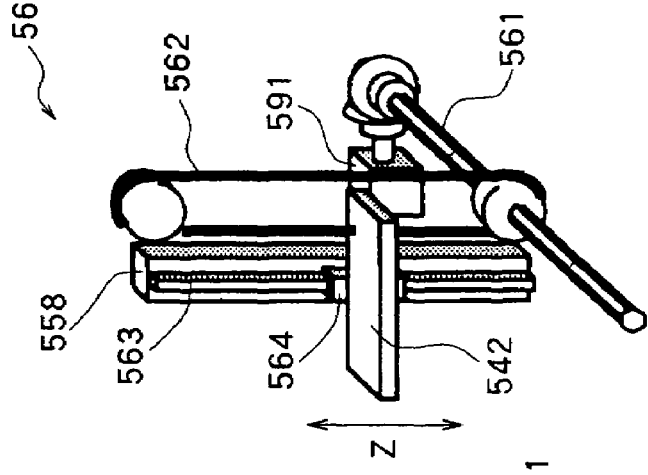

The Z-axis transport assembly 56 for driving the transport table 50 along the direction of Z-axis is thus constructed. FIG. 11(b) shows the power transmission path of the Z-axis transport assembly 56. The Z-axis motor 591 drives the Z-axis drive shaft 561, which in turn drives the ladder chain 562 to reciprocatingly move the lift plate 542 along the direction of Z-axis.

X-Axis Transport Assembly 54

With reference to FIG. 9, a lower-stage slider 549a reciprocatingly movable along the direction of X-axis is mounted on the lift plate 542 projecting from the Z-axis slider 564. An intermediate slide plate 543 is fixed to the top of the lower-stage slider 549a. An upper-stage slider 549b reciprocatingly movable along the direction of X-axis is mounted on the intermediate slide plate 543. The transport table 50 is fixed to the top of the upper-stage slider 549b.

With reference to FIG. 8, a horizontal X-axis drive shaft 541 extending in the direction of Y-axis is mounted on the base 51. The rotation of the X-axis motor unit 57 is delivered to one end of the shaft 541. Further as shown in FIG. 7, a vertical X-axis drive shaft 540 extending in the direction of Z-axis is supported by and extends between the lower slide plate 556 and the upper slide plate 557. The rotation of the horizontal shaft 541 is delivered to the lower end of the vertical shaft 540.

With reference to FIG. 9, a first pinion 544 is engaged with the vertical X-axis drive shaft 540 nonrotatably relative to thereto and is slidable on the shaft axially thereof, while a first rack 545 is disposed on the intermediate slide plate 543. The first pinion 544 and the first rack 545 are in mesh with each other. A second pinion 546 is provided on the intermediate slide plate 543, while a second rack 547 is mounted on the lift plate 542. The second pinion 546 and the second rack 547 are in mesh with each other.

Figure 11C:
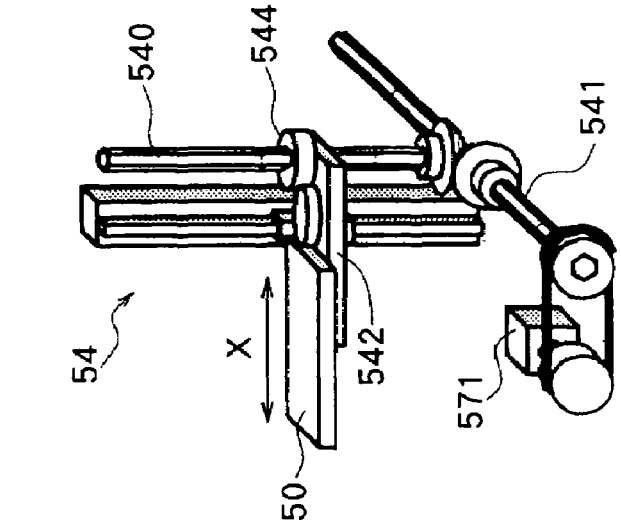

The X-axis drive assembly 54 is thus constructed for driving the transport table 50 along the direction of X-axis. FIG. 11(c) shows the power transmission path of the assembly 54. The rotation of the X-axis motor 571 is delivered to the pinion 544 via the horizontal X-axis drive shaft 541 and the vertical X-axis drive shaft 540 to drive the transport table 50 along the direction of X-axis by the rotation of the pinion 544.

Figure 10A:
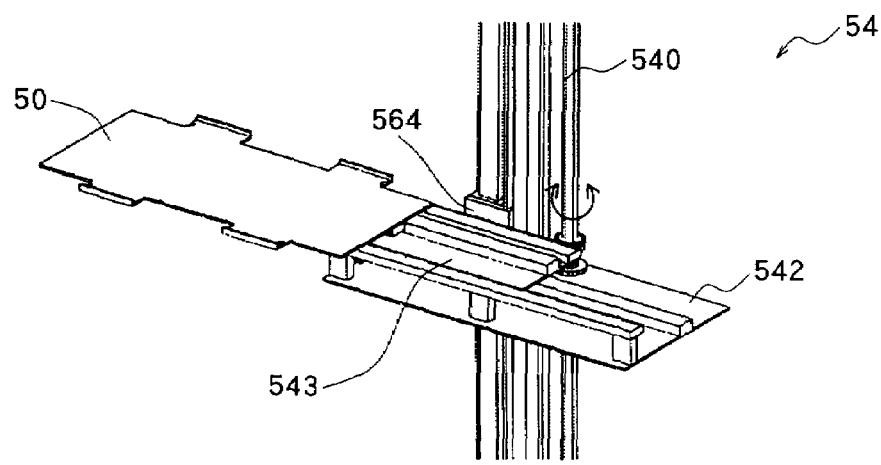
FIG. 10(a) and FIG. 10(b) are perspective views showing the movement of the X-axis transport assembly.
Figure 10B:
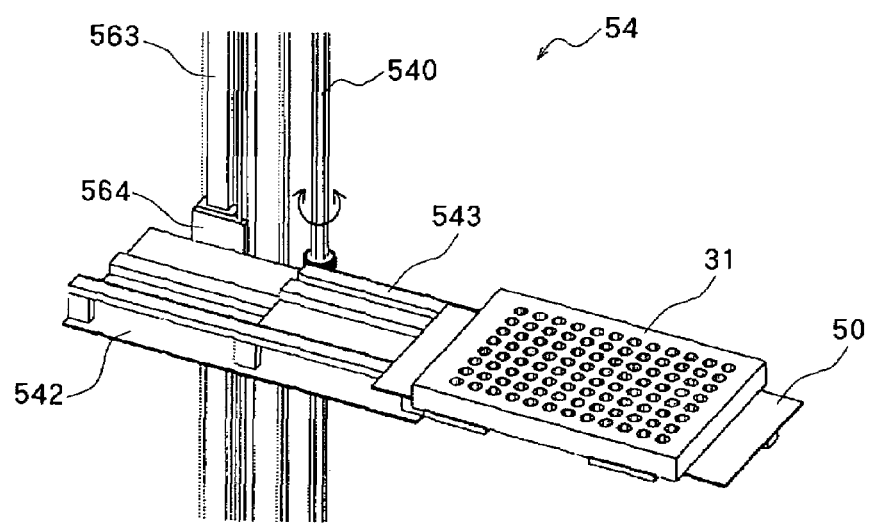

With reference to FIG. 10(a) and FIG. 10(b) showing the movement of the X-axis transport assembly 54, the transport table 50 in a reference position wherein the table is located in overlapping relation with the lift plate 542 is moved to a leftward limit position shown in FIG. 10(a) into the stacker at the left, or to a rightward limit position shown in FIG. 10(b) into the stacker at the right, by the forward or reverse rotation of the vertical X-axis drive shaft 540.

Microplate Carriage Mechanism 4

Figure 12:
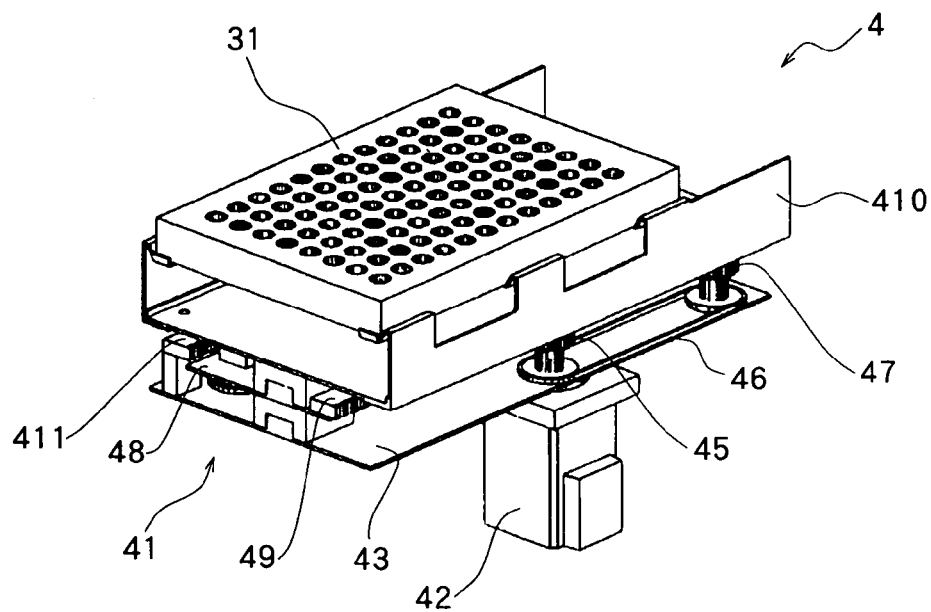
FIG. 12 is a perspective view of a microplate carriage mechanism.
Figure 13:
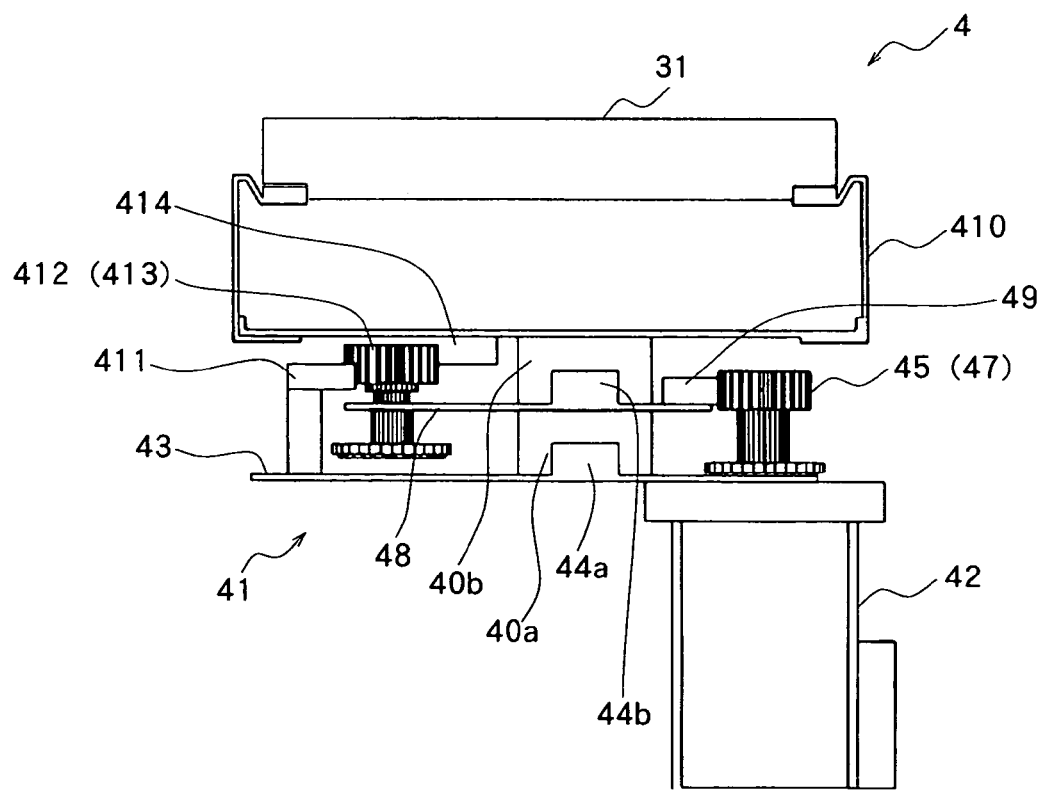
FIG. 13 is a side elevation of the microplate carriage mechanism.
Figure 14:
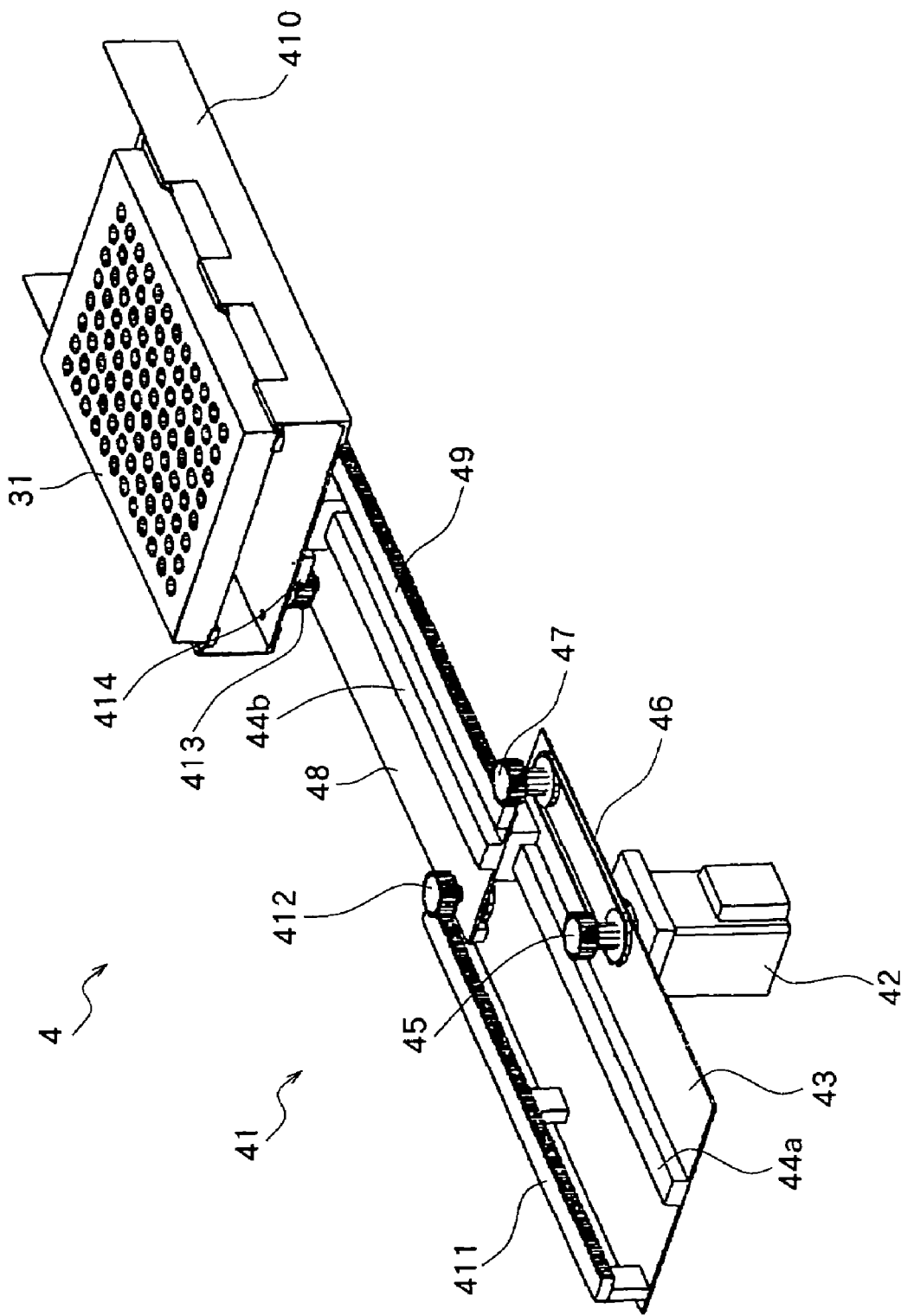
FIG. 14 is a perspective view showing the movement of the microplate carriage mechanism.

With reference to FIGS. 12 to 14, the microplate carriage mechanism 4 comprises a reciprocating transport assembly 41 and a motor unit 42 for driving the assembly 41. The transport assembly 41 has a guide rail 44a extending in the direction of X-axis and provided on a base 43, and a lower-stage slider 40a is slidably in engagement with the guide rail 44a. An intermediate slide plate 48 is fixed to the top of the lower-stage slider 40a. A guide rail 44b extending in the direction of X-axis is provided on the intermediate slide plate 48, and an upper-stage slider 40b is slidably in engagement with the guide rail 44b. A microplate carrier 410 is fixed to the top of the upper-stage slider 40b.

The base 43 is provided with the carriage motor unit 42, which comprises a stepping motor housed in a motor case. Also mounted on the base 43 are a first and a second pinion 45, 47 to be driven by the motor unit 42 at the same time, while a first rack 49 is mounted on the intermediate slide plate 48. The first pinion 45 and the first rack 49 are opposed to each other in meshing engagement, with the second pinion 47 in mesh with the first rack 49. A third pinion 412 is mounted on the intermediate slide plate 48, while a second rack 411 is mounted on the base 43. The pinion 412 and the rack 411 are in mesh with each other. The slide plate 48 is also provided with a fourth pinion 413, while a third rack 414 is attached to the rear wall of the microplate carrier 410. The pinion 413 and the rack 414 are in mesh with each other.

Accordingly, when the first and second pinions 45, 47 are rotatingly driven clockwise by the carriage motor unit 42 in the state shown in FIG. 12, the intermediate slide plate 48 is driven in the direction of X-axis. At the same time, the microplate carrier 410 on the slide plate 48 is driven along the direction of X-axis, with the result that the carrier 410 is greatly projected from the base 43 as seen in FIG. 14. Alternatively when the first and second pinions 45, 47 are rotatingly driven counterclockwise by the motor unit 42 in the state shown in FIG. 14, the carrier 410 is returned to the initial position shown in FIG. 12.

With the incubator 1 of the present invention, the ladder chains of stainless steel are used in the power transmission mechanisms for the microplate carriage mechanism 4 and the microplate transport device 5 as described above. This obviates the likelihood that the moisture inside the chamber 11 will cause oxidative corrosion to the power transmission mechanisms.

Construction of the Motor Units

As already described, the X-axis motor unit 57, Y-axis motor unit 58, Z-axis motor unit 59 and carriage motor unit 42 each comprise a motor housed in a motor case. Further stated more specifically with reference to FIG. 15 showing the construction of the Y-axis motor unit 58 as an example, the construction is adapted to prevent the condensation of water vapor on the motor.

Figure 15:
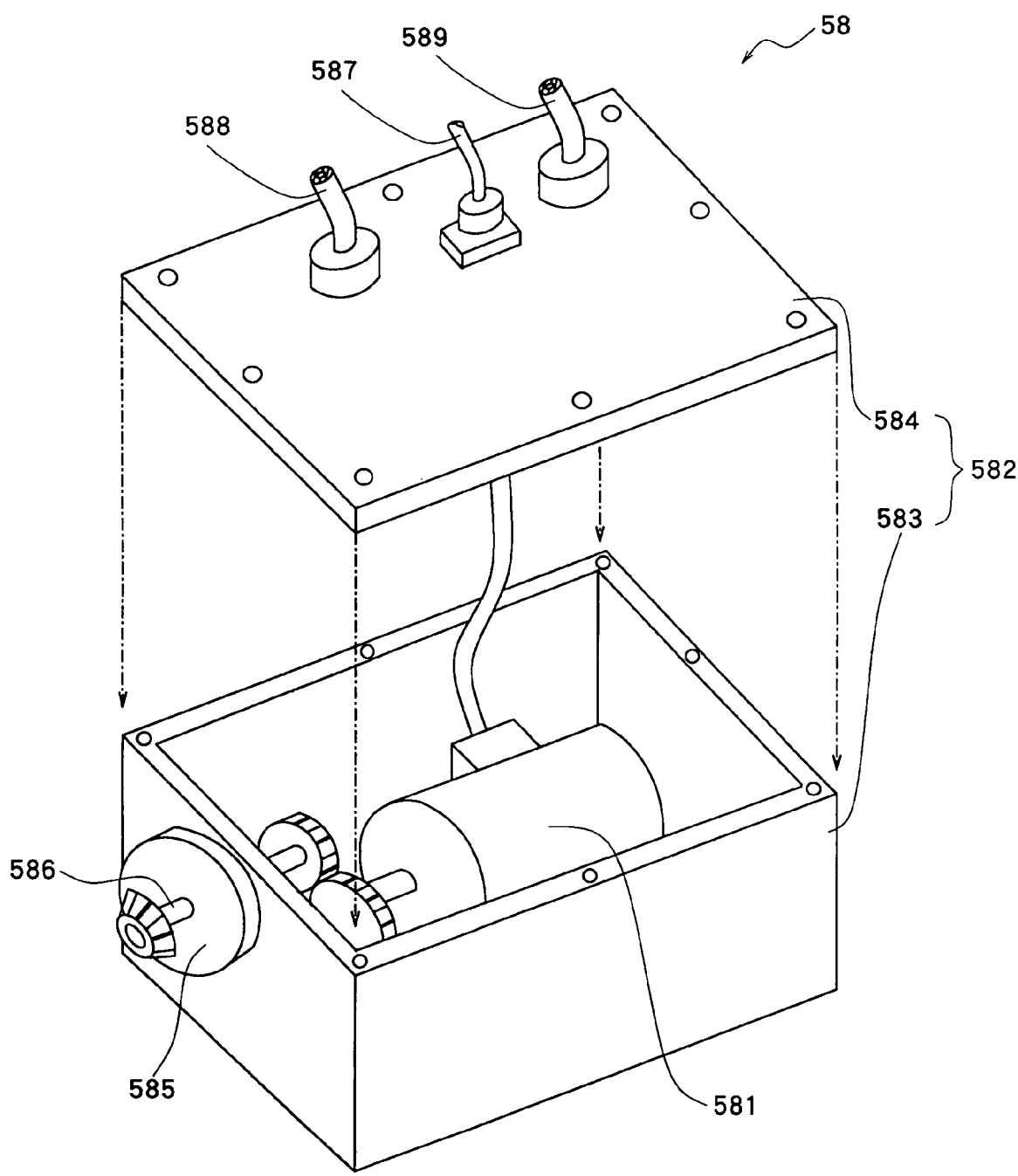
FIG. 15 is an exploded perspective view of a Y-axis motor unit.

In the case of the Y-axis motor unit 58, the motor case 582 comprises a case body 583 and a lid 584 and has its interior hermetically closed, as shown in FIG. 15. The Y-axis motor 581 is housed in the motor case 582 and has an output shaft 586 hermetically extending through a sliding bearing 585 attached to the case 582. The output shaft 586 has an outer end projecting outward from the case 582.

Attached to the lid 584 of the motor case 582 are an air admitting hose 588 for introducing air into the motor case 582 and a vent hose 589 for discharging air from inside the case 582, whereby the air within the motor case 582 is circulated. The lid 584 of the case 582 has also connected thereto a cable 587 for feeding electric power and a control signal to the Y-axis motor 581.

The construction of the motor unit described above holds the interior of the motor case 582 airtight and permits the circulation of air through the motor case 582, so that even if the ambient temperature of the motor unit 50 drops, condensation of water vapor is unlikely to occur inside the case 582. The X-axis motor unit 57, Z-axis motor unit 58 and carriage motor unit 42 also have the same construction as the unit 58 and are made free from the condensation.

Photographing System

Figure 16:
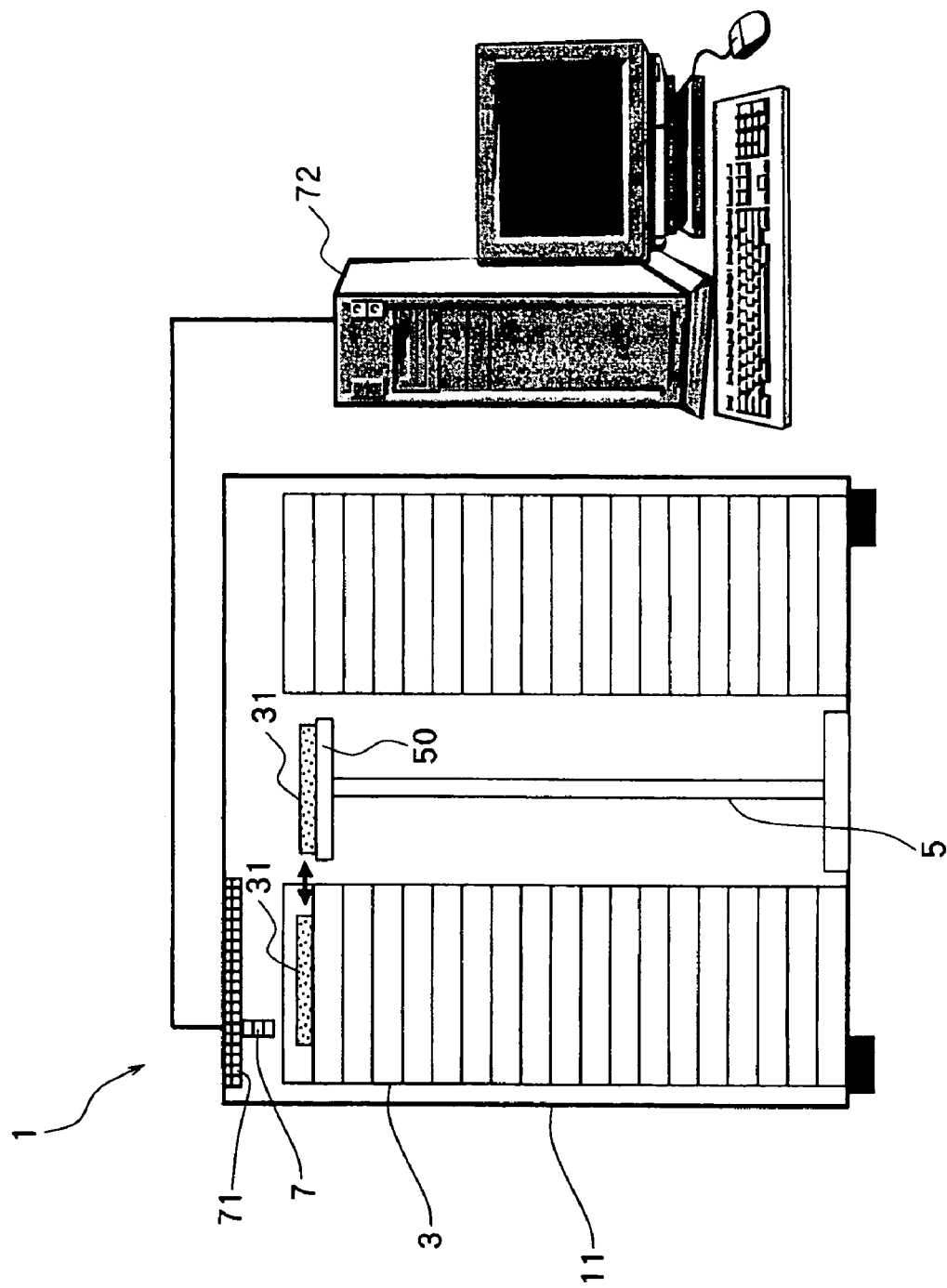
FIG. 16 is a diagram showing a camera provided for the chamber.

The incubator 1 according to the invention further has a camera 7 attached to the ceiling wall of the chamber 11 as seen in FIG. 16. The camera 7 faces the microplate accommodating portion to be photographed and provided at the uppermost stage in the specified stacker 3 for photographing the microplate placed in the accommodating portion. The camera 7 can be driven in the direction of X-axis and the direction of Y-axis by a camera drive mechanism 71. The camera 7 and the drive mechanism 71 are connected to an analyzer 72 for controlling the movement of the camera 7. For the analysis of the sample, the analyzer 72 processes the image data obtained by the camera 7 and performs calculations.

For the camera 7 to photograph the microplate 31, the microplate 31 to be photographed is transported to the microplate accommodating portion to be photographed by the transport device 5. The sample on the microplate 31 is photographed while the camera 7 is being driven along the direction of X-axis and the direction of Y-axis, and the resulting image is fed to the analyzer 72.

Control System

Figure 17:
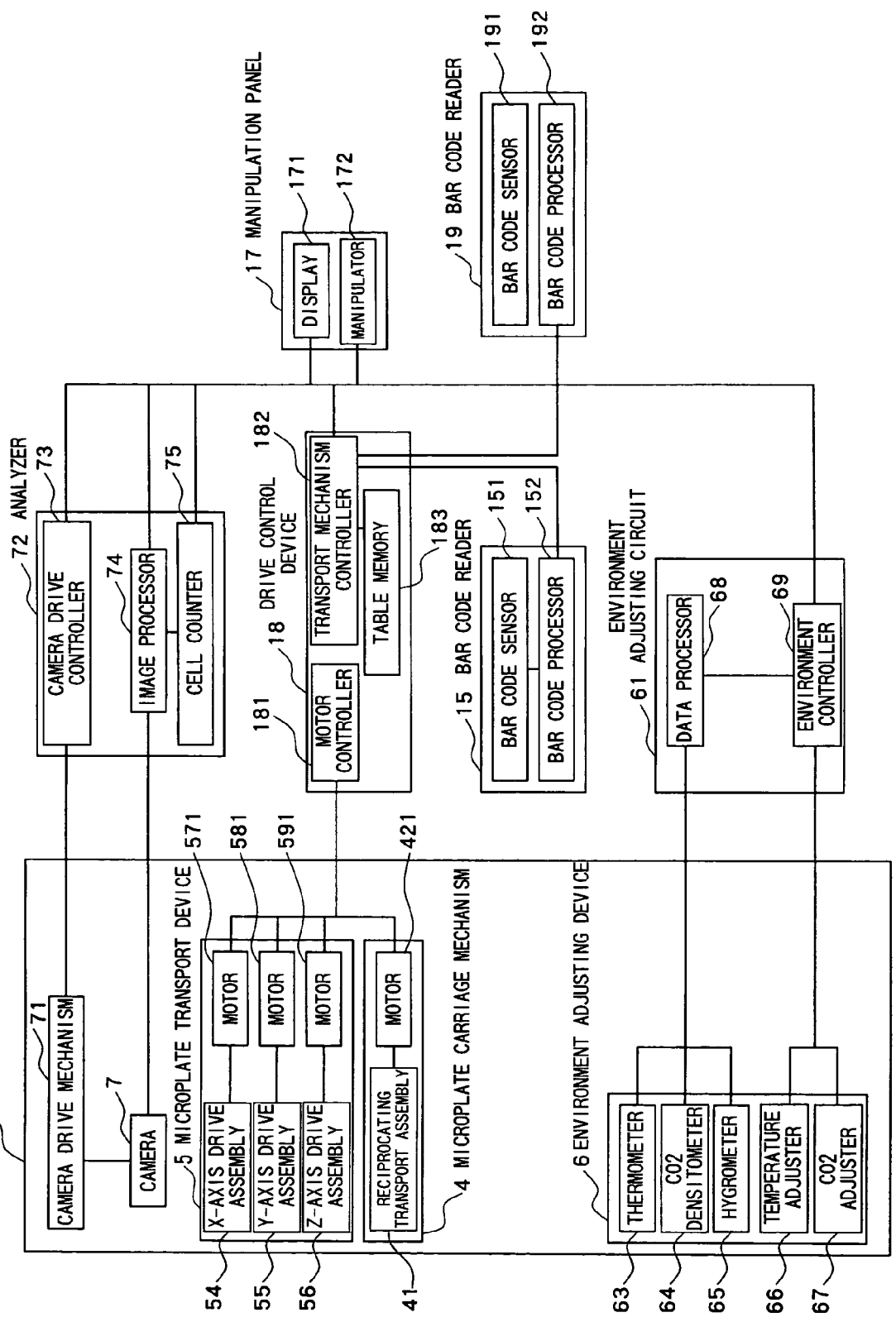
FIG. 17 is a control block diagram of the incubator of the invention.

FIG. 17 shows the construction of a control system of the incubator 1 of the present invention. The microplate carriage mechanism 4 and the microplate transport device 5 are connected to a drive control device 18 comprising a motor controller 181, transport mechanism controller 182 and table memory 183 for controlling the transport of microplates into or out of the chamber 11 and transport of microplates inside the chamber.

The environment adjusting device 6 comprises aforementioned thermometer 63, $CO_2$ densitometer 64 and hygrometer 65 which provides a sensor unit, and further comprises a temperature adjuster 66 and $CO_2$ adjuster 67 to be operated according to the detected values obtained by the sensor unit. The device 6 has its operation controlled by an environment adjusting circuit 61 comprising a data processor 68 and an environment controller 69.

The camera 7 and the camera drive mechanism 71 are connected to the analyzer 72, which comprises a camera drive controller 73, image processor 74 and cell counter 75. The camera drive controller 73 controls the drive of the camera 7, and the image data obtained by the camera 7 is processed as required by the image processor 74. The number of cells in the sample on the microplate is counted by the cell counter 75.

A manipulation panel 17 comprising a display 171 and a manipulator 172 is connected to the drive control device 18, environment adjusting circuit 61 and camera drive controller 73. When manipulated, the manipulator 172 gives various operation commands, and the operating state can be monitored by the display 171.

Further connected to the drive control device 18 are a first bar code reader 15 for reading the bar codes provided on microplates 31 and a second bar code reader 19 for reading the bar codes provided on stackers. The first bar code reader 15 is provided by connecting a bar code processor 152 to the bar code sensor 151 which is attached to the microplate inlet 13 as previously stated. The second bar code reader 19 is a unit comprising a bar code sensor 191 and a bar code processor 192, and can be held by the hand to read the bar code on the stacker 3.

Operation of the Incubator (1)

Figure 18:
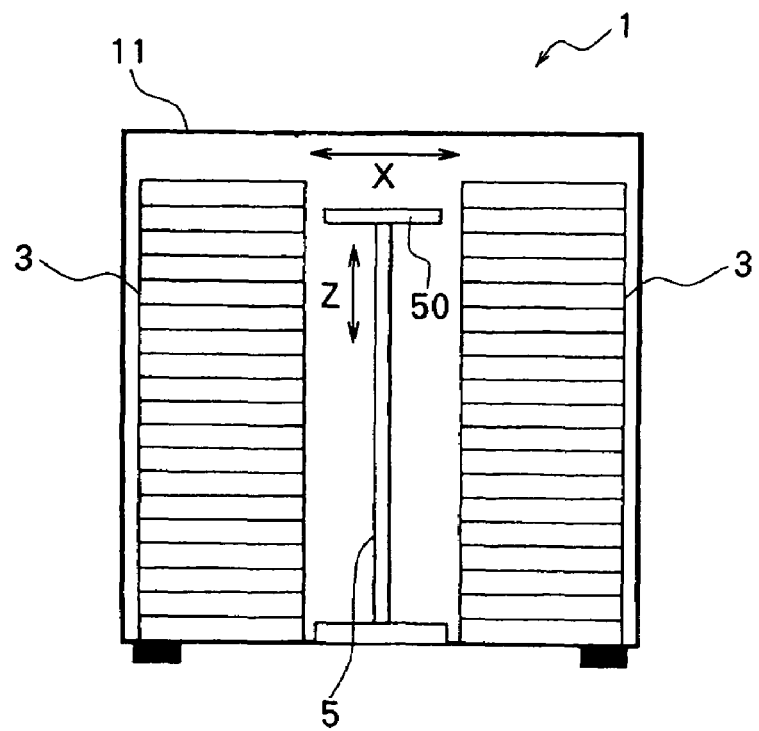
FIG. 18 is a front view showing the directions of movement of the microplate transport device in the incubator of the invention.
Figure 19:
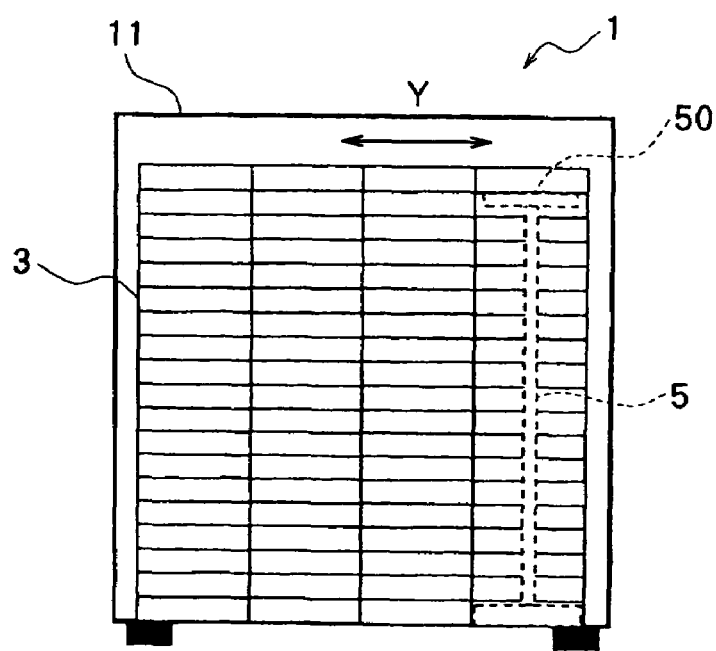
FIG. 19 is a side elevation of the same.

With the incubator 1 of the present invention, the transport table 50 is moved along the directions of X-axis, Y-axis and Z-axis by the operation of the transport device 5, with a plurality of stackers 3 installed within the chamber 11 as shown in FIGS. 18 and 19, whereby a microplate is moved into or out of the desired accommodating portion in the desired stacker 3.

For example, when a microplate 31 is to be placed into a certain microplate accommodating portion, the microplate is transported into the chamber 11 first by the microplate carriage mechanism 4. At this time, the carriage mechanism 4 is operated to cause the microplate carrier 410 to project outward from the inlet 13 of the chamber 11 as shown in FIG. 14 (see FIG. 1). After the microplate 31 is placed on the carrier 410, the carriage mechanism 4 is operated to move the carrier 410 into the chamber 11 as shown in FIG. 12.

The Y-axis transport assembly 55 and the Z-axis transport assembly 56 of the transport device 5 are operated to bring the transport table 50 to a position opposed to the microplate inlet 13, and the X-axis transport assembly 54 is moved toward the inlet 13, moving the table 50 in its reference position to a position between the carrier 410 of the carriage mechanism 4 and the microplate 31. The table 50 is then slightly raised by the operation of the Z-axis transport assembly 56 to place the microplate 31 onto the table 50, and the X-axis transport assembly 54 thereafter operates to return the table 50 to the reference position.

Subsequently, the Y-axis transport assembly 55 and the Z-axis transport assembly 56 of the device 5 are operated to move the table 50 to a position opposed to a predetermined accommodating portion of the specified stacker 3, whereupon the X-axis transport assembly 54 is operated to move the table 50 from its reference position into the accommodating portion. The Z-axis assembly 56 is then operated to slightly lower the table 50 and transfer the microplate 31 on the table 50 to the accommodating portion. This movement is followed by the operation of the X-axis assembly 54 to return the table 50 to the reference position.

When a microplate 31 in a certain microplate accommodating portion of a stacker 3 within the chamber 11 is to be brought out of the chamber 11, an operation reverse to the above placing-in and transport operation is performed. Stated more specifically, the transport table 50 is moved to a position opposed to the accommodating portion by the operation of the Y-axis and Z-axis transport assemblies 55, 56 of the transport device 5, and the X-axis transport assembly 54 is subsequently moved leftward or rightward depending on whether the accommodating portion is positioned at the left or right to move the table 50 into the accommodating portion and to position the microplate onto the table 50.

The transport device 5 then operates, transporting the microplate 31 on the table 50 to the inlet 13 of the chamber 11 and thereafter delivering the microplate 31 from the table 50 to the carrier 410 of the carriage mechanism 4. The mechanism 4 operates to move the microplate 31 on the carrier 410 out of the chamber 11.

Figure 20:
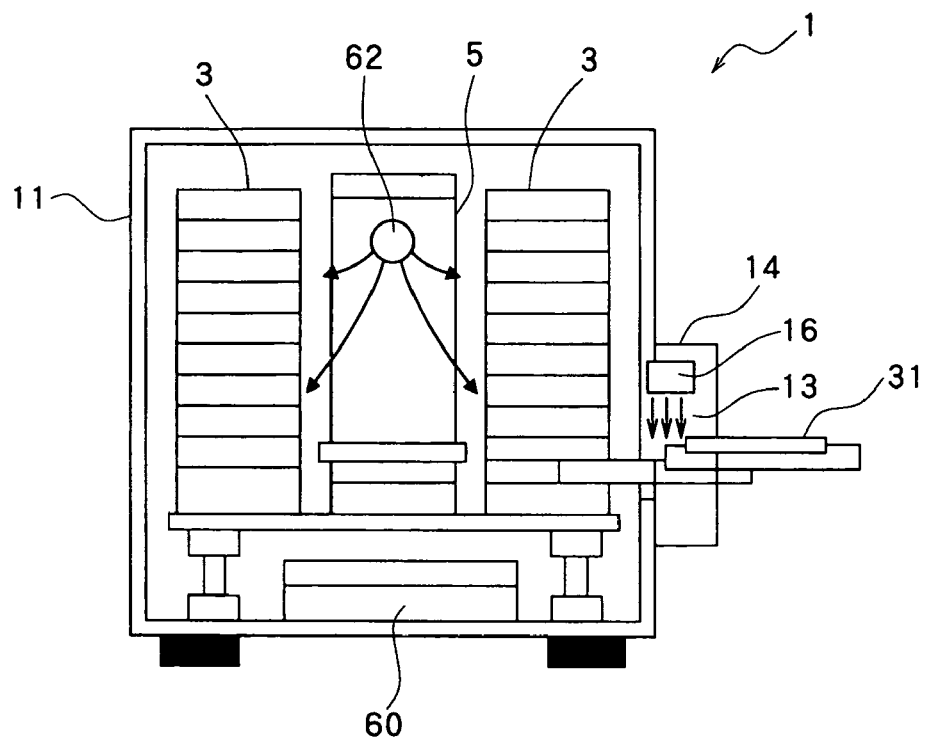
FIG. 20 is a front view for illustrating flows of a gas forced out of a discharge outlet.
Figure 21:
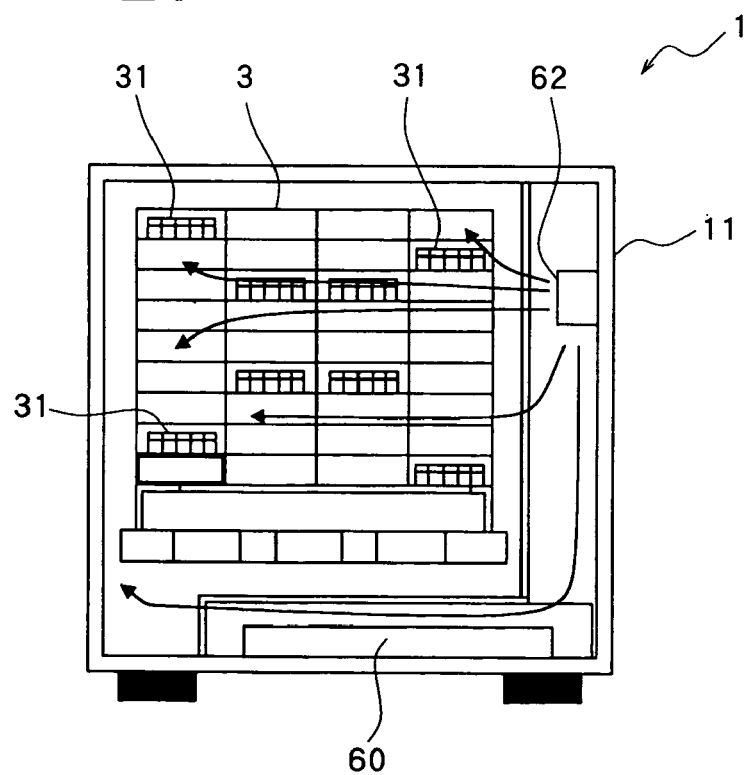
FIG. 21 is a side elevation of the same.

With reference to FIGS. 20 and 21, provided in the rear wall of the chamber 11 for a gas from the environment adjusting device 6 is the discharge outlet 62 facing toward the space wherein the transport device 5 is installed, and the stackers 3, 3 are arranged at opposite sides of the gas outlet 62. Accordingly, the gas forced out from the outlet 62 uniformly diffuses from the central portion of the chamber 11 to the surrounding area, flowing inside the chamber without producing any markedly uneven flow.

As a result, uniform ambient conditions are maintained inside the chamber 11 without any great difference produced locally, permitting the samples on the microplates 31 in the stackers 3 to be cultivated under specified ambient conditions.

The specified ambient conditions are maintained inside the chamber 11 because the microplate inlet 13 of the chamber 11 is opened by the shutter mechanism 14 only when microplates are brought into or out of the chamber, and also because the inlet 13 is provided with an air curtain produced by an air stream forced out from the air curtain mechanism 16.

Observation and Analysis of Sample on Microplate

Figure 22:
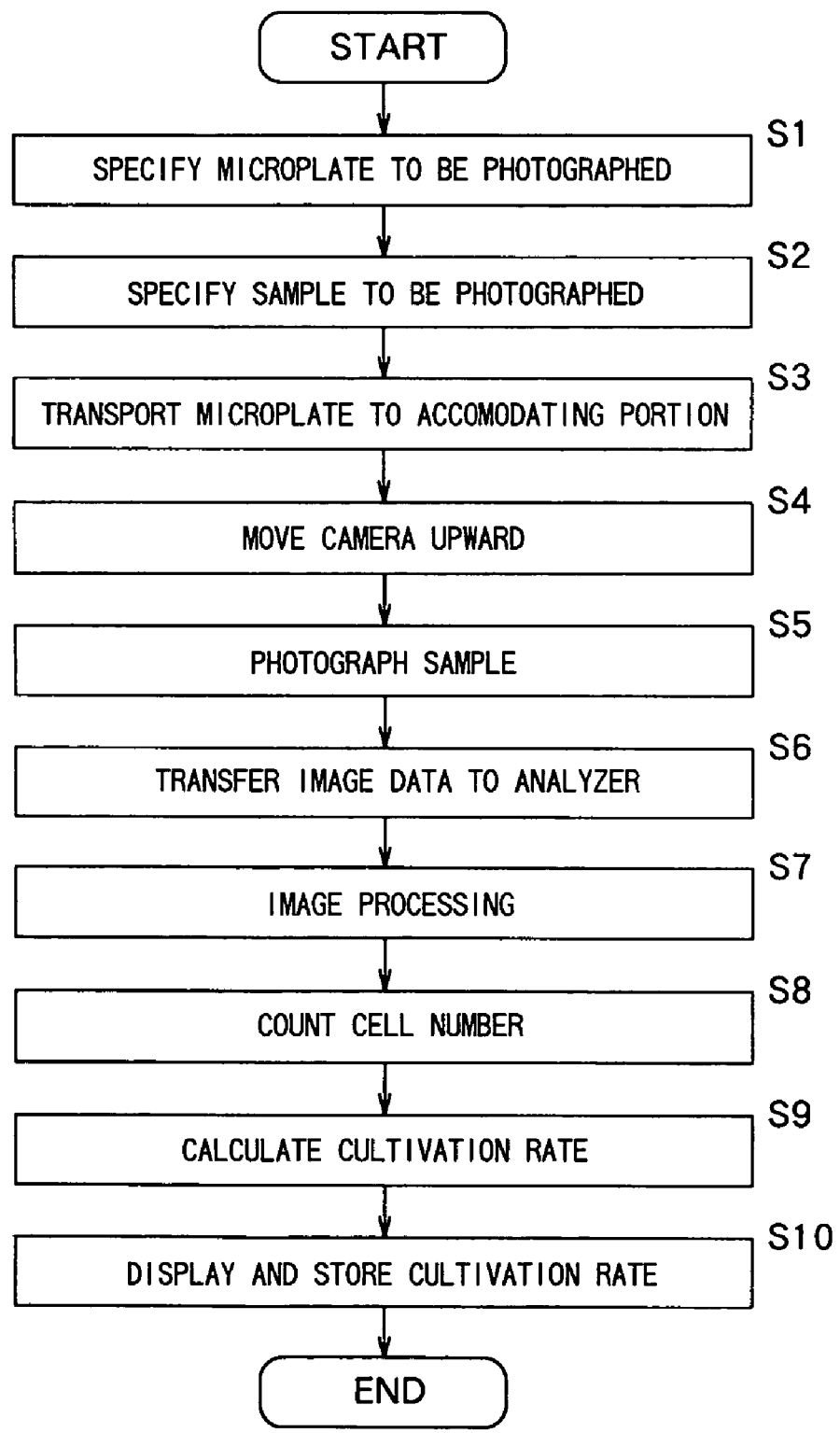
FIG. 22 is a flow chart showing a sample analysis procedure of the incubator of the invention.

The sample on the microplate 31 is observed by the camera 7 shown in FIG. 16, and the procedure shown in FIG. 22 is performed by the analyzer 72 when the growth of the sample is to be analyzed. First, the microplate 31 to be photographed is specified in step S1. The sample to be photographed on the microplate 31 is specified in step 2, whereupon the transport device 5 transports the microplate 31 to an accommodating portion wherein the microplate is to be photographed in step S3.

Figure 23:
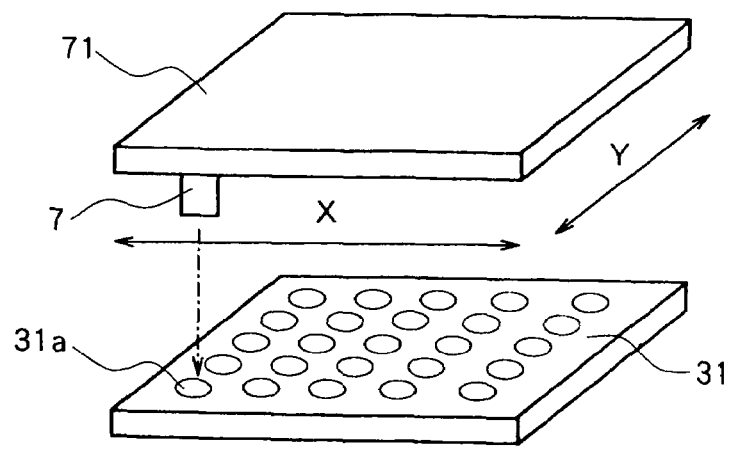
FIG. 23 is a diagram for illustrating the directions in which the camera is driven by a camera drive mechanism.

Subsequently in step S4, the camera 7 is moved in the directions of X-axis and Y-axis by the drive mechanism 71 to position the optical axis of the camera 7 on the specified sample cavity 31a on the microplate 31 as shown in FIG. 23. The camera 7 photographs the sample on the microplate 31 in step S5 of FIG. 22, and the image data obtained by photography is transferred to the analyzer 72 in step S6.

In the following step S7, the analyzer 72 processes the data for image processing in a predetermined manner. The number of cells in the sample is counted in step S8. In step S9, the count is compared with the number of cells before cultivation to calculate the cultivation rate. The calculated rate is shown on the display and stored in a memory.

Figure 24:
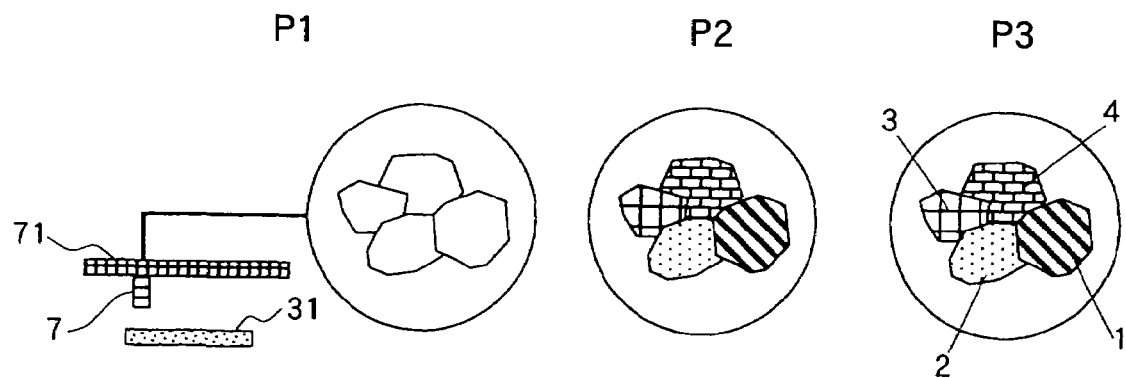
FIG. 24 is a diagram for illustrating an image processing processes.

FIG. 24 shows a sequence of processes for image processing procedure to be performed using the image data obtained from the camera 7. The contours of cells are extracted first in process P1, the cells are distinguished based on the contours in process P2, and the number of cells is counted in process P3 based on the result of distinction. Finally, the cultivation rate is calculated by dividing the count by the count obtained before the cultivation.

Uniformalization of Ambient Conditions

Figure 26:
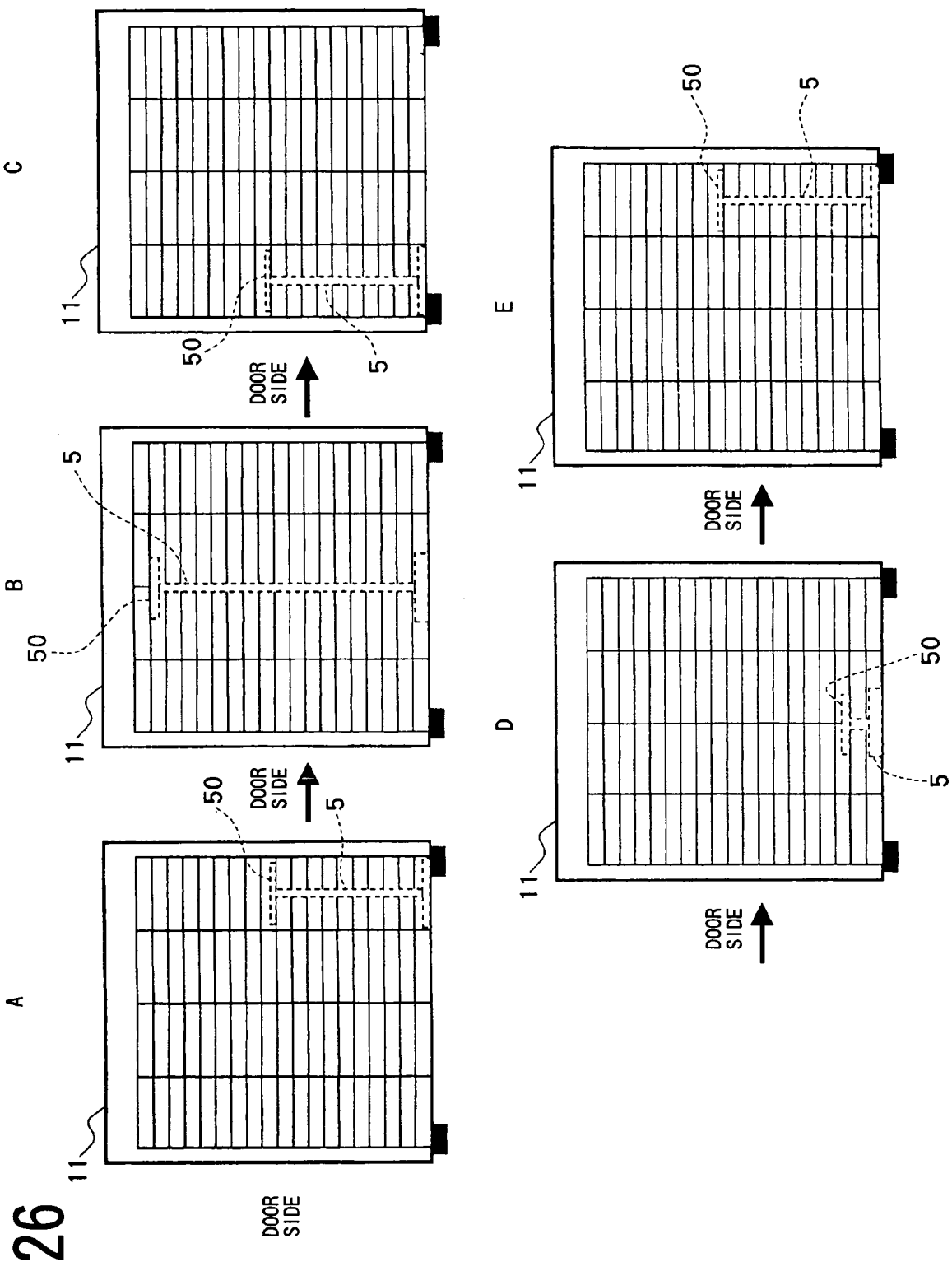
FIG. 26 includes side elevations showing a sequence of movements of the microplate transport device for promoting the circulation of air within the chamber.

To give improved uniformity to the ambient conditions of the atmosphere within the chamber 11 of the incubator 1 of the invention, the microplate transport device 5 is moved in the direction of Y-axis and the direction of X-axis at predetermined timing to revolve the table 50 as shown in FIG. 26, A to E and to promote the circulation of air inside the chamber 11.

Figure 25:
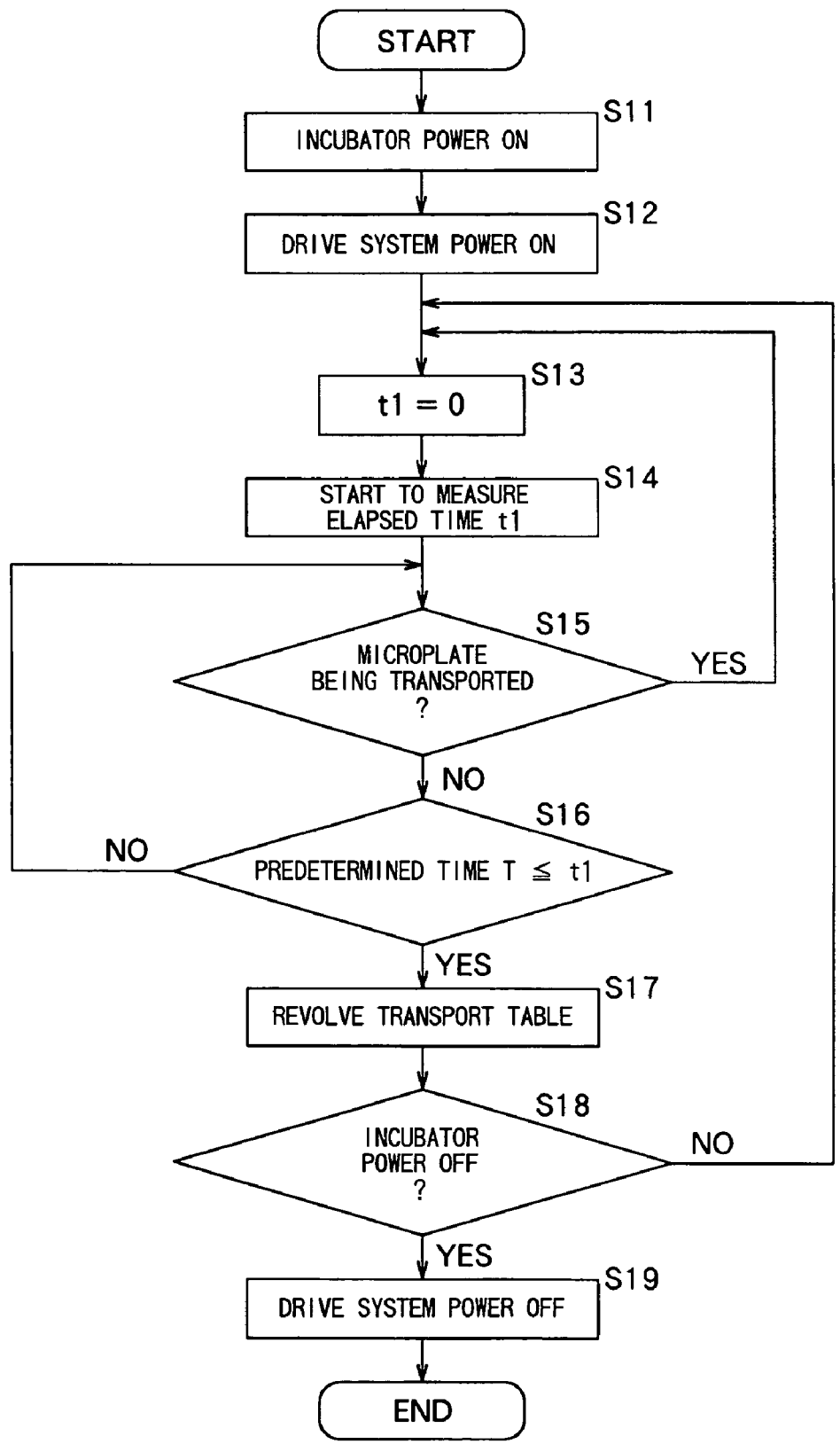
FIG. 25 is a flow chart showing a procedure for promoting the circulation of air within the chamber.

FIG. 25 shows the procedure to be performed by the drive control device 18 for promoting the circulation of air inside the chamber 11. The power source for the incubator 1 is turned on first in step S11. When the power source for the drive system is turned on in step S12, a timer t1 for determining the lapse of time is initialized in step S13, whereupon the measurement of time t1 to be elapsed is started in step S14. Subsequently in step S15, an inquiry is made as to whether the microplate 31 is being transported. If the answer is affirmative, the sequence returns to step S13 again to initialize the timer t1.

When the inquiry of step S15 is answered in the negative, step S16 follows to inquire whether the elapsed time t1 is in excess of a predetermined period of time T. When the answer is negative, the inquiry of step S15 is repeated.

When the inquiry of step S16 is found to be affirmative with the elapsed time t1 exceeding the predetermined period of time T, the transport device 5 is moved in the directions of X-axis and Y-axis in step S17, revolving the table 50 within the chamber 11 (see FIG. 26).

The following step S18 inquires whether the incubator power source is off, and if the answer is negative, step S13 follows again to repeat steps S13 to S17. When the inquiry of step S18 is answered in the affirmative with the incubator power source subsequently turned off, the sequence proceeds to step S19, in which the drive system power source is turned off to complete the present procedure.

According to the procedure described above, the transport table 50 is held in revolution for a predetermined period of time even after the completion of transport of the table 50, so that the air inside the chamber 11 is stirred by the movement of the table 50. This holds the interior of the chamber 11 under uniform ambient conditions at all times.

Prevention of Water Condensation

If the environment adjusting device 6 is brought out of operation as when the stacker 3 in the incubator 1 of the invention is to be replaced by another one, the internal temperature of the chamber 11 markedly drops, permitting condensation of water vapor inside the chamber 11. In order to protect the motors 571, 581, 591, 421 even if the water condensate ingresses into the motor units 57, 58, 59, 42, the motors 571, 581, 591, 421 are energized with the number of rotation steps set to zero for a predetermined period of time after the operation of the environment adjusting device 6 is halted, whereby these motors are held at a temperature (e.g., 37° C.) not permitting condensation.

Figure 27:
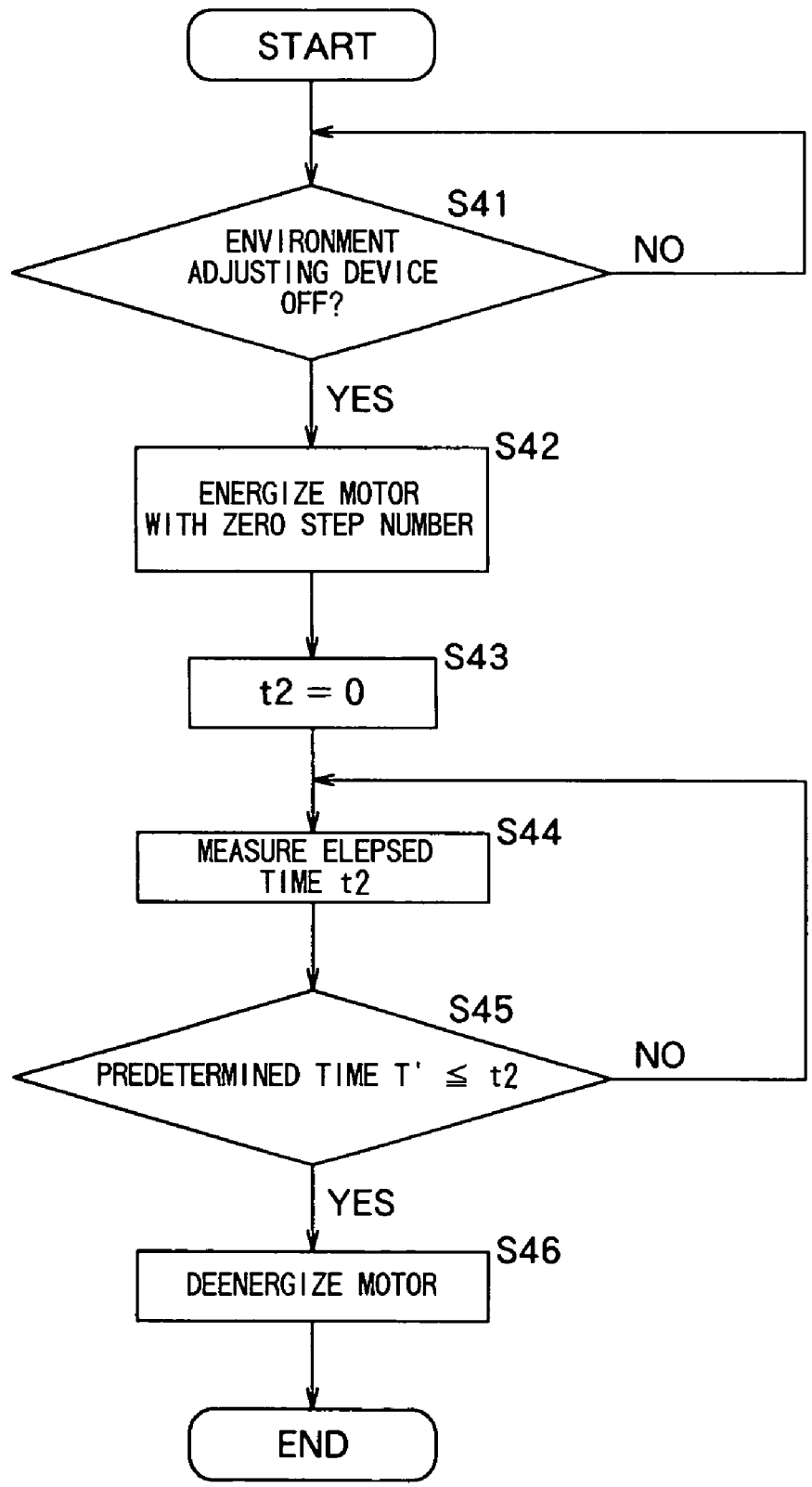
FIG. 27 is a flow chart showing an energization control procedure for a motor for preventing condensation of water vapor on the motor.

FIG. 27 shows this motor energization control procedure. Step S41 first inquires whether the environment adjusting device 6 is brought out of operation, and if the answer is affirmative, the energization of the motors 571, 581, 591, 421 is started with the number of rotation steps set to zero in step S42. A timer t2 is initialized in step S43, and measurement of elapsed time t2 is started in step S44.

In the following step S45, an inquiry is made as to whether the elapsed time t2 is in excess of a predetermined period of time T', and when the answer is negative, the time measurement of step S44 is continued. When the inquiry of step S45 is answered in the affirmative with the elapsed time t2 exceeding the period of time T', step S46 follows to deenergize the motor.

When the environment adjusting device 6 is brought out of operation as for the replacement of the stacker 3, the internal temperature of the chamber 11 markedly drops to permit water condensation inside the chamber 11. However, the motors 571, 581, 591, 421 are energized and held at a high temperature for a specified period of time after the stopping of the operation of the device 6 by the above motor energization control procedure. It is therefore unlikely that the condensation of water vapor will occur inside the motor units 57, 58, 59, 42 even if the ambient temperature drops. The internal humidity of the chamber 11 is reduced to the level of humidity of outside air by opening the door 12 of the chamber 11, for example, to replace the stacker 3 or for the maintenance of the transport device 5, subsequently obviating the likelihood of condensation occurring inside the motor units 57, 58, 59, 42. Accordingly, the motors 571, 581, 591, 421 may be held energized only for the predetermined period time after the operation of the device 6 is discontinued.

Stacker Management System

Figure 28:
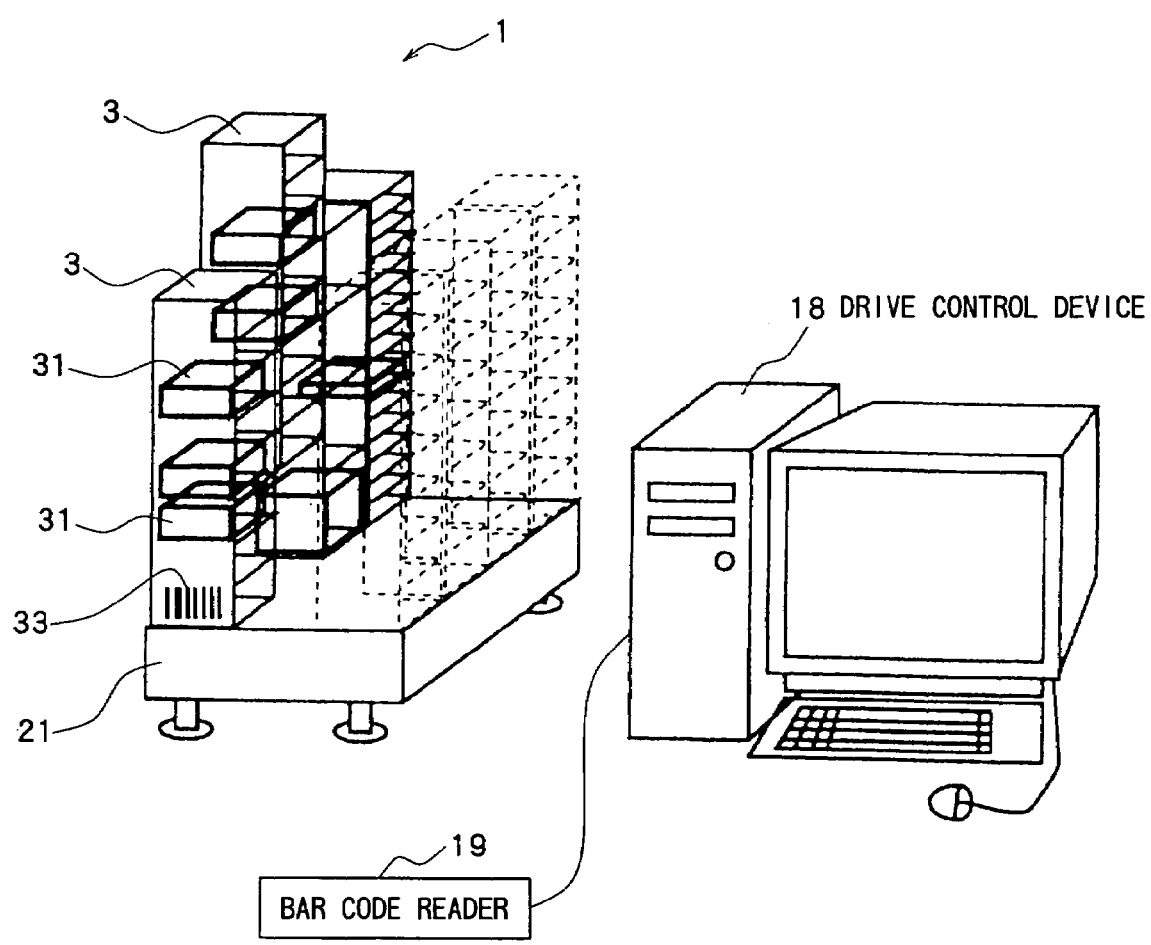
FIG. 28 is a diagram for illustrating management of stackers based on bar codes provided on the stackers.
Figure 32:
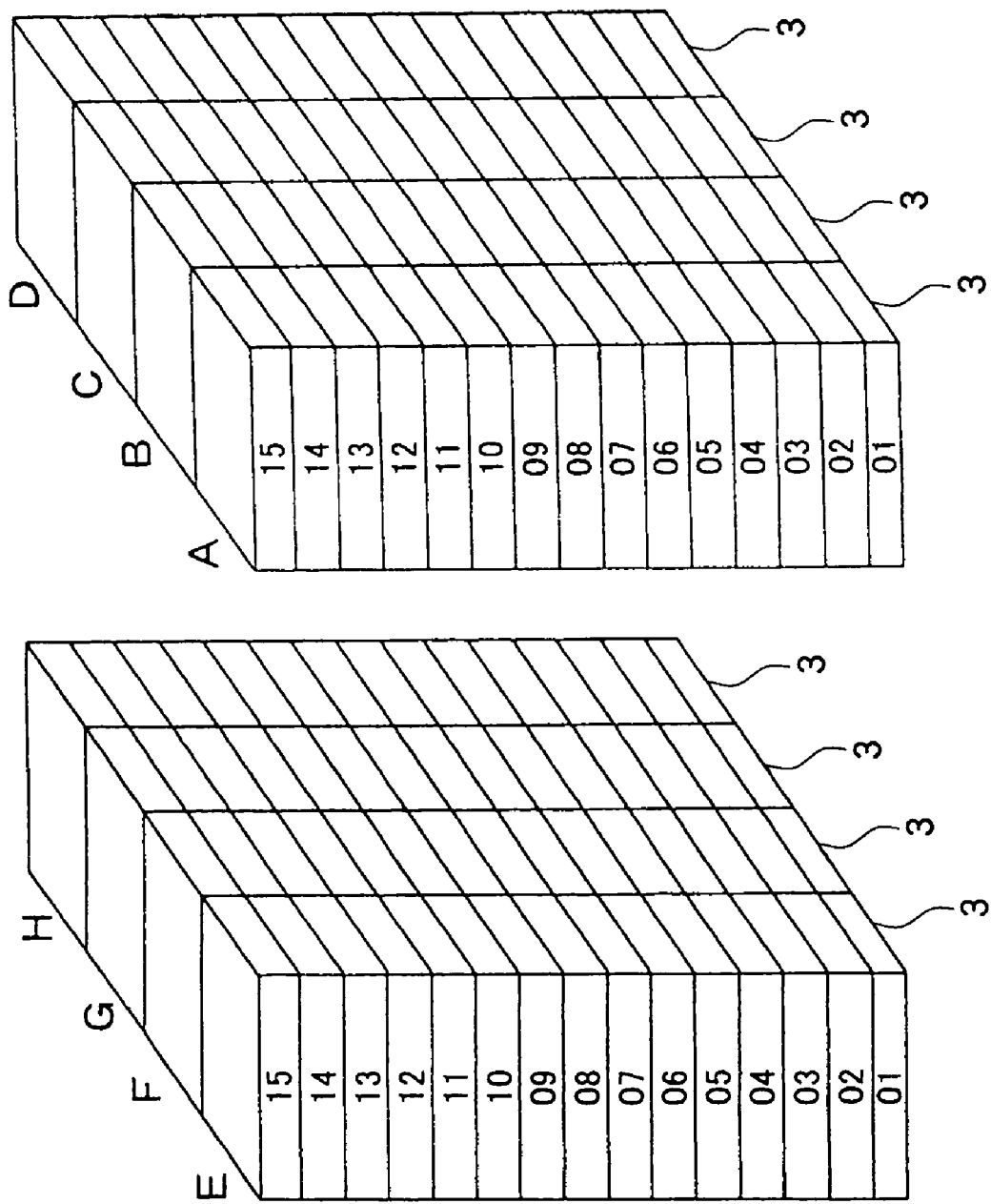
FIG. 32 is a perspective view showing the positions of stackers and the positions of microplate accommodating portions.

Further with incubator 1 of the present invention, as shown in FIG. 28, a bar code 33 is attached to a side wall of each stacker 3 for identifying the stacker 3. The table memory 183 of the drive control device 18 has stored therein a stacker information table shown in FIG. 29. Registered in the table are stacker type numbers, types, sizes and the numbers of microplate accommodating portions (number of racks).

When stackers 3 are provided anew on the base 21 of the incubator 1, the bar codes 33 of the stackers 3 are read by the bar code reader 19 to recognize the identification numbers and type numbers of the stackers 3, and items of data as to the type of each stacker 3, as to the size thereof and as to the number of racks therein are then retrieved from the stacker information table shown in FIG. 29 with reference to the identification number to prepare a stacker information form comprising the identification number and the data as to the type number, type, size and rack number. The operator further enters the position of the stacker 3 on the base 21 and prepares a stacker position form comprising the identification number, data as to the date and time of installation and data as to the position of installation as shown in FIG. 31. Further prepared with reference to the data as to the rack numbers and the positions of installation is a microplate accommodating portion management table to be described below and concerning the stackers installed in the incubator.

FIG. 41 shows a microplate accommodating portion management table to be prepared in the case where eight stackers each having 15 microplate accommodating portions are provided anew in the incubator 1. The English characters "A" to "H" indicate the positions on the base in the incubator, and the numbers "01" to "15" represent stage numbers. When new stackers are provided, consecutive identification numbers starting with "001" are given to the respective microplate accommodating portions in the lowermost stage of the stacker at position A through the uppermost stage of the stacker at position H, and a microplate accommodating portion management table is prepared from the identification numbers of all the accommodating portions and data "VC" indicating the absence of the microplate in each of these portions. The data "VC" indicates that no microplate is accommodated in the portion concerned, and when a microplate is thereafter placed into the portion, the data is changed to "OP" as will be described below.

Figure 33:
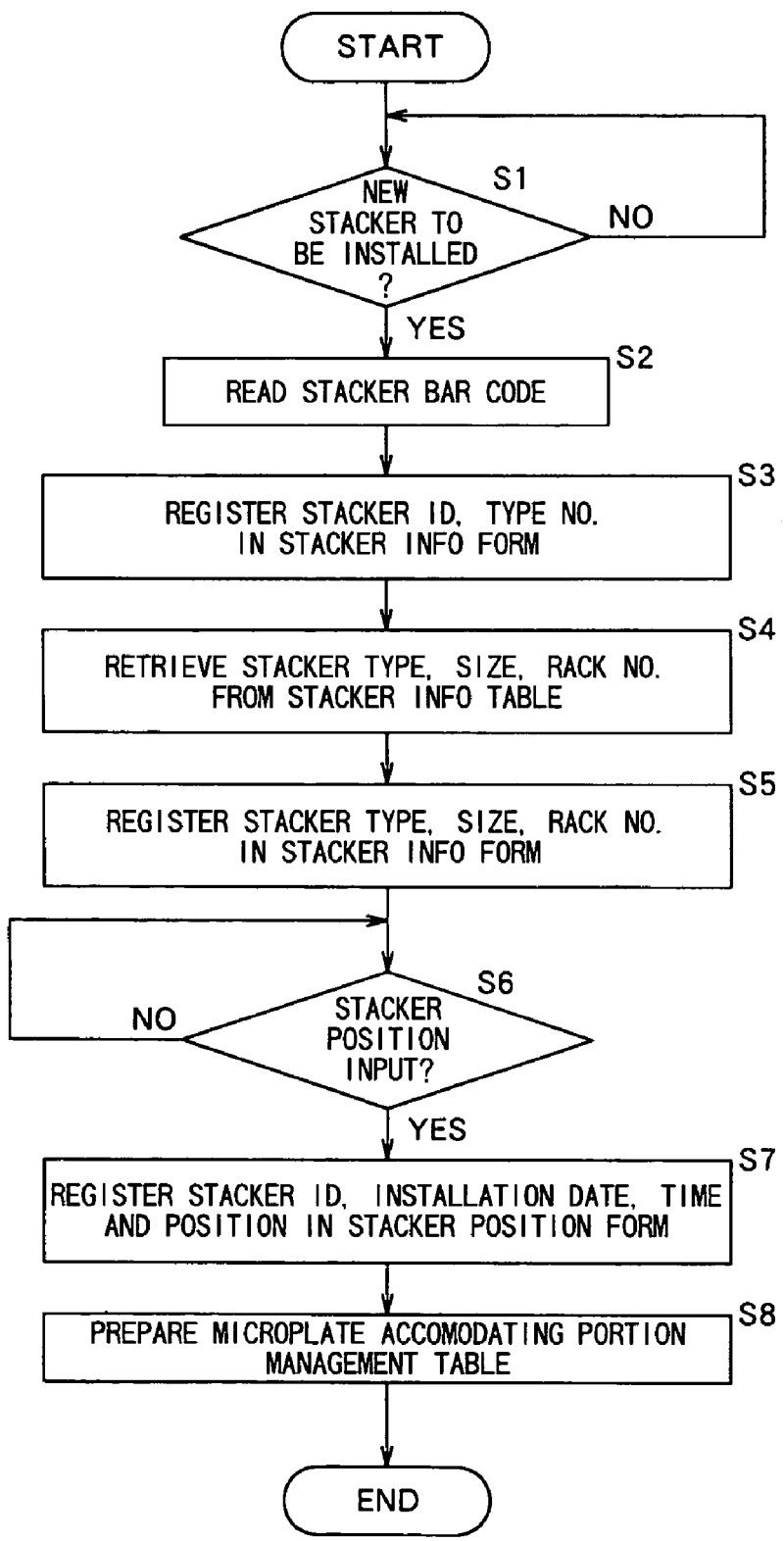
FIG. 33 is a flow chart showing a procedure to be executed when a stacker is to be installed anew.

FIG. 33 shows a procedure to be performed when a new stacker is to be installed. An inquiry is made first in step S1 as to whether a stacker is to be installed anew. When the answer is affirmative, the bar code of the stacker to be installed is read by the bar code reader 19 in step S2, followed by step S3 to decode the bar code read and register the identification number and type number obtained in a stacker information form prepared anew.

In the following step S4, items of data as to the type, size and rack number of the new stacker to be installed is retrieved from the stacker information table shown in FIG. 29 with reference to the type number. In step S5, these items of data retrieved are written in the stacker information form prepared.

The following step S6 inquires whether the position of the stacker is input. If the answer is affirmative, the identification number obtained by decoding the bar code, date and time of installation and the position of stacker are registered in a new stacker position form prepared in step S7. A microplate accommodating portion management table is prepared finally in step S8 with reference to the number of racks and the stacker position to complete the procedure.

Every time a new stacker is installed, a stacker information form and a stacker position form are prepared for each stacker, and a microplate accommodating portion management table is prepared.

When the position of a stacker 3 is to be changed thereafter within the incubator, the operator enters the identification number of the stacker to be moved and the position to which the stacker is to be moved. When the identification number of the stacker and the new position thereof are entered, items of data as to the rack number and the position of installation are retrieved from the stacker information form wherein the identification number is registered and the stacker position form, the microplate accommodating portion management table is updated with reference to the items of data as to the rack number and the installation position retrieved and the new position data. Further the installation position registered in the stacker position form is changed to the new position data.

When a stacker 3 is to be delivered from the incubator to the outside, the operator enters the identification number of the stacker to be taken out. When the stacker identification number is entered, the data as to the installation position is retrieved from the stacker position form wherein the number is registered, and the microplate accommodating portion management table is updated based on the retrieved installation position data. The stacker information form and the stacker position form wherein the identification number is registered are erased.

Figure 34:
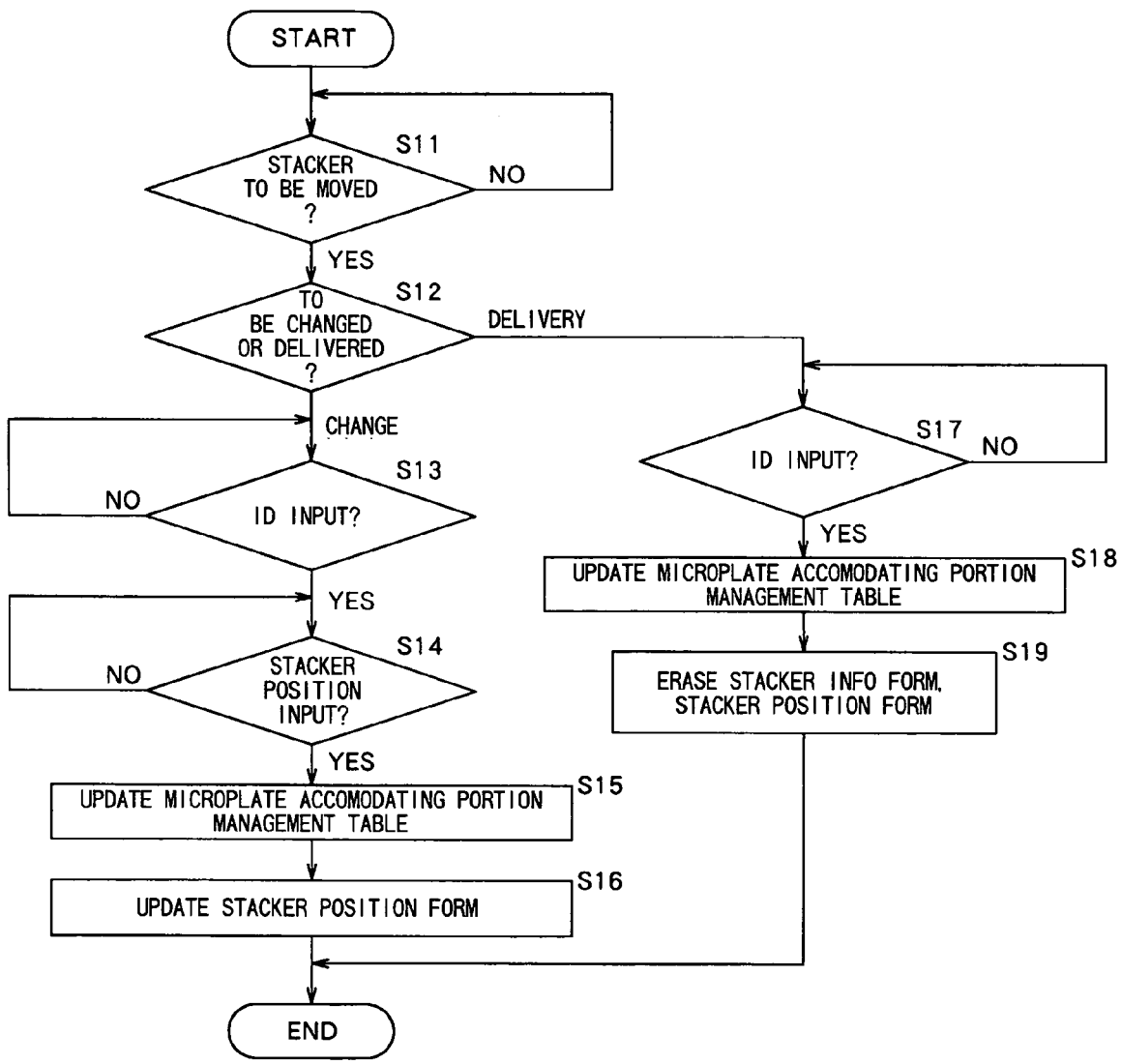
FIG. 34 is a flow chart showing a procedure to be executed when a stacker is to be moved.

FIG. 34 shows the procedure to be executed when a stacker is to be moved. An inquiry is made first in step S11 as to whether the stacker is to be moved. If the answer is affirmative, an inquiry is made in step S12 as to whether the position of the stacker is to be changed within the incubator, or the stacker is to be taken out.

In the case where the stacker position is to be changed inside the incubator, step S13 inquires whether the identification number of one stacker is input, and if the answer is affirmative, an inquiry is made as to whether a destination position to which the stacker is to be moved is input. When the answer is affirmative, an item of data as to the rack number and an item of data as to the installation position are retrieved from the stacker information form and the stacker position form wherein the identification number input is registered. The microplate accommodating portion management table is updated with reference to the rack number data and the installation position data retrieved and the position data input. The installation position registered in the stacker position form is changed to the input position finally in step S16, whereby the present procedure is completed.

On the other hand, in the case where the stacker is to be taken out of the incubator, an inquiry is made in step S17 as to whether the identification number of one stacker is input. When the answer is affirmative, installation position data is retrieved in step S18 from the stacker position form wherein the input identification number is registered, and the microplate accommodating portion management table is updated based on the retrieved installation position data. Finally in step S19, the stacker information form and the stacker position form having the input identification number registered therein is erased, whereby the procedure is completed.

In the case where the stacker position is changed inside the incubator, the microplate accommodating portion management table and the stacker position form of the stacker concerned are updated by the procedure described. Further in the case where the stacker is to be taken out, the microplate accommodating portion management table is updated and the stacker information form and the stacker position form of the stacker concerned are erased.

Figure 35:
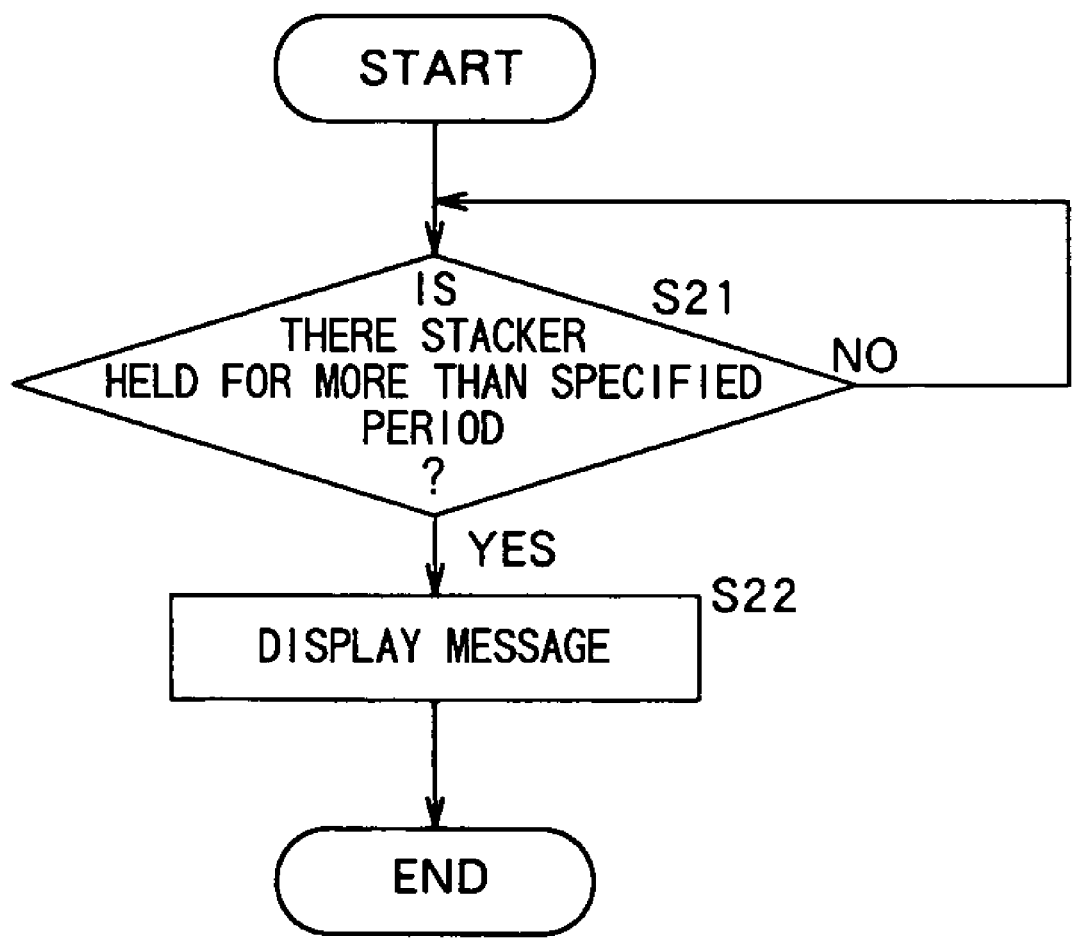
FIG. 35 is a flow chart showing a stacker cleaning time management procedure.

With the incubator 1 of the present invention, when to clean the stacker is managed with reference to the stacker position form described. FIG. 35 shows a stacker cleaning time management procedure. First, step S21 retrieves installation time data from the stacker position forms of all stackers installed in the incubator, and inquires whether there is any stacker among the stackers which has been held installed in the incubator for more than a predetermine period of time, with reference to the data.

If the answer is affirmative, the display of the manipulation panel shows in step S22 a message to the effect that it is time to clean a stacker, whereby the procedure is completed.

Upon arrival of the time to clean, the display of the manipulation panel indicates this by the above procedure. Accordingly, the cleaning time need not be managed by the user.

Microplate Management System

Figure 36:
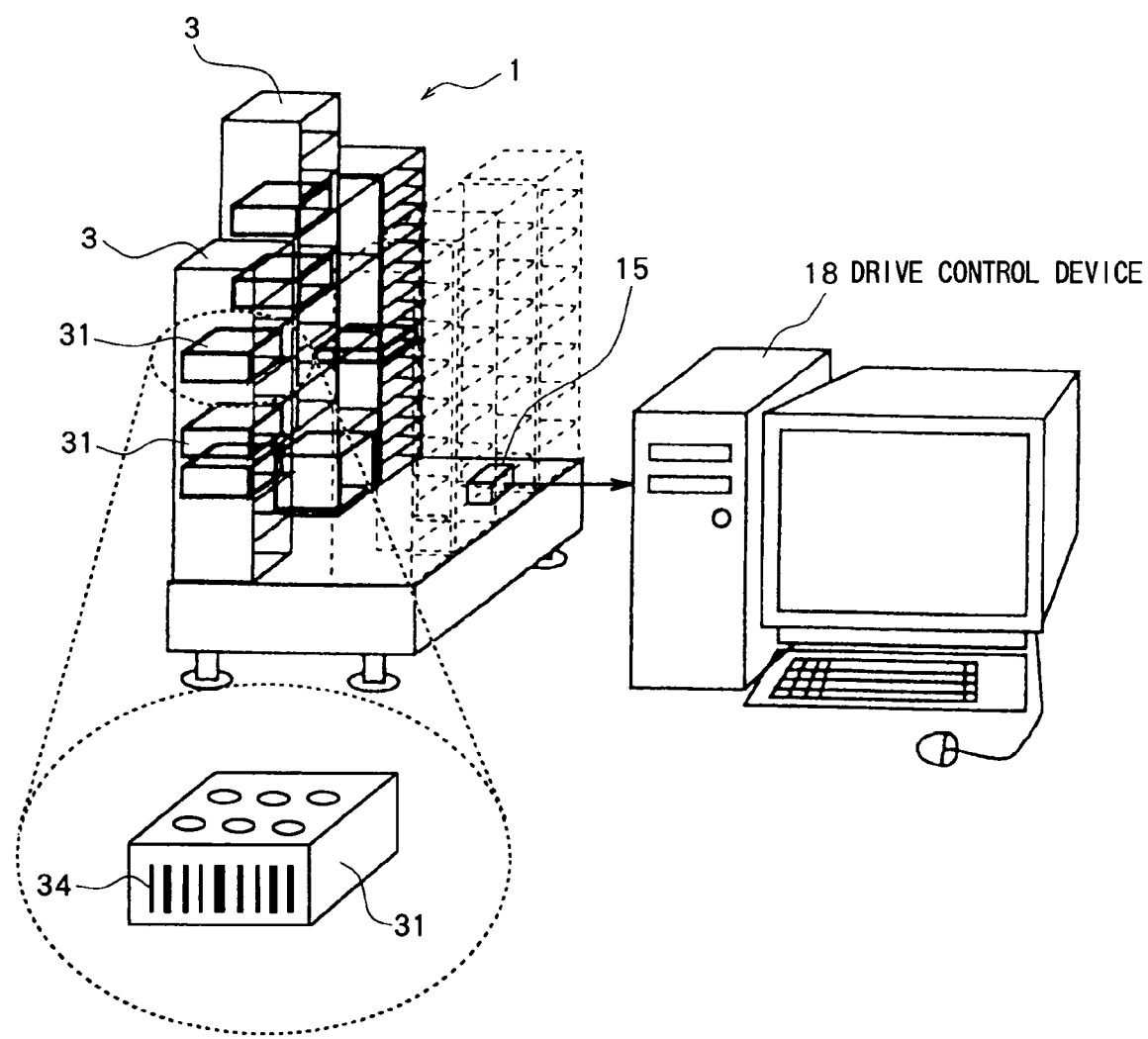
FIG. 36 is a diagram for illustrating management of microplates based on bar codes provided on the microplates.

With the incubator 1 of the present invention, a bar code 34 is provided on a side wall of each microplate 31 for identifying the microplate 31 as shown in FIG. 36. The table memory 183 of the drive control device 18 has stored therein a microplate information table shown in FIG. 37. Registered in the table are the type numbers of microplates, types, sizes and number of sample cavities.

When a microplate 31 is to be placed into the incubator 1, the bar code reader 15 reads the bar code 34 on the microplate 31 while the plate passes through the inlet 13 of the chamber 11, whereby the identification number and type number of the microplate 31 are recognized. With reference to the type number, data as to the type, size and cavity number of the microplate 31 is retrieved from the microplate information table shown in FIG. 37 to prepare a microplate information form shown in FIG. 38 and including data as to the identification number, type number, type, size and cavity number.

Further based on the microplate accommodating portion management table, an optimum accommodating portion is selected, the microplate 31 is placed into the portion, and the microplate absence data as to the accommodating portion is then rewritten to update the management table. Also prepared is a microplate movement history form including the data as to the identification number, placing-in date and time and accommodating position as shown in FIG. 39.

Figure 40:
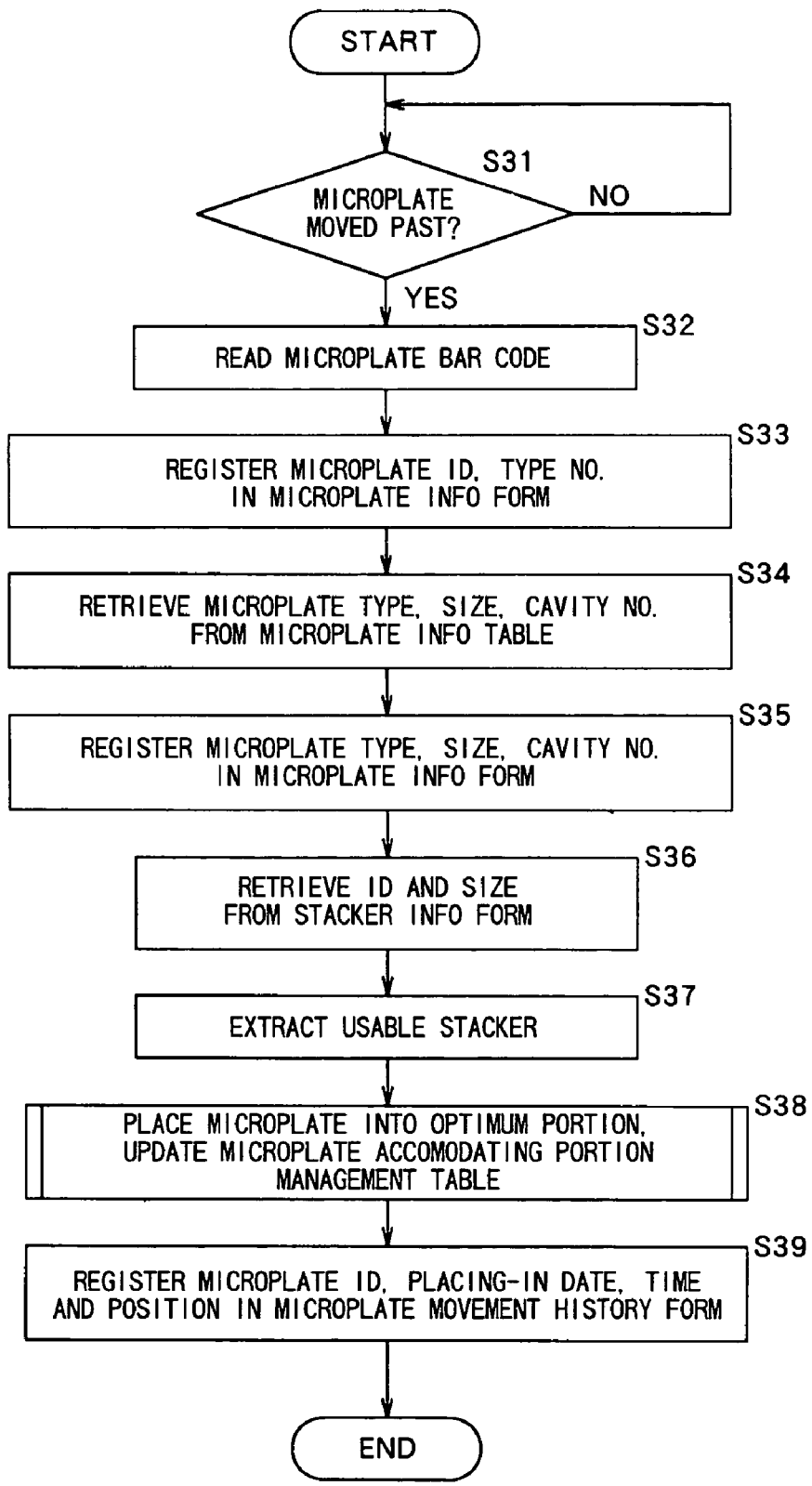

FIG. 40 shows a procedure to be executed when a microplate is placed in. First, step S31 inquires whether the microplate passes through the inlet 13. If the inquiry is answered in the affirmative, the bar code of the microplate is read by the reader 15 in step S32, the read code is decoded in step S33, and the identification number and type number obtained are registered in a microplate information form prepared anew.

In the following step S34, data as to the type, size and cavity number of the microplate to be placed in is retrieved from the microplate information table shown in FIG. 37 with reference to the type number. The retrieved data as to the type, size and cavity number retrieved is written in the microplate information form in step S35.

In the following step S36, data as to identification numbers and sizes is read from the stacker information forms of all stackers installed in the incubator. The size data of the microplate to be placed in is compared with the size data read in step S37 to extract from among all the stackers in the incubator stackers into which the microplate can be placed.

In the subsequent step S38, an optimum microplate accommodating portion is selected from among the microplate accommodating portions of the extracted stackers by the procedure to be described below, the microplate is placed into the optimum portion, and the microplate accommodating portion management table is updated. Finally in step S39, the identification number, placing-in date and time and accommodating position obtained by decoding the bar code are registered in the microplate movement history form, whereby the present procedure is completed.

Every time a microplate is placed in, a microplate information form and a microplate movement history form are prepared for the microplate, and the microplate accommodating portion management table is updated.

With the incubator 1 of the present invention, an optimum microplate accommodating portion is selected to place a microplate therein in accordance with the vacancy of the accommodating portions.

With reference to microplate accommodating portion management tables of FIGS. 42 to 48, a description will be given of a rule of accommodating order in the case where the incubator 1 has installed therein eight stackers each having fifteen microplates accommodating portions. Incidentally, the microplate absence data "VC" represents no microplate accommodated, while the microplate presence data "OP" indicates that a microplate is accommodated.

With reference to FIG. 42, microplates are accommodated first in the portion with an identification number (ID) of "001" in the stacker at position A, then in the portion with an ID of "061" in the stacker at position E, thereafter in the portion with an ID of "005" in the stacker at position A, thereafter in the portion with an ID of "065" in the stacker at position E, . . . that is, microplates are accommodated in every fourth stages alternately in the stacker at position A and the stacker at position E. Likewise as shown in FIG. 43, microplates are accommodated in every fourth stages alternately in two stackers, i.e., in the stacker at position B and the stacker at position F, in the stacker at position C and the stacker at position G, in the stacker at position D and the stacker at position H.

Subsequently as shown in FIG. 44, microplates are accommodated in the portion with an ID of "003" positioned between the portion with an ID of "001" and the portion with an ID of "005" in the stacker at position A, in the portion with an ID of "063" positioned between the portion with an ID of "061" and portion with an ID of "065" in the stacker at position E, in the portion with an ID of "007" in the stacker at position A, in the portion with an ID of "067" in the stacker at position E, . . . that is, microplates are accommodated in every fourth stages alternately in the stacker at position A and the stacker at position E. Likewise as shown in FIG. 45, microplates are accommodated in every fourth stages alternately in two stackers, e.g., in the stacker at position B and the stacker at position F, in the stacker at position C and the stacker at position G, in the stacker at position D and the stacker at position H . . . .

Next as shown in FIG. 46, microplates are accommodated in the portion with an ID of "002" in the stacker at position A, in the portion with an ID of "062" in the stacker at position E, in the portion with an ID of "006", in the portion with an ID of "066" . . . that is, microplates are accommodated in every fourth stages alternately in the stacker at position A and the stacker at position E. Likewise as shown in FIG. 47, microplates are accommodated in every fourth stages alternately in two stackers, e.g., in the stacker at position B and the stacker at position F, in the stacker at position C and the stacker at position G, in the stacker at position D and the stacker at position H . . . .

As shown in FIG. 48, microplates are thereafter accommodated in the portion with an ID of "004" in the stacker at position A, in the portion with an ID of "064" in the stacker at position E, in the portion with an ID of "008", in the portion with an ID of "068" . . . that is, microplates are accommodated in every fourth stages alternately in the stacker at position A and the stacker at position E. Likewise, microplates are accommodated in every fourth stages alternately in two stackers, e.g., in the stacker at position B and the stacker at position F, in the stacker at position C and the stacker at position G, in the stacker at position D and the stacker at position H.

With the incubator 1 of the present invention, optimum microplate accommodating portions are selected according to the above rule to place microplates into the respective selected portions.

Figure 49:
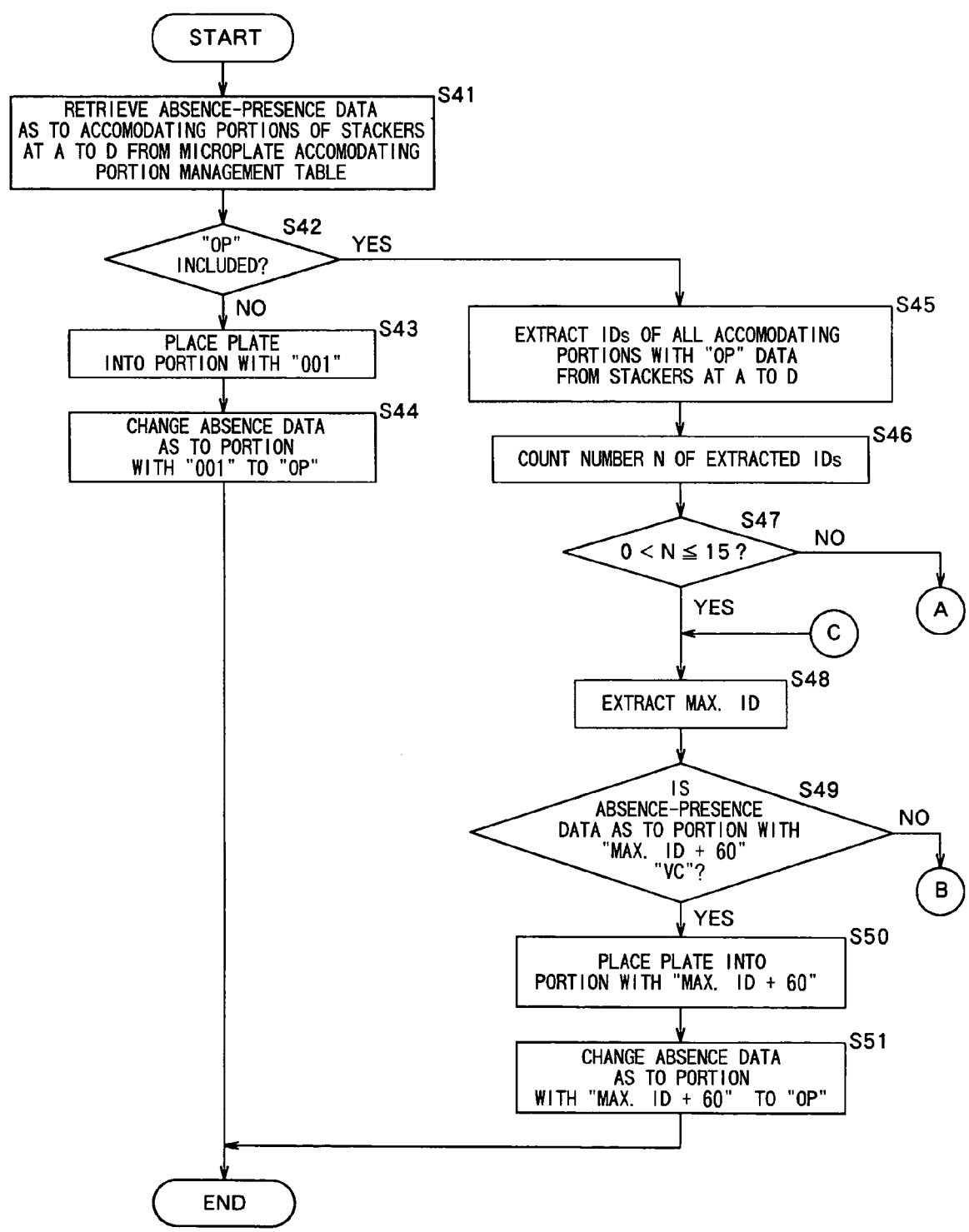
FIG. 49 is a flow chart showing a first part of microplate accommodating procedure.

FIG. 49 shows a specific procedure to be performed in step S38 of FIG. 40 in the case where the incubator 1 has eight stackers each including fifteen microplate accommodating portions. In this procedure, the identification numbers (ID) of microplate accommodating portions are divided into four groups in accordance with by which of the following four mathematical expressions the ID is represented.

Group GR 61

$ID = 61 - 4i$ (Mathematical Expression 1)

i: an integer of not smaller than 1 to up to 15

Group GR 62

$ID = 62 - 4i$ (Mathematical Expression 2)

i: an integer of not smaller than 1 to up to 15

Group GR 63

$$ID = 63 - 4i \qquad \text{(Mathematical Expression 3)}$$

i: an integer of not smaller than 1 to up to 15

Group GR 64

$$ID = 64 - 4i \qquad \text{(Mathematical Expression 4)}$$

i: an integer of not smaller than 1 to up to 15

First, step S41 retrieves all absence-presence data of the stackers at positions A to D from the microplate accommodating portion management table. Step S42 then inquires whether "OP" is included in the retrieved absence-presence data, i.e., whether there is any portion in the stackers at positions A to D which has a microplate accommodated therein. If the first microplate is found accommodated, the answer is interpreted as being answered in the negative, followed by step S43, in which a microplate is accommodated in the portion with an ID of "001". As shown in FIG. 42, the microplate absence data of the accommodating portion with the ID of "001" is thereafter changed to "OP" in step S44 to complete the procedure.

When the second and following microplates are accommodated, the answer to the inquiry of step S42 is found affirmative, whereupon step S45 follows to extract the IDs of all accommodating portions with presence data "OP", i.e., all portions having a microplate accommodated therein, from those in the stackers at positions A to D. In following step S46, the number N of extracted IDs is counted. Step S47 inquires whether the count N is up to 15. When the second to thirty-first microplates are accommodated, the answer is interpreted as being affirmative, followed by step S48.

Figure 50:
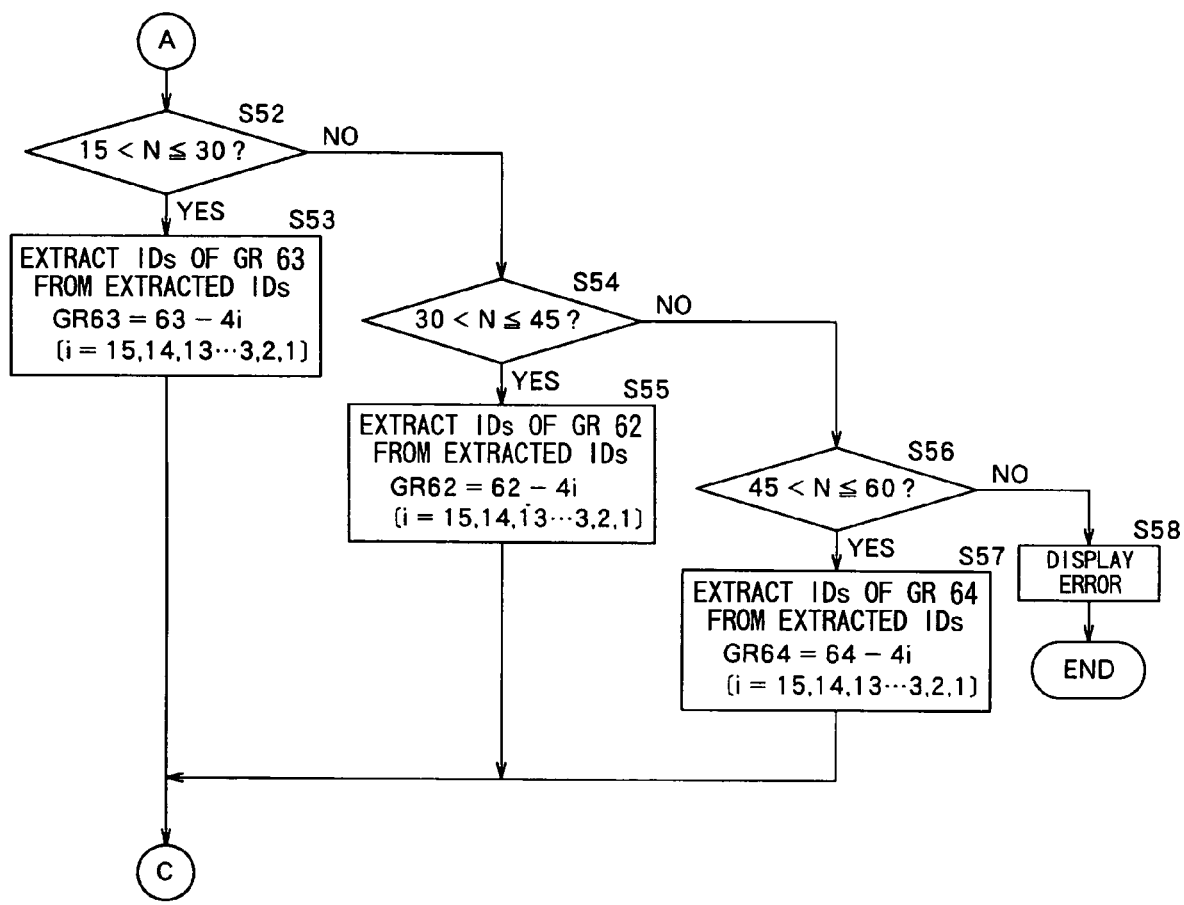
FIG. 50 is a flow chart showing a second part of the procedure.

On the other hand, when the thirty-second and following microplates are accommodated, the answer to the inquiry of step S47 is negative, followed by step S52 of FIG. 50, in which an inquiry is made as to whether the count N is greater than 15 but up to 30. When the thirty-second to sixty-first microplates are accommodated, the answer is affirmative, followed by step S53, in which IDs of group GR 63 are extracted from among the IDs extracted in step S45. Step S48 then follows. For example, when the thirty-second microplate is accommodated, an ID of "003" is extracted in step S53.

When the sixty-second and following microplates are accommodated, the inquiry of step S52 is answered in the negative, and the sequence proceeds to step S54, in which an inquiry is made as to whether the count N is greater than 30 but up to 45. The answer is affirmative when the sixty-second to ninety-first microplates are accommodated. Step S55 then follows, in which IDs of group GR 62 are extracted from among the IDs extracted in step S45. The sequence then proceeds to step S48. For example, when the sixty-second microplate is accommodated, an ID of "002" is extracted in step S55.

When the ninety-second and following microplates are accommodated, the answer to the inquiry of step S54 is negative, and step S56 then follows, in which an inquiry is made as to whether the count N is greater than 45 but up to 60. When the ninety-second to 120$^{th}$ microplates are accommodated, the answer is affirmative, followed by step S57, in which IDs of group GR 64 are extracted from among the IDs extracted in step S45. Step S48 then follows. For example, when the ninety-second microplate is accommodated, an ID of "004" is extracted in step S57. In the case where the answer to the inquiry of step S56 is negative, an error message is given on the display 171 of the manipulation panel 17 in step S58, whereby the present procedure is completed.

In step S48 of FIG. 49, a maximum ID is extracted. A maximum ID is extracted from the IDs extracted in step S45 when second to thirty-first microplates are accommodated, from the IDs extracted in step S53 when thirty-second to sixty-first microplates are accommodated, from the IDs extracted in step S55 when sixty-second to ninety-first microplates are extracted, and from the IDs extracted in step S57 when the ninety-second to 120th microplates are extracted.

Next in step S49, an inquiry is made as to whether the absence-presence data for the microplate accommodating portion with an ID greater than the maximum ID by 60 is "VC", i.e., as to whether the portion with that ID is vacant. When an even-numbered microplate is accommodated, the answer is affirmative, and a microplate is placed into the portion with an ID greater than the maximum ID by 60 in step S50. The absence data as to that accommodating portion is changed to "OP" in step S51, whereby the procedure is completed.

For example as to the second microplate, a maximum ID of "001" is extracted in step S48, and the plate is placed into the portion with an ID of "061" in step S50. A maximum ID of "003" is extracted in step S48 for the thirty-second microplate, which is placed into the portion with an ID of "063" in step S50. A maximum ID of "002" is extracted in step S48 for the sixty-second microplate, which is placed into the portion with an ID of "062" in step S50. A maximum ID of "004" is extracted in step S48 for the ninety-second microplate, which is placed into the portion with an ID of "064" in step S50.

Figure 51:
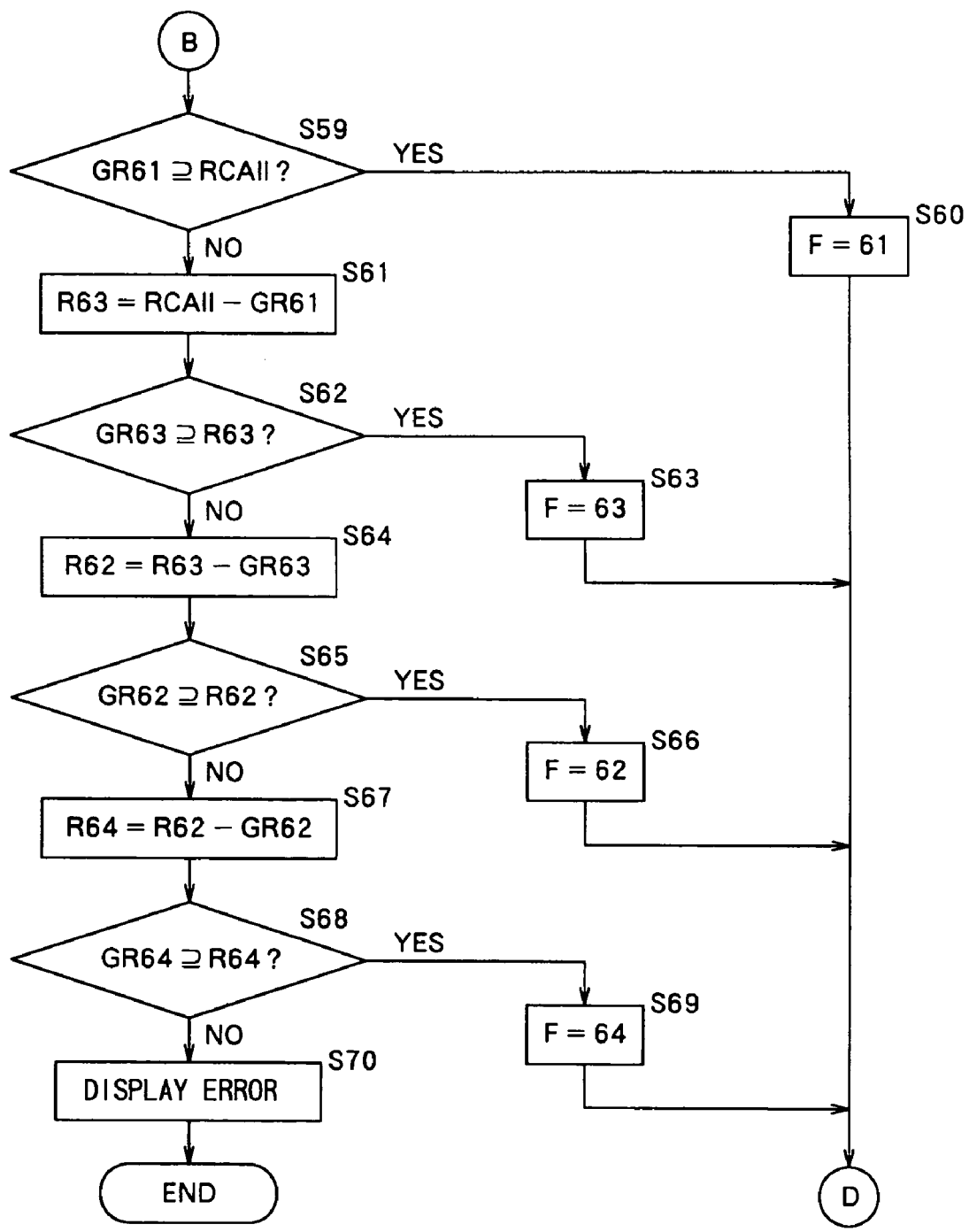
FIG. 51 is a flow chart showing a third part of the procedure.

When odd-numbered microplates are accommodated, the answer to the inquiry of step S49 is negative, followed by step S59 of FIG. 51, in which an inquiry is made as to whether all the IDs extracted in step S45 are included in group GR 61. When third to thirty-first odd-numbered microplates are accommodated, the answer is affirmative, followed by step S60, in which a flag is set at 61. Step S71 of FIG. 52 then follows.

On the other hand, when the thirty-third and following microplates are accommodated, the answer to the inquiry of step S59 is negative, followed by step S61, in which the IDs other than group GR 61 are extracted from among the IDs extracted in step S45. The sequence then proceeds to step S62 to inquire whether all the extracted IDs are included in group GR 63. The answer is affirmative when thirty-third to sixty-first microplates are accommodated. In the following step S63, the flag is set at 63, followed by step S71 of FIG. 52.

The answer to the step S62 is negative when the sixty-third and following microplates are accommodated. Step S64 then follows to extract IDs other than group GR 63 from among the IDs extracted in step S61. An inquiry is then made in step S65 as to whether all the extracted IDs are included in group GR 62 in step S65.

The answer is affirmative when the sixty-third to ninety-first odd-numbered microplates are accommodated, followed by step S66, in which the flag is set at 62. Step S71 of FIG. 52 then follows.

When the ninety-third and following microplates are accommodated, the answer to step S65 is negative, whereupon step S67 follows to extract IDs other than group GR 62 from among the IDs extracted in step S64. In the following step S68, all the extracted IDs are included in group GR 64.

The answer is affirmative when ninety-third to 119$^{th}$ odd-numbered microplates are accommodated, followed by step S69, in which the flag is set at 62. Step S71 of FIG. 52 then follows. In the case where the answer to step S68 is negative, step S70 shows an error message on the display 171 of the manipulation panel 17, whereby the procedure is completed.

Figure 52:
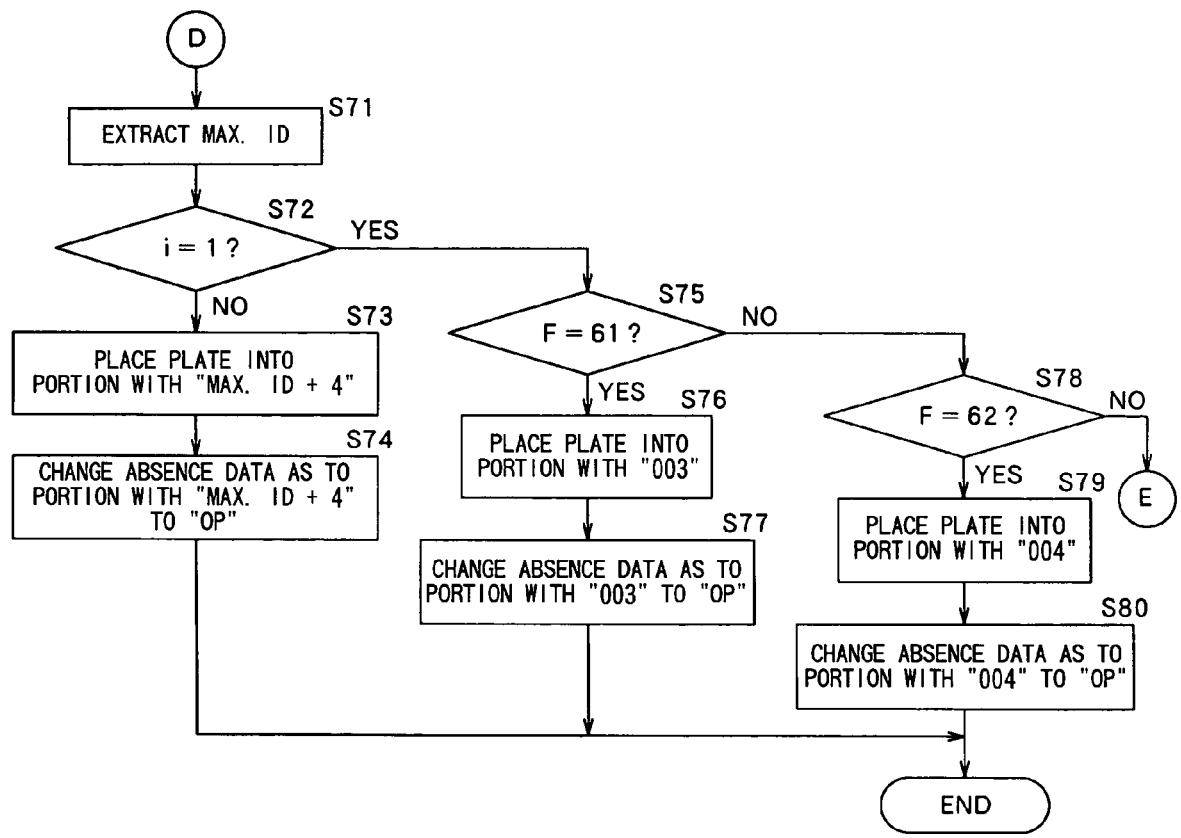
FIG. 52 is a flow chart showing a fourth part of the procedure.

In step S71 of FIG. 52, a maximum ID is extracted. A maximum ID is extracted from the IDs extracted in step S45 when third to thirty-first odd-numbered microplates are accommodated, from the IDs belonging to group GR 63 among IDs extracted in step S45 when thirty-third to sixty-first odd-numbered microplates are accommodated, from the IDs belonging to group GR 62 among the IDs extracted in step S45 when sixty-third to ninety-first odd-numbered microplates are extracted, and from the IDs belonging to group GR 64 among IDs extracted in step S45 when the ninety-third to 119th odd-numbered microplates are extracted.

In the following step S72, an inquiry is made as to whether the variable i is 1 when the maximum ID is expressed by the foregoing mathematical expressions, i.e., whether the maximum ID is one of "057", "058", "059" and "060".

When 3rd to 29th, 33rd to 59th, 63rd to 89th, 93rd to 119th odd-numbered microplates are accommodated, the answer to step S72 is negative, a microplate is placed into an accommodating portion with an ID greater than the maximum ID by 4 in step S73, and the absence data as to that portion is then changed to "OP" in step S74, whereby the procedure is completed.

A maximum ID of "001" is extracted in step S71, for example, for the third microplate, which is placed into the accommodating portion with an ID of "005" in step S74. A maximum ID of "003" is extracted in step S71 for the thirty-third microplate, which is placed into the accommodating portion with an ID of "007" in step S74. A maximum ID of "002" is extracted in step S71 for the sixty-third microplate, which is placed into the accommodating portion with an ID of "006" in step S74. A maximum ID of "004" is extracted in step S71 for the ninety-third microplate, which is placed into the accommodating portion with an ID of "008" in step S74.

When the answer to step S72 is affirmative, step S75 follows to inquire whether the flag is set at 61. The answer is affirmative when the thirty-first microplate is accommodated, and the microplate is placed into the accommodating portion with an ID of "003" in step S76, and the absence data for the portion with the ID of "003" is then changed to "OP" in step S77, whereby the procedure is completed.

When the answer to step S75 is negative, step S78 follows to inquire whether the flag is set at 62. The answer is affirmative when the ninety-first microplate is accommodated. Step S79 then follows to place the microplate into the portion with an ID of "004", and the absence data for the portion with the ID of "004" is thereafter changed to "OP" in step S80.

Figure 53:
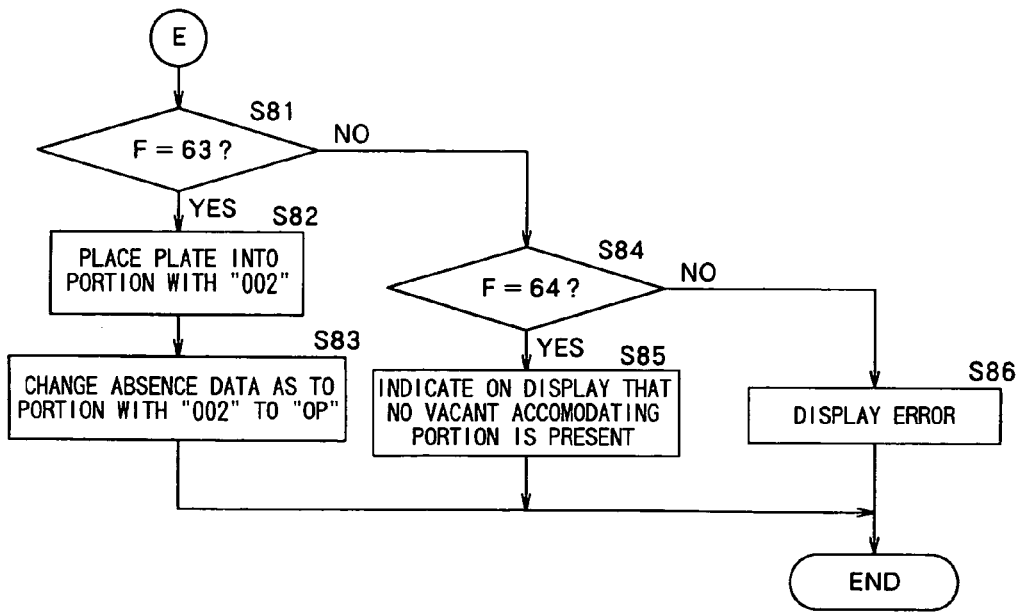
FIG. 53 is a flow chart showing a fifth part of the procedure.

In the case where the answer to step S78 is negative, step S81 of FIG. 53 follows to inquire whether the flag is set at 63. The answer is affirmative when the sixty-first microplate is accommodated, followed by step S82 to place the microplate into the portion with an ID of "002", and the absence data as to the portion with the ID of "002" is thereafter changed to "OP" in step S83, whereby the procedure is completed.

When the answer to step S81 is negative, step S84 follows to inquire whether the flag is set at 64. If the answer is affirmative, the sequence proceeds to step S85, in which the display 171 of the manipulation panel 17 indicates that there is no vacant accommodating portion to complete the procedure. On the other hand, if the step S84 is answered in the negative, an error message is given on the display 171 of the manipulation panel 17 in step S86 to complete the procedure.

A microplate is placed into an optimum accommodating portion in conformity with the rule by the foregoing procedure, while the absence data for the accommodating portion is changed to "OP" to update the microplate accommodating portion management table.

When the second to thirtieth microplates are placed into the incubator of the invention, three vacant accommodating portions are provided between the plate accommodated portions as seen in FIG. 43. When thirty-first to sixtieth microplates are accommodated, one vacant accommodating portions are provided as seen in FIG. 45. Accordingly, the gas forced out from the discharge outlet 62 shown in FIGS. 20 and 21 is uniformly applied to all the microplates 31 placed in the stackers 3 over the plate surfaces. The four stackers at positions A to D and the four stackers at positions E to H accommodate nearly the same number of microplates 31, so that the gas forced out from the discharge outlet 62 uniformly diffuses from the central portion of the interior of the chamber 11 toward the stackers at opposite sides. Ambient conditions can consequently be maintained inside the chamber 1 with improved uniformity.

When the position of the microplate 31 is to be changed inside the incubator thereafter, the ID of the microplate to be shifted and the destination position are input by the operator. When these items of data are input, the microplate is placed into the portion at the specified position, and the microplate accommodating portion management table is then updated. Furthermore, the data and time of movement and the new position are registered in the microplate movement history form for the microplate concerned as shown in FIG. 54.

When the microplate 31 is delivered from the incubator to the outside, the ID of the microplate to be taken out is entered by the operator.

When the ID of the microplate is input, the microplate is discharged from the incubator, and the microplate management table is thereafter updated and the microplate information form and the microplate movement history form of the microplate concerned are erased.

Figure 55:
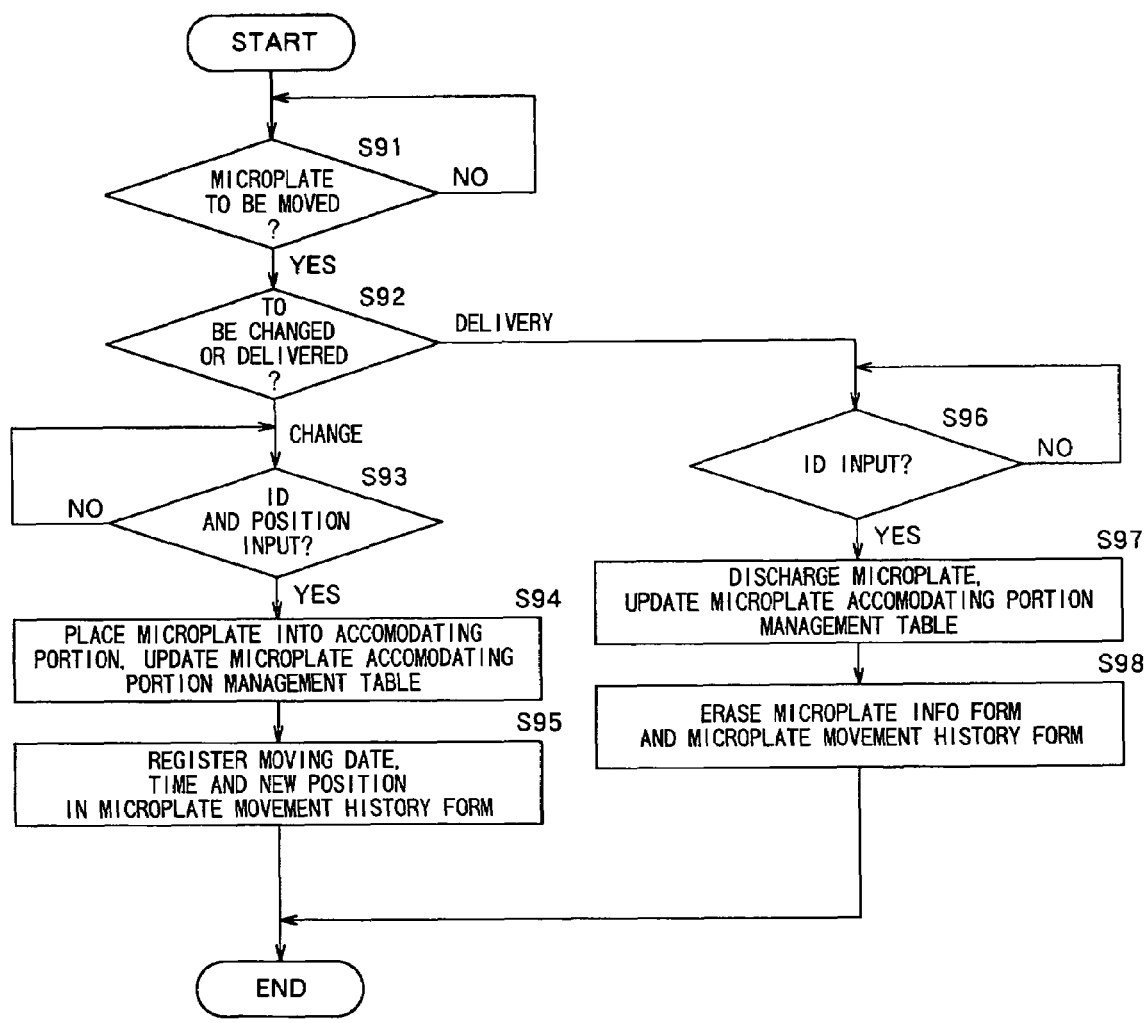
FIG. 55 is a flow chart showing a procedure to be executed when a microplate is moved.

FIG. 55 shows the procedure to be performed when a microplate is moved. First, step S91 inquires whether the microplate is to be moved. When the stacker is to be moved, an inquiry is made in step S92 as to whether the microplate is shifted inside the incubator or taken out of the incubator.

When the position of the microplate is to be changed inside the incubator, step S93 inquires whether the ID of the microplate and the destination position to which the plate is to be moved are input. When the answer is affirmative, the current position of the microplate having the ID is recognized in step S94 with reference to the microplate movement history form wherein the input ID is registered, the microplate in the position is placed into the accommodating portion at the input position, and the microplate accommodating portion management table is thereafter updated. Finally in step S95, the date and time of movement and the input position are registered in the microplate movement history form concerned to complete the procedure.

On the other hand, when the microplate is to be delivered from the incubator to the outside, step S96 inquires whether the ID of the microplate is input. When the answer is affirmative, the current position of the microplate having the ID is recognized in step S97 with reference to the microplate movement history form wherein the input ID is registered, the microplate in the position is discharged from the incubator, and the microplate accommodating portion management table is thereafter updated. Finally in step S98, the microplate information form and the microplate movement history form of the microplate concerned are erased to complete the procedure.

Through the above procedure, the microplate specified by the operator is placed into the accommodating portion at the specified position, the microplate accommodating portion management table is then updated and the microplate movement history form concerned is updated. Alternatively when the microplate specified by the operator is discharged from the incubator to the outside, the microplate accommodating portion management table is then updated, and the microplate information form and the microplate movement history form of the microplate concerned are erased.

With the incubator 1 of the present invention, microplate delivery time is managed with reference to the microplate movement history form.

Figure 56:
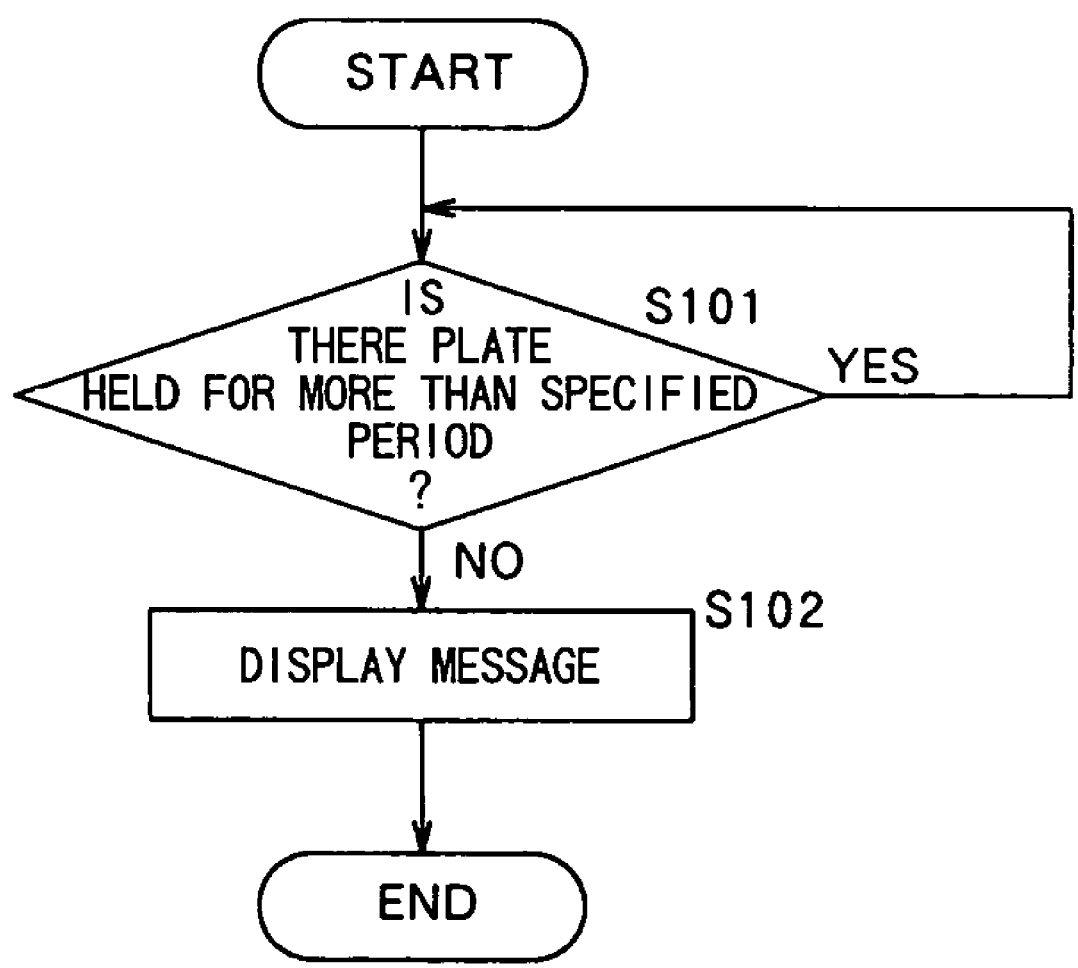
FIG. 56 is a flow chart showing a microplate delivery time management procedure.
Figure 57:
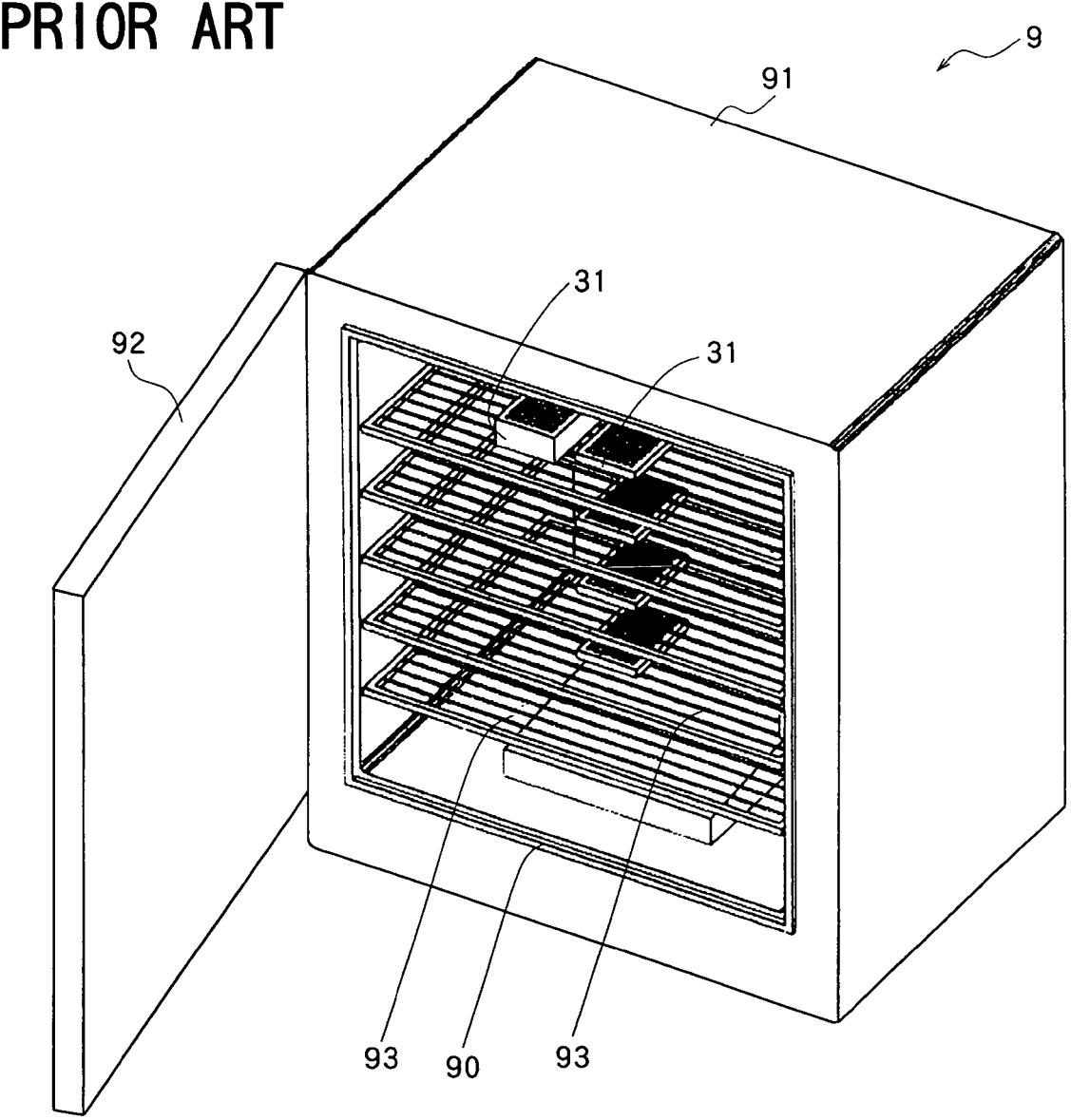
FIG. 57 is a perspective view of a conventional incubator.

FIG. 56 shows a procedure for the management of microplate delivery time. First, step S101 retrieves placing-in time data from the microplate movement history forms of all microplates placed in the incubator, and an inquiry is made as to whether there is any microplate which is held in the incubator for more than a predetermined period of time after having been placed into the incubator, with reference to the placing-in time data. If the answer is affirmative, step S102 shows a message on the display of the manipulation panel to the effect that the time to deliver the microplate has come, whereupon the procedure is completed.

Upon arrival of the time to deliver the microplate, a message to this effect is shown on the control panel display by the above procedure. This eliminates the need for the management of delivery time by the user.

As described above, the incubator 1 of the present invention is adapted to automatically transport microplates 31 and to accommodate a large number of microplates 31 within the chamber 11, with the interior of the chamber 11 held under uniform ambient conditions.

Since all motors 571, 581, 591, 421 constituting the drive mechanism of the incubator unit 2 are housed in the chamber 11 in the case of the incubator 1 of the present invention, the chamber 11 can be simpler in construction than when these motors are arranged outside the chamber 11, with the chamber 11 held highly airtight. Because the chamber 11 and the incubator unit 11 are constructed independently of each other, the microplate transport device 5 can be removed from the chamber 11 without being disassembled, for example, for maintenance. This ensures efficient work and makes the construction of the incubator unit 2 universally useful.

Further the incubator 1 of the present invention has a camera 7 disposed inside the chamber 11 for photographing samples on the microplate 31. This makes it possible to observe and analyze the sample without taking out the microplate 31 from the chamber 11 to the outside. This serves to hold the interior of the chamber 11 under specified ambient conditions and assure an efficient analysis.

The incubator 1 of the present invention is further adapted to automatically transport microplates with reference to the stacker information form, stacker position form, microplate information form, microplate movement history form and microplate accommodating portion management table.

The incubator 1 of the invention is further adapted to automatically place microplates into optimum accommodating portions without the need for the operator to specify the optimum accommodating portions, and eliminates the need to manage the time to clean the stacker and the time to deliver the microplate from the incubator.

The apparatus of the present invention is not limited to the foregoing embodiment in construction but can be modified variously by one skilled in the art without departing from the spirit of the invention as set forth in the appended claims. For example the microplate carriage mechanism 4 need not be provided only at a side portion of the chamber 11 but can be installed, for example, at a rear portion of the chamber 11. Further the present invention is applicable not only to incubators but also to freezers for storing enzymes, etc. at low temperatures. With this type of the freezer, supplying cold air to the inside of the freezer or cooling inner walls is a major method for cooling.

The invention claimed is:

1. A culture apparatus for culturing samples on containers inside a chamber adjusted to predetermined ambient conditions, wherein a container transport device is disposed inside the chamber centrally thereof and comprises a transport table for placing the container thereon, and a drive mechanism for driving the transport table in the direction of X-axis and the direction of Y-axis which are orthogonal on a horizontal plane, and in the direction of Z-axis orthogonal to these directions, a container accommodating rack being disposed on each of opposite sides of the transport devices, which sides are along the direction of X-axis, the accommodating rack having container accommodating portions in the direction of Y-axis and in the direction of Z-axis for accommodating therein respective containers, the container being movable into or out of the desired container accommodating portion of the desired rack by the transport device, wherein the container accommodating rack comprises a plurality of stackers arranged in the direction of Y-axis, and each of the stackers comprises container accommodating portions repeatedly provided in the direction of Z-axis, the chamber has an opening facing toward the direction of Y-axis and a door for closing the opening, and the plurality of stackers constituting the accommodating rack is mounted on a drawer installed on a base and slidable in the direction of Y-axis, the plurality of stackers being withdrawable through the opening along with the drawer, with the door opened, and the chamber has a container inlet for transporting the container into the chamber therethrough, the container inlet having a carriage mechanism connected thereto, and the chamber has attached thereto a shutter mechanism for opening and closing the container inlet, and the container carriage mechanism comprises a container carrier on which the container is mounted and moved in the direction of x-axis, the container carrier being formed with a pair of supports for supporting the container at the opposite sides in the direction of Y-axis, wherein the transport table can be moved to a position under the container supported by the supports, and the transport table can be raised between the supports, wherein the container is lifted from the container carrier by the transport table raised from the position under the container supported by the supports of the container carrier.

2. The culture apparatus according to claim 1, wherein the transport table has a plurality of projections in the direction of Y-axis outwardly of the transport table, formed spacedly in the direction of X-axis on opposite sides in the direction of Y-axis, each of the projections being formed with a wall surface for holding the container between opposite wall surfaces to restrict movement of the container, and the pair of supports of the container carrier has a plurality of projections projecting in the direction of Y-axis inwardly of the container carrier, formed spacedly in the direction of X-axis, each of the projections being formed with a wall surface for holding the container between opposite wall surfaces to restrict movement of the container, the projections of the transport table and the projections of the container carrier being staggered so as not to interfere with each other when the transport table is raised between the supports of the container carrier.

3. A culture apparatus for culturing samples on containers inside a chamber adjusted to predetermined ambient conditions, wherein a container transport device is disposed inside the chamber centrally thereof and comprises a transport table for placing the container thereon, and a drive mechanism for driving the transport table in the direction of X-axis and the direction of Y-axis which are orthogonal on a horizontal plane, and in the direction of Z-axis orthogonal to these directions, a container accommodating rack being disposed on each of opposite sides of the transport device, which sides are along the direction of X-axis, the accommodating rack having container accommodating portions arranged in the direction of Y-axis and in the direction of Z-axis for accommodating therein respective containers, the container being movable into or out of the desired container accommodating portion of the desired rack by the transport device, wherein a plurality of different types of stackers can be arranged inside the chamber for accommodating containers therein, each of the stackers can be arranged inside the chamber for accommodating containers therein, each of the containers being provided with identification information for identifying the container, wherein the chamber has a container inlet for placing the container into the chamber therethrough, and the container inlet has a container carriage mechanism connected thereto, the culture apparatus comprising:

storage means for storing therein stacker type information of each of the stackers that defines a container size accommodatable in the stacker, and the identification information provided on each of the containers, the information having registered therein the container size and a predetermined date and time;

information processing means for storing the stacker type information of each of the stackers and the identification information of each of the containers in the storage means;

means for reading the identification information provided on each of the containers, the means being provided opposite the container inlet;

control means for comparing the size of a container to be accommodated, registered in the read identification information, with the container size accommodatable in the stacker, defined by the stacker type information stored in the storage means, to extract a stacker capable of accommodating the container, and controlling the operation of the container transport device toward one container accommodating portion of the extrated stacker; and an information display device;

wherein the information processing means has a comparison and determination unit for comparing the date and time when the container is accommodated, added to the identification information of the container, with the predetermined date and time registered in the identification information of the container, and determining whether there is any container, the predetermined date and time of which has passed, and stores delivery management information for managing the time to deliver the container in the storage means using the determination result, the control means being operable to monitor the delivery time for the plurality of containers arranged inside the chamber based on the container identification information and the delivery management information stored in the storage means and to give the information display device a command to display arrival of the delivery time upon the arrival of the time to deliver the container.

* * * * *